US012653570B2

(12) United States Patent
Davenport et al.

(10) Patent No.: US 12,653,570 B2
(45) Date of Patent: Jun. 16, 2026

(54) ATRAUMATICALLY FORMED TISSUE COMPOSITIONS, DEVICES AND METHODS OF PREPARATION AND TREATMENT

(71) Applicant: TissueMill Technologies LLC, Syosset, NY (US)

(72) Inventors: Thomas Andrew Davenport, Syosset, NY (US); Paul Mulhauser, New York, NY (US); Gregory C. Guinan, Brooklyn, NY (US)

(73) Assignee: TISSUEMILL TECHNOLOGIES LLC, Syosset, NY (US)

( * ) Notice: Subject to any disclaimer, the term of this patent is extended or adjusted under 35 U.S.C. 154(b) by 702 days.

(21) Appl. No.: 17/946,492

(22) Filed: Sep. 16, 2022

(65) Prior Publication Data

US 2023/0018416 A1     Jan. 19, 2023

Related U.S. Application Data

(63) Continuation of application No. 17/236,130, filed on Apr. 21, 2021, now Pat. No. 11,963,695, which is a
(Continued)

(51) Int. Cl.
*A61B 17/322*     (2006.01)
*A61L 27/36*      (2006.01)
(Continued)

(52) U.S. Cl.
CPC .......... *A61B 17/322* (2013.01); *A61L 27/362* (2013.01); *A61L 27/3695* (2013.01);
(Continued)

(58) Field of Classification Search
CPC .......... A61B 17/322; A61B 2017/3225; A61L 27/3612; A61L 27/3683; A61L 2430/06; A61P 19/02; A61K 35/32; C12M 45/02
See application file for complete search history.

(56) References Cited

U.S. PATENT DOCUMENTS 2,985,389 A     5/1961  Willems
3,666,187 A     5/1972  Norris
(Continued)

FOREIGN PATENT DOCUMENTS

AU     2002229615 B2     2/2006
CN        2381279 Y      6/2000
(Continued)

OTHER PUBLICATIONS

Reveille Cartilage Processor Handling Technique—13-10-30 Rev A, Exactech, 2016 available at: https://www.exac.com/product/reveille-handling-technique, 2 pages.
(Continued)

*Primary Examiner* — Diane D Yabut
(74) *Attorney, Agent, or Firm* — Hoffmann & Baron, LLP

(57)     ABSTRACT
A process and system provides for atraumatic preparation of morselized Tissue Particles (TP)s, such as Full Thickness Skin Graft Particles (FTSGPs), cartilage particles and other organ tissue particles, in a liquid medium. The resultant tissue product may be a suspension of Tissue Particles in an aqueous solution and containing highly viable cells and may be rapidly prepared at bedside or in the operating room and conveniently delivered to a patient through a syringe or similar applicator. The morselized Tissues Particles may be used for surgical applications including wound healing, cosmetic surgery, and orthopedic cartilage repairs.

34 Claims, 41 Drawing Sheets

Related U.S. Application Data continuation of application No. 16/584,755, filed on Sep. 26, 2019, now Pat. No. 11,033,295.

(60) Provisional application No. 62/844,232, filed on May 7, 2019, provisional application No. 62/843,724, filed on May 6, 2019.

(51) Int. Cl.

| | |
|---|---|
| *C12M 1/00* | (2006.01) |
| *C12M 1/33* | (2006.01) |
| *C12N 5/071* | (2010.01) |

(52) U.S. Cl.
CPC ............ *C12M 45/02* (2013.01); *C12M 45/04* (2013.01); *C12N 5/0629* (2013.01); *A61B 2017/3225* (2013.01)

(56) References Cited

U.S. PATENT DOCUMENTS

| | | | |
|---|---|---|---|
| 4,145,008 | A | 3/1979 | Wolford |
| 4,681,571 | A | 7/1987 | Nehring |
| 5,731,199 | A | 3/1998 | Roggero |
| 6,824,087 | B2 | 11/2004 | McPherson et al. |
| 7,270,284 | B2 | 9/2007 | Liao et al. |
| 7,431,230 | B2 | 10/2008 | McPherson et al. |
| 7,794,449 | B2 | 9/2010 | Shippert |
| 7,980,500 | B2 | 7/2011 | Jenni et al. |
| 8,109,961 | B2 | 2/2012 | Deshmukh |
| 8,163,549 | B2 | 4/2012 | Yao et al. |
| 8,286,899 | B2 | 10/2012 | Schowalter et al. |
| 8,491,497 | B2 | 7/2013 | Houser et al. |
| 9,296,984 | B2 | 3/2016 | Cimino et al. |
| 9,909,095 | B2 | 3/2018 | Cimino et al. |
| 9,987,473 | B2 | 6/2018 | Knowlton |
| 10,076,354 | B2 | 9/2018 | Knowlton |
| 10,080,581 | B2 | 9/2018 | Knowlton |
| 10,125,345 | B2 | 11/2018 | Nash et al. |
| 10,219,827 | B2 | 3/2019 | Knowlton |
| 10,314,640 | B2 | 6/2019 | Knowlton |
| 10,321,948 | B2 | 6/2019 | Knowlton |
| 10,335,190 | B2 | 7/2019 | Knowlton |
| 10,335,191 | B2 | 7/2019 | Knowlton |
| 10,336,980 | B2 | 7/2019 | Cimino et al. |
| 10,342,574 | B2 | 7/2019 | Knowlton |
| 10,368,904 | B2 | 8/2019 | Knowlton |
| 10,485,575 | B2 | 11/2019 | Knowlton |
| 10,485,606 | B2 | 11/2019 | Knowlton |
| 10,517,635 | B2 | 12/2019 | Knowlton |
| 10,661,063 | B2 | 5/2020 | Knowlton |
| 10,695,546 | B2 | 6/2020 | Knowlton |
| 10,702,684 | B2 | 7/2020 | Knowlton |
| 10,716,924 | B2 | 7/2020 | Knowlton |
| 10,736,653 | B2 | 8/2020 | Knowlton |
| 2005/0139704 | A1 | 6/2005 | Liao et al. |
| 2006/0111778 | A1 | 5/2006 | Michalow |
| 2007/0148756 | A1* | 6/2007 | Bullen ................... C12M 45/02 435/308.1 |
| 2008/0089870 | A1 | 4/2008 | Ghosh et al. |
| 2008/0153157 | A1* | 6/2008 | Yao et al. .............. A61K 35/32 435/325 |
| 2010/0003300 | A1* | 1/2010 | Markland ............ A61K 31/485 424/497 |
| 2010/0015202 | A1 | 1/2010 | Semler et al. |
| 2010/0152750 | A1 | 6/2010 | Memar |
| 2011/0282238 | A1 | 11/2011 | Houser et al. |
| 2013/0295673 | A1 | 11/2013 | Taghizadeh et al. |
| 2013/0338792 | A1* | 12/2013 | Schmieding ........ A61F 2/30756 623/23.73 |
| 2014/0134212 | A1* | 5/2014 | Shi ...................... A61L 27/3683 424/548 |
| 2016/0024450 | A1 | 1/2016 | Quick et al. |
| 2016/0317170 | A1 | 11/2016 | Knowlton |
| 2016/0374704 | A1 | 12/2016 | Eriksson et al. |

| | | | |
|---|---|---|---|
| 2017/0224874 | A1 | 8/2017 | Maki et al. |
| 2017/0296214 | A1 | 10/2017 | Knowlton |
| 2018/0000504 | A1 | 1/2018 | Knowlton |
| 2018/0057787 | A1 | 3/2018 | Friedman et al. |
| 2018/0236457 | A1 | 8/2018 | Graziano et al. |
| 2018/0250027 | A1 | 9/2018 | Knowlton |
| 2018/0250502 | A1 | 9/2018 | Knowlton |
| 2018/0344340 | A1 | 12/2018 | Knowlton |
| 2018/0344343 | A1 | 12/2018 | Knowlton |
| 2018/0344344 | A1 | 12/2018 | Knowlton |
| 2018/0344345 | A1 | 12/2018 | Knowlton |
| 2018/0353202 | A1 | 12/2018 | Knowlton |
| 2019/0002821 | A1 | 1/2019 | Raviv |
| 2019/0054281 | A1 | 2/2019 | Knowlton |
| 2019/0126020 | A1 | 5/2019 | Knowlton |
| 2019/0134365 | A1 | 5/2019 | Knowlton |
| 2019/0254693 | A1 | 8/2019 | Knowlton |
| 2019/0307480 | A1 | 10/2019 | Knowlton |
| 2022/0305174 | A1 | 9/2022 | Awad et al. |

FOREIGN PATENT DOCUMENTS

| | | | |
|---|---|---|---|
| CN | 1816280 | B | 7/2012 |
| CN | 204281757 | U | 4/2015 |
| CN | 104498350 | B | 7/2016 |
| CN | 106244418 | A | 12/2016 |
| CN | 106244437 | A | 12/2016 |
| CN | 104887292 | B | 10/2017 |
| CN | 108486043 | A | 9/2018 |
| CN | 106085819 | B | 3/2019 |
| CN | 106281991 | B | 5/2019 |
| CN | 109790504 | A | 5/2019 |
| CN | 105189729 | B | 1/2020 |
| EP | 1161208 | A1 | 12/2001 |
| EP | 1664276 | B1 | 11/2013 |
| EP | 3378445 | A1 | 9/2018 |
| EP | 3409369 | A1 | 12/2018 |
| EP | 2945564 | B1 | 5/2019 |
| JP | 2010178695 | A | 8/2010 |
| KR | 101129419 | B1 | 3/2012 |
| WO | 2012/001607 | A1 | 1/2012 |
| WO | 2015/161057 | A1 | 10/2015 |
| WO | 2015/163010 | A1 | 10/2015 |
| WO | 2018/189431 | A1 | 10/2018 |
| WO | 2019/012231 | A1 | 1/2019 |
| WO | 2019/018002 | A1 | 1/2019 |
| WO | 2025240760 | A1 | 11/2025 |

OTHER PUBLICATIONS

Reveille® Cartilage Processor, A cost-effective option for single stage surgery with autologous cartilage, Exactech, Mar. 18, 2020, available at: https://www.exac.com/biologics/reveille/, 3 pages.

Resource Library, Exactech, Mar. 18, 2020, available at: https://www.exac.com/resource-library/?fwp_brand_categories_dropdown=reveille-cartilage-processor, 1 page.

Biologics Main Brochure—713-00-20 Rev C, Exactech, Mar. 18, 2020, available at: https://www.exac.com/product/biologics-main-brochure, 9 pages.

PCT Invitation to Pay Additional Fees with Partial International Search, Application No. PCT/US2020/031286, Jul. 31, 2020, 13 pp.

Written Opinion, PCT Application No. 2021/027387, dated Jul. 9, 2021, 9 pages.

International Search Report, PCT Application No. 2021/027387, dated Jul. 9, 2021, 6 pages.

International Search Report, PCT Application No. 2020/031286, dated Sep. 23, 2020, 7 pages.

Written Opinion, PCT Application No. 2020/031286, dated Sep. 23, 2020, 10 pages.

Canadian Examination Report, CA Application No. 3,138,539, dated Jan. 18, 2022, 3 pages.

International Preliminary Report on Patentability, PCT Application No. 2020/031286, dated Nov. 18, 2021, 11 pages.

Intellectual Property Office of Singapore Written Opinion, Singapore Application No. 11202112159P, dated Sep. 19, 2022, 5 pages.

(56)  References Cited

OTHER PUBLICATIONS

International Preliminary Report on Patentability, PCT Application No. 2021/027387, dated Nov. 17, 2022, 10 pages.
Office Action and Search Report in European Patent Application No. 20727112.3, mailed on Dec. 8, 2023.
Written Opinion, PCT Application No. PCT/US2025/029594, dated Aug. 7, 2025, 5 pages.
International Search Report, PCT Application No. PCT/US2025/029594, dated Aug. 7, 2025, 9 pages.

\* cited by examiner double
beveled
edges

*112* secondary
double
beveled
edges

*112* flexed blade in
compression upon
*122* Shear Plane (SP)   *102* acute cutting angle

*112a*

*SP*

*112*

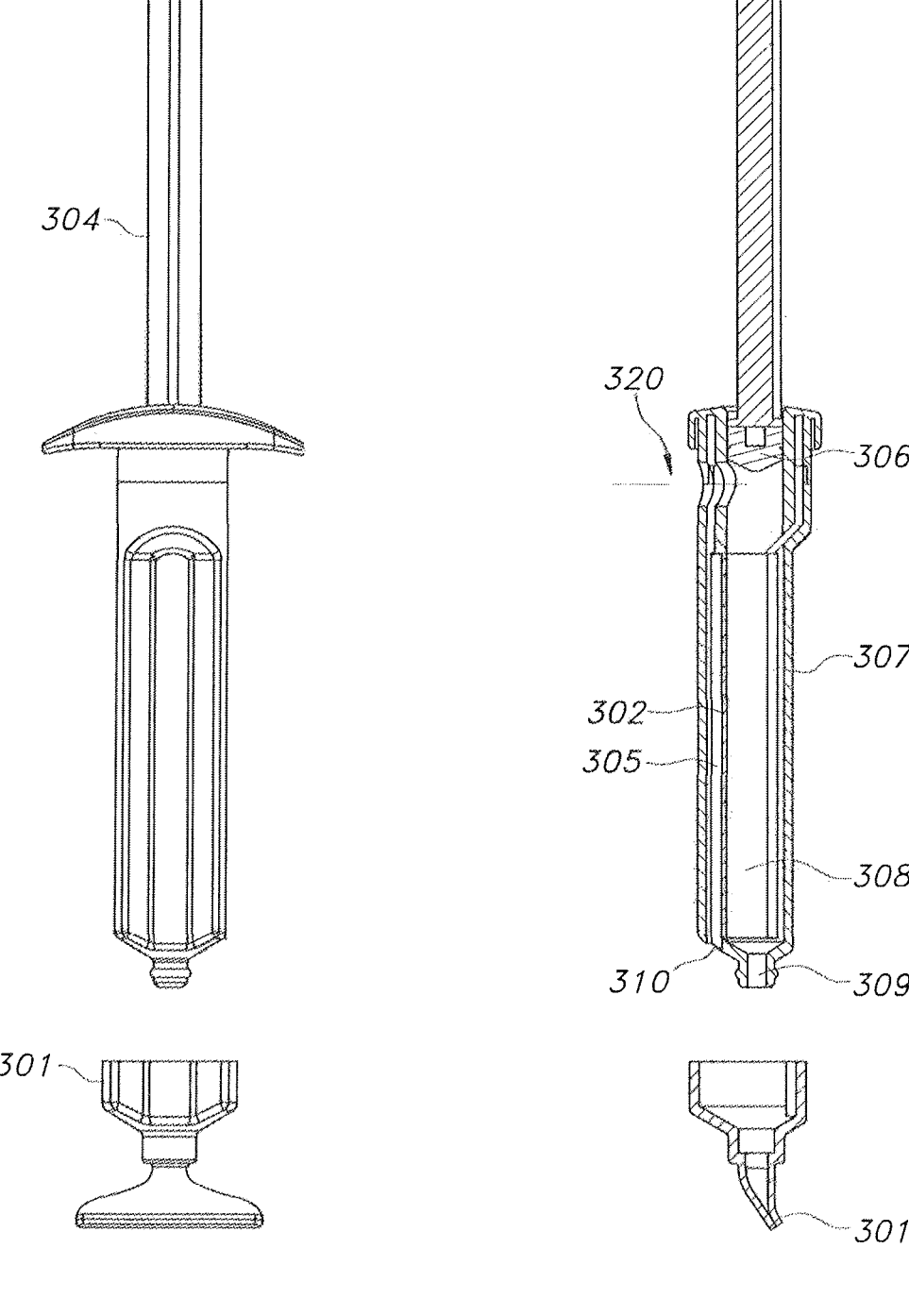
FIG. 15C            FIG. 15D

| Test Date | FIG # | Sample | Total Duration (min) | Total Cells Counted | Quantity of Dead Cells | $(10^6)$ Cells/ml | Viability |
|---|---|---|---|---|---|---|---|
| | 26.1 | 1B | 7 | 73 | 8 | 2.9 | 87.7% |
| 15-Feb | 26.2 | 1C | 7 | 87 | 2 | 3.5 | 97.6% |
| | 27 | 2A | 3 | 53 | 1 | 2.1 | 98.1% |
| | 28.1 | 1B | 4 | 73 | 1 | 2.9 | 98.6% |
| 21-Feb | 28.2 | 1C | 7 | 79 | 6 | 3.2 | 91.8% |
| | 28.3 | 1D | 10 | 77 | 5 | 3.1 | 93.1% |
| Dead Boiled Sample | | | | 9696 | | 3.8 | 0% |

Trypan Blue Viability

957 preparation processing application articular cartilage donor site along non-loadbearing peripheral area Cartilage Graft (CG)

skin graft abdominoplasty suture closed incision no remaining donor site wound left to heal Full Thickness Skin Graft (FTSGs)

paste
~300µ - 200µ injectable
~400µ - 300µ spreadable
~750µ - 400µ split thickness
full thickness
3 - 4 mm interchangeable tips fan tip wiper *981* cannula *983* nozzle *985* needle (18 – 22 ga) *987* applicator device *952* spread *980* paste *982* spray *984* injectable *986*

FIG. 36

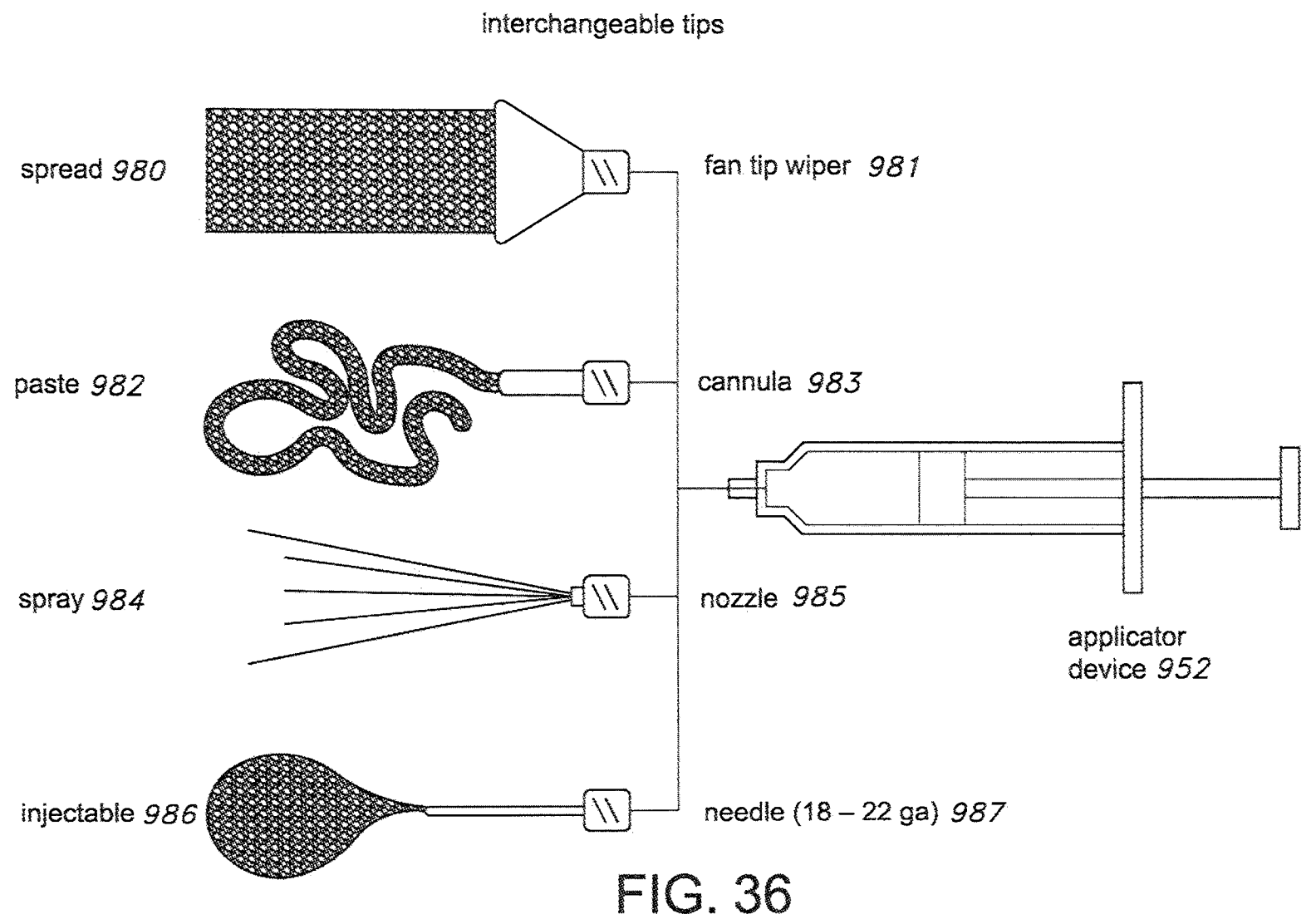

ATRAUMATICALLY FORMED TISSUE COMPOSITIONS, DEVICES AND METHODS OF PREPARATION AND TREATMENT

CROSS REFERENCE TO RELATED APPLICATIONS

This application is a continuation of U.S. patent application Ser. No. 17/236,130, filed Apr. 21, 2021, which is a continuation of U.S. patent application Ser. No. 16/584,755, filed Sep. 26, 2019, which is now U.S. Pat. No. 11,033,295, issued Jun. 15, 2021, which claims priority to U.S. Provisional Patent Application No. 62/843,724 filed on May 6, 2019, and to U.S. Provisional Patent Application No. 62/844,232, filed May 7, 2019, the contents of all of which are incorporated herein by reference in their entirety.

FIELD OF INVENTION

The present invention relates to a process, method, device, and system for preparing atraumatically finely morselized Tissue Particles (TPs) in a liquid medium. The term Tissue Particles (TP) is meant to include tissue harvested from Full Thickness Skin Grafts (FTSGs), Split Skin Grafts (SSGs), Cartilage Grafts (CG), or other organ graft tissues, which is then subjected to the processes described herein to produce small, morselized tissue particles which retain their viability during the process of morselization. The resultant product of this process may be a suspension of the TPs, such as full thickness skin graft or cartilage graft particulates, containing highly viable interconnected tissue cells and extracellular matrix material, in an aqueous suspension, which may be prepared rapidly in a closed aseptic system at bedside, as an office procedure, or in the operating room and delivered conveniently and uniformly to treat a body wound/injury/defect through a syringe or with other controllable application methods. The TP, such as FTSGs, CG suspensions may be used as appropriately indicated in plastic surgery, orthopedic surgery, or other surgical applications, such as wound healing, cosmetic surgery, or joint surgery, among others. The term morselized TPs is meant to refer to the finely cut, highly viable tissue as processed in accordance with the present invention, including various sizes and shapes, for the purposes described herein. In the case of skin the morselized TPs are desirably FTSGs.

BACKGROUND

There are a number of challenges to overcome in processing tissues for graft applications. For the treatment of skin wounds, the most efficacious transplants are full-thickness skin grafts. Full-thickness skin grafts involve the epidermis and the entire dermis as well, allowing for most of the characteristics of the grafted skin to be preserved in the process. However since for transplanting FTSGs, the entire dermal layer needs to be removed, the resulting skin graft donor site will not support regeneration and will need to be sutured closed. Consequently, only small FTSGs can be used by current methods. Nevertheless, the result of FTSGs is a graft that maintains more of the normal characteristics of the skin (notably texture, color and thickness), and is also less likely to contract as it heals. This makes FTSGs the more aesthetically pleasing choice for grafts.

Alternatively, in order to treat larger wound areas, physicians use split-thickness skin grafts (STSG) because the resulting donor sites are able to heal on their own over time with appropriate wound dressings. STSG involve only the epidermis and variable portions of the dermis, leaving behind enough of the dermis for the donor site to heal by re-epithelialization without the need to close the donor site wound with sutures. However, these donor sites are painful and slow to heal and the STSG grafts harvested are often still not sufficiently large to cover large wound areas. STSGs can then be meshed, allowing for smaller sections of tissue to be expanded to effectively cover larger areas. The combination of meshed appearance, varying pigmentation, and thinness makes STSGs less cosmetically appealing than FTSGs. Most STSG procedures must be performed in operating room setting.

A variety of techniques and systems to effectively treat large wounds, improve donor site healing and also enable the procedure to be performed as an outpatient office procedure have been developed for various types for surgical applications.

Some techniques have focused on harvesting only the epidermis, rather than including the split or full thickness dermis. Using only the epidermis, the top outermost layer of skin, as a grafting technique has its applications but provides the most limited grafting effectiveness because it contains none of the structural components or cells of the dermis that are desirable for improved healing.

One such commercially known device for harvesting epidermal tissue is the Cellutome Epidermal Harvesting System, marketed by KCI, an Acelity Company. This system uses a vacuum to create series of epidermal micro-domes on the donor site which are cut by hand using a blade and transferred to the patient using an adhesive pad. This technique can be performed outside of the operating room and provides only forty two small epidermal skin patches which are only suitable for grafting superficial wounds in small areas. Because these epidermal grafts do not contain the structural components or cells of the dermis, these grafts work best on superficial wounds and results in small, superficial donor sites that require healing, albeit faster than donor sites from STSGs.

A recent variation of split thickness skin grafting technique is the Xpansion Micro Auto Grafting Kit, marketed by Acell, Inc. This device consists of disposable instruments designed to be used for the harvesting, mechanical preparation, and application of split-thickness skin autografts for the purpose of transplantation onto wounds. In a commercial setting, this technique involves manually harvesting a small split thickness skin graft with a hand dermatome type device and then further mincing the graft by hand using a series of parallel cutting disk blades, and then spreading the minced pieces over a larger wound area by using a spatula. This process still results in a donor site in need of healing and also presents challenges with need to dislodge the minced tissue from between the stacked parallel roller blades and with the handling and transfer or the small pieces of graft.

A recent variation of full thickness skin grafting technique is described in the US Publications 2016/0310159 and 2016/0310157 as a harvesting device that processes full thickness grafts. This device utilizes rows or arrays of adjacent hollow needle-point tubes, assisted with ultrasonics to core and capture tubular micro-columns of full thickness skin samples from a donor site. The tubular columns of tissue arrays are intended to be scattered over a wound site (graft site). This technique requires a large number of harvested tissue micro-columns, however the device is limited by the finite number of columns achievable with each use. Also, like the Cellutome or Xpansion devices, this device creates an ancillary donor site in need of healing and the resulting tissue form is challenging to spread uniformly over irregular wound sites and is unsuitable for grafting large areas.

Until now, the means to effectively use some grafts for transplantation in surgical applications such as full thickness skin grafts, split thickness skin grafts or cartilage grafts has remained inadequately resolved. The un-solved problems of how-to best process tissues, such as skin grafts or cartilage grafts in an effective manner by known prior art methods and devices, include among others: 1) the inability to harvest a large full thickness skin graft without creating an ancillary wound that is too large thus limiting FTSG, the gold standards for skin grafts, to very small grafts that can be closed with sutures; 2) creation of donor sites that are painful and slow to heal with STSGs; 3) and the inability to achieve a graft tissue forms from skin grafts or cartilage grafts with high cell viability that are easy to process rapidly, manipulate in a closed aseptic system, and to be applied uniformly over wounds with irregular surfaces; and 4) the inability to process full thickness skin grafts in a time and cost effective manner that can be expanded to cover larger areas or processed to treat chronic or contaminated wounds.

SUMMARY OF THE INVENTION

The present disclosure addresses many of the aforementioned issues of live tissue processing. The device and processing methods are specifically designed to process tissue, harvested a-traumatically into particulates in an aqueous suspension with very high cell viability that can be easily dispensed on a wound. Using full thickness skin containing all the skin cell types and skin extracellular matrix, the graft can be harvested from an ancillary site with the ability to completely suture close the donor site during the procedure and then process the tissue to cover an area much larger than the original skin area with a graft containing high viability autologous skin cells. The closed system device and the aqueous environment allows for convenience, ease of transfer, and control of sterility, temperature, and pH, without detrimental loss of viability of the tissue cells in skin or cartilage grafts. The resulting graft form is a liquid or paste form and can be dispensed precisely and uniformly as desired. In the case or cartilage, grafts can be taken from areas of non-articulation processed and grafted into cartilage defects.

The resulting abundance of readily morselized tissue form, in the example of full thickness skin, containing all tissue components of the skin, that is a mixture of viable dermal and subdermal cells and interstitial tissue components, exceeds the capability of other currently available devices and practiced methods.

Thus, in one aspect of the invention there is provided Full Thickness Skin Graft (FTSG) composition comprising a plurality of mechanically separated Full Thickness Skin Graft Particulates (FTSGPs) present in a liquid medium. The composition includes FTSGPs which include full thickness skin cells and extracellular matrix material. The majority of the plurality of skin cells within the FTSGPs are desirably viable after processing, with at least about 50% of the skin cells within FTSGPs viable after processing.

The FTSGPs have an average size as measured across their largest dimension of about 200μ to 1500μ (0.020 mm to 1.50 mm), desirably about 350μ to 1250μ (0.35 mm to 1.25 mm) and more desirably about 500μ to about 1000μ, and even more desirably about 500 to about 750μ or 250μ to 750μ, relative to particular surgical implant applications. The nominal average size of tissue morsels may be controllably varied with duration and/or speed of mechanical processing, as desired for particular surgical implantation purposes. The overall process is capable of being expediently completed to optimally maximize cellular viability of the tissue graft material from the time of harvesting to the time of autologous implantation. The process of morselization may be effectively completed, for example, within three to ten minutes, relative to the type of tissue being processed and the nominal tissue particle sizes desired for a particular surgical application.

The TP, or in the case of skin, FTSGPs, may be formed by atraumatically slicing the FTSG into particulates in a liquid medium using the devices as further described herein. Desirably, the liquid medium may be a hydrophilic medium, but may also be an oleophilic medium. The FTSGPs may be suspended in the liquid medium. The liquid medium itself may be in the form of solution, an emulsion, a suspension and combinations thereof.

The present invention would process tissue that would include all the cell types and extracellular matrix components of the processed tissue. For full thickness skin, this would include all epidermal and dermal cells as well as skin appendage cells and extracellular matrix.

In another aspect of the invention there is included a device for processing organ tissue which includes:

a) a container for accommodating fluid and for receiving said tissue;

b) a pair of cutting devices supported in juxtaposition in a container, at least one of the cutting devices being moveable with respect the other cutting device to slice tissue between thereof; and c) an agitation device which causes repeated flow of fluid and fluid suspended tissue through the juxtaposed cutting devices, with the agitation device capable of moving in concert with at least one moveable cutting devices and repeatedly moving fluid and tissue through the juxtaposed cutting devices repeatedly.

At least one movable cutting device may be adjacent to the other cutting device. The movable cutting device may be mounted to or integrated with the agitation device for movement. One of the juxtaposed cutting devices may be fixed.

The agitation device causes circulating flow of fluid and tissue through the juxtaposed cutting devices. Desirably, the agitation device creates a vortex propulsion movement of fluid and tissue repeatedly through the space between the juxtaposed cutting blades. The agitation device may take a variety of forms, desirably the agitation device includes or is an impeller for causing circulating flow of fluid and tissue repeatedly through the juxtaposed cutting blades. Moreover, it is also desirable that the agitation device and the movable blade be movable in a rotational direction about an axis.

As will be seen from the figures and descriptions, the impeller desirably has a curved surface along said axis for causing continuous circulating movement of liquid and tissue. Moreover, at least one of said cutting devices includes blades radially arrayed with angular spaces between, and desirably the other cutting device includes a plurality of said blades radially arrayed with curved angular spaces between. The angular spaces between the blade edges of the movable cutting device may be different from the angular spaces of the blades of the juxtaposed cutting device. The cutting devices may be in physical contact along a common shear plane.

As described, the container includes an opening for receiving of fluid and tissue and may also include an outlet for the discharge of fluid and processed tissue. The system may also include a dispensing device in fluid communication with the outlet to receive the discharged fluid and the processed tissue. The dispenser may be selected from a variety of devices, including syringes, which are particularly useful because it is an accurate and easy way to dispense the fluid composition containing morselized Tissue Particles or specifically FTSGPs onto a wound area.

As mentioned above, the present disclosure further includes a method for forming processed tissue into particulate form which includes:

providing a container supporting a pair of cutting devices in juxtaposition;

placing fluid and organ tissue into said container;

moving at least one of said cutting devices to cut said organ tissue; and providing an agitation device to continuously move fluid and tissue through the cutting devices to repeatedly slice or cut tissue into progressively smaller particulates.

The method may further include providing a dispensing device in fluid communication with an outlet; and discharging the fluid and tissue into a dispensing device.

In another aspect of the disclosure there is included a plurality of full thickness skin graft particulates (FTSGPs), desirably in an aqueous suspension made by the process which includes:

providing a container supporting a pair of cutting devices in juxtaposition;

placing fluid and tissue into the container;

moving at least one cutting device to cut tissue or in one case FTSG tissue;

and providing an agitation device to continuously move said fluid and said organ tissue through the cutting devices to repeatedly tissue into progressively smaller particulates.

As previously mentioned, in such a product containing a plurality of Tissue Particles (TP) or in one case full thickness skin graft particulates (FTSGPs), desirably the particulates are processed and dispensed in an aqueous suspension, and the majority of the plurality of FTSGPs are viable after processing, desirably at least 50% or more. This high viability is due to a number of factors, including the use of atraumatic slicing by the inventive devices, the use of a liquid, biologically friendly medium, such as a saline or other isotonic compatible medium which can buffer Ph, and prevent desiccation. As previously mentioned, the choice of liquid medium may be one of hydrophilic character, oleophilic character or may have aspects of both, such as an emulsion. The process also does not generate excessive heat and temperature can be controlled such that cells are negatively affected. Although various sizes of morselization are contemplated, in some embodiments, the TP or FTSGPs have an average size as measured across their largest dimension of about 150μ to about 1000μ.

Smaller particle sizes facilitate dispensing through devices such as syringes, which are both familiar to the practitioner and easily manipulated for controlled deposition at the wound site. For example, particles which are nominally smaller than 400μ are useful for delivery through an 18 gauge needle or nominally less than 200μ to be delivered through a 22 gauge needle.

For subdermal implantation through needle injection, the epidermis is removed prior to injection. This can be done through several methods and is a routine surgical procedure. With the epidermis removed only the dermal elements are processed and only the dermal elements without the epidermis can be injected into the dermal or subdermal plane. This overall process is otherwise identical to the processing of other tissue or full thickness skin.

BRIEF DESCRIPTION OF THE DRAWINGS

FIG. 25 is a table showing samples of FTSGPs which were processed according to the invention and exhibited cell viability of 87.7-98.1% during and immediately after the processing using the inventive devices, methods and systems.

FIG. 36 shows dispensing options which may be employed in accordance with the present invention.

DETAILED DESCRIPTION OF THE INVENTION

Figure 1:
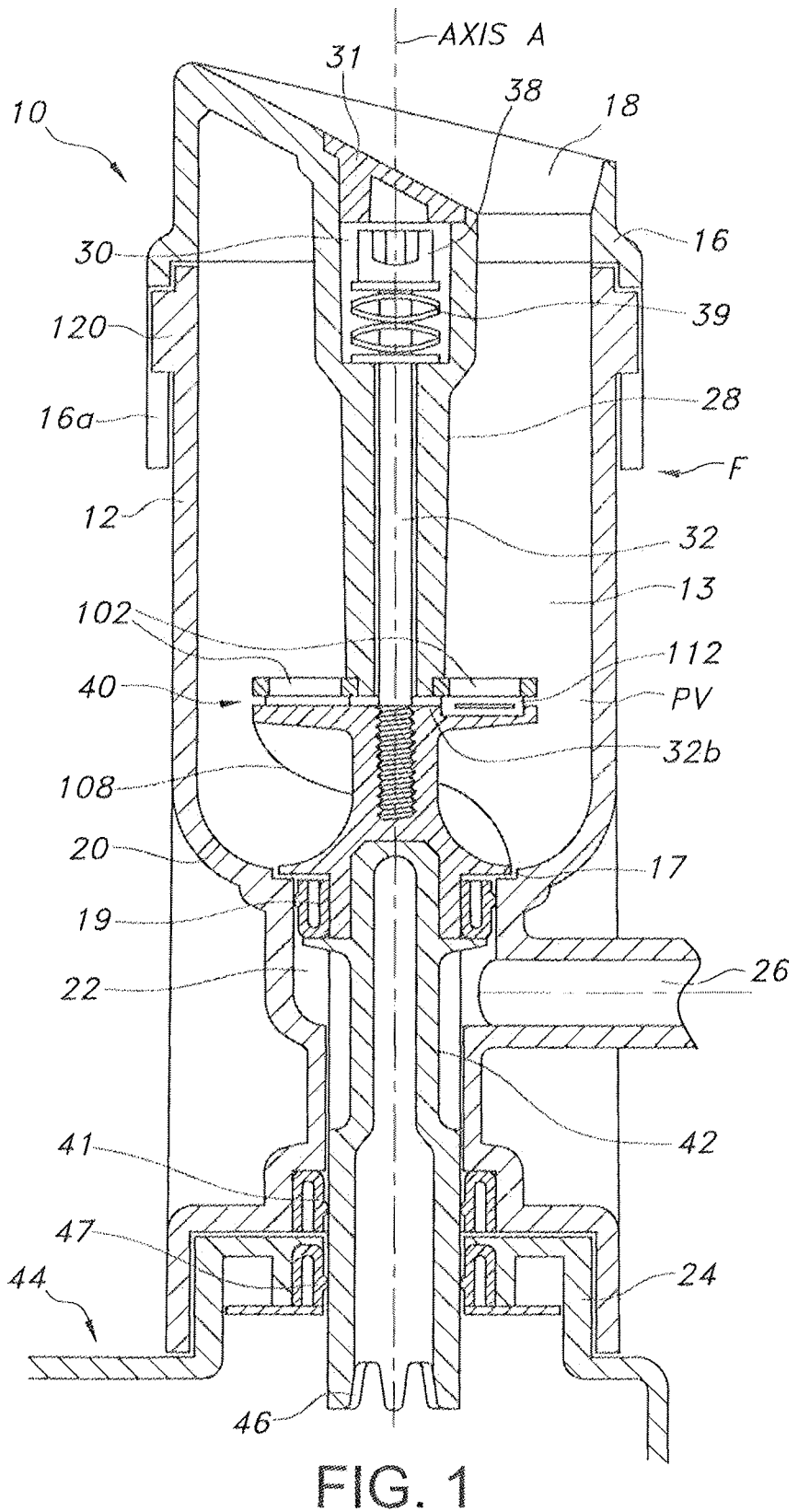
FIGS. 1-4 are sectional views showing of the processing device for morselizing tissue grafts full thickness skin grafts (FTSGs).

The device has features which optimize processing cell viability and convenience of tissue handling and transfer. Specifically, the aqueous processing allows for temperature, pH, and salinity control of the processing which would ideally be variable depending on the tissue, isotonic factors. The pH may be controlled with physiologic buffers. The variable blade speed allows for control of any potential baro-trauma caused by the formation of the vortex, which repeatedly moves the tissue suspended in the aqueous medium through the cutting devices.

The selection of ultra-sharp cutting blades is one important factor in ensuring that the tissue that is morselized remains viable. The use of pH controlled aqueous medium, along with the ability to control the temperature of the medium during processing, as well as, the time, are also important factors in achieving morselization with the exceptionally high degree of viability of the invention.

Mass-produced disposable razor blades and microtome blades are among the sharpest steel blades in the world. Razor type blades are typically martensitic stainless steel with a composition of chromium between 12 and 14.5% and a carbon content of approximately 0.6%. The high-volume linear process to produce such blades, starts with a roll formed strip of controlled thickness that is run as a ribbon through a continuous manufacturing process. The linear manufacturing process enables exceptionally tight and repeatable control of multiple sequenced automated processes including, for example, grinding multiple distinctly stepped beveled/faceted cutting blade edges on both sides; with cutting edges as thin as 30 nm for razor blades and 3 nm for microtome blades; with edges fortified with separate vacuum chamber applied hardened coatings (for example titanium+manmade diamond to harden edge), followed by, for example low friction polymer film for slipperier edge. Individual blades are progressively die-stamped in-line in a repeatable manner.

Blade Sharpness, is absolutely necessary to minimize cell mastication. Use of ultra-sharp blades, passing through and between masses of live cells, and through interstitial spaces, best assures a narrow margin of violated cells along the cut line with the least amount of shear forces and crushing of cells. Slicing of tissue between two blade edges, passing at acute angles, enables stabilization of the tissue throughout each cut to achieve controlled atraumatic slicing of whole thickness skin tissue into morselized particles.

Use of ultra-sharp blades, as achievable through automated processes, assures repeatability and expedites the morselization process, enabling autologous whole thickness skin to be quickly converted into a new morselized implantable tissue particles within minutes.

To maintain cell viability, best practice is to keep the harvested tissue wetted and then suspended in the pH controlled solution throughout handling (i.e. in saline, a buffer solution, or BioLife Solution®, or other cell nurturing/preservation solutions, etc.).

Detailed Description of Devices

One preferred embodiment for morselizing full thickness skin grafts (FTSGs) supported in a sterile fluid is shown generally in FIGS. 1-4.

Processing device 10 includes a liquid-tight container 12 having an open upper end 14 which may be suitably enclosed by a cover 16. The cover 16 has an inlet aperture 18 which allows for insertion of tissue into the fluid. In a preferred embodiment the container is generally cylindrical having a closed curved bottom 20 opposite open upper end 14 with and exit opening 17 therein. While the cover 16 and the container 12 may be made of various materials, in a preferred embodiment, the cover and container are formed of a suitable plastic such as polypropylene (PP), polyethylene (PE), polystyrene (PS), polyethylene terephthalate (PET), polyimide (PA), acrylonitrile butadiene (ABS), polyetheretherketone (PEEK) and polyurethane (PU). Combinations or co-polymers of these polymers may be used.

Glass, ceramic or metal containers may also be used. The container 12 may be transparent to visualize the processing and quality of the fluid and tissue being processed within.

An additional removable or adjoined protective cover that is able to be manually opened and closed may be included so as to close off the cover opening during processing to best assure containment of fluid and cellular contents.

It is also contemplated that all components comprising the overall processing device, including the container and morselizing mechanism, isolation device and applicator will be packaged and bulk sterilized, for single-patient use and disposable. The packaged devices may be irradiated with gamma or e-beam or ethylene-oxide (EtO). Alternatively, the processing device may be sterilizable and reusable.

Extending from bottom 20, container 12 includes a generally elongate tubular conduit 22 in fluid communication with the interior 13 of container 12 through opening 17. The conduit terminates in a container mount 24 at the lower end thereof. Extending outwardly and in fluid communication with conduit 22 is an outlet 26 which in the preferred embodiment shown in FIG. 1 extends at a right angle to conduit 22. The description of the purpose of the conduit 22, the container mount 24 and outlet 26 will described in further detail below.

Cover 16 is movably supported at the open upper end 14 of container 12 for movement along a central axis A. The upper end 14 of container 12 includes, for example, an outwardly directed key 12a which is seated in a slot 16a in adjacent skirt 16b cover 16. The key 12a is movable along axis A within the slot 160 to allow for the movement of the cover 16 with respect to the container 12, while restricting cover 16 rotation about axis A.

The cover 16 further includes an inwardly formed downwardly extending generally tubular stem 28 having an upper cup-shape cavity 30 covered by a cap 31. The stem 28 accommodates a mounting rod 32 having a threaded lower end 34 and an upper end 36 terminating in an enlarged head 38. The head 38 is captively retained within the cavity 30 supported by a spring 39, for example by one or more Belleville, dome, single or multiple wave type washers, captive between the lower end of cavity 30 and the enlarged head 38. The spring or springs 39 may additionally be captively sandwiched between conventional type washers 39b, the threaded lower end 34 of rod 32 is threaded into impeller 108 about axis A. A shoulder 32b, adjacent to threaded end 34 of rod 32, is supported against impeller 108.

A disk shaped stationary cutting member 102 is supported upon the terminus of stem 28 on a perpendicular plain relative to axis A. The stationary cutting member 102 is constrained from rotating about axis A by, for example, mating pins 28a or other keyed features in engagement between the stem 28 and the stationary cutting member 102.

Now as best shown by FIGS. 1-4 and FIGS. 9-10, the sub-assembled rod 32, head 38, impeller 108, and blades 112 are together captured and configured to rotate about axis A relative to stem 28. The spring or springs 39, between head 38 and the lower end of cavity 30, act to lift head 38 and thereby lift stem 28 and impeller 108 through stem 38 to continuously constrain rotating blade edges 112a in compression against stationary cutting member 102.

Referring particularly to FIGS. 5-11B, the subassembly of rotating impeller 108 with associated rotating blades 112, held compressively against stationary cutting member 102, about axis A by means of a rod 32 with head 38 and lower end 34 and spring 39 through stem 28 are collectively referred to as a morselizing mechanism.

As described in further detail below the drive shaft 42 is attached to an operatable processor 44 shown schematically in FIG. 1 by way of a drive engagement 46 at the lower end of drive shaft 42. The processor 44 causes rotation of the drive shaft 42 and thereby rotation of the rotating blades 112 against the stationary blade edges 122 within the morselizing mechanism 40 which causes morselization of the tissue, or specifically FTSGs within in the container 12. A suitable rotary shaft seals 47 and 41 provide a fluid seal between drive engagement 46 and drive shaft 42.

The processor 44 is preferably a reusable device that is configured for ease of being aseptically cleaned following each use. The processor 44 is also configured to replaceably receive a processing device 10 in mechanical engagement in such manner that enables a user to attach, use, and remove the processing device using standard practices for interfacing surgical devices in a sterile field. The processor 44 may also be configured to receive a sterile drape to isolate surfaces not shrouded by a coupled processing device. The processor may also be a device that is entirely sterilizable and/or powered by compressed air that is easily available in the operation room setting.

Figure 2:
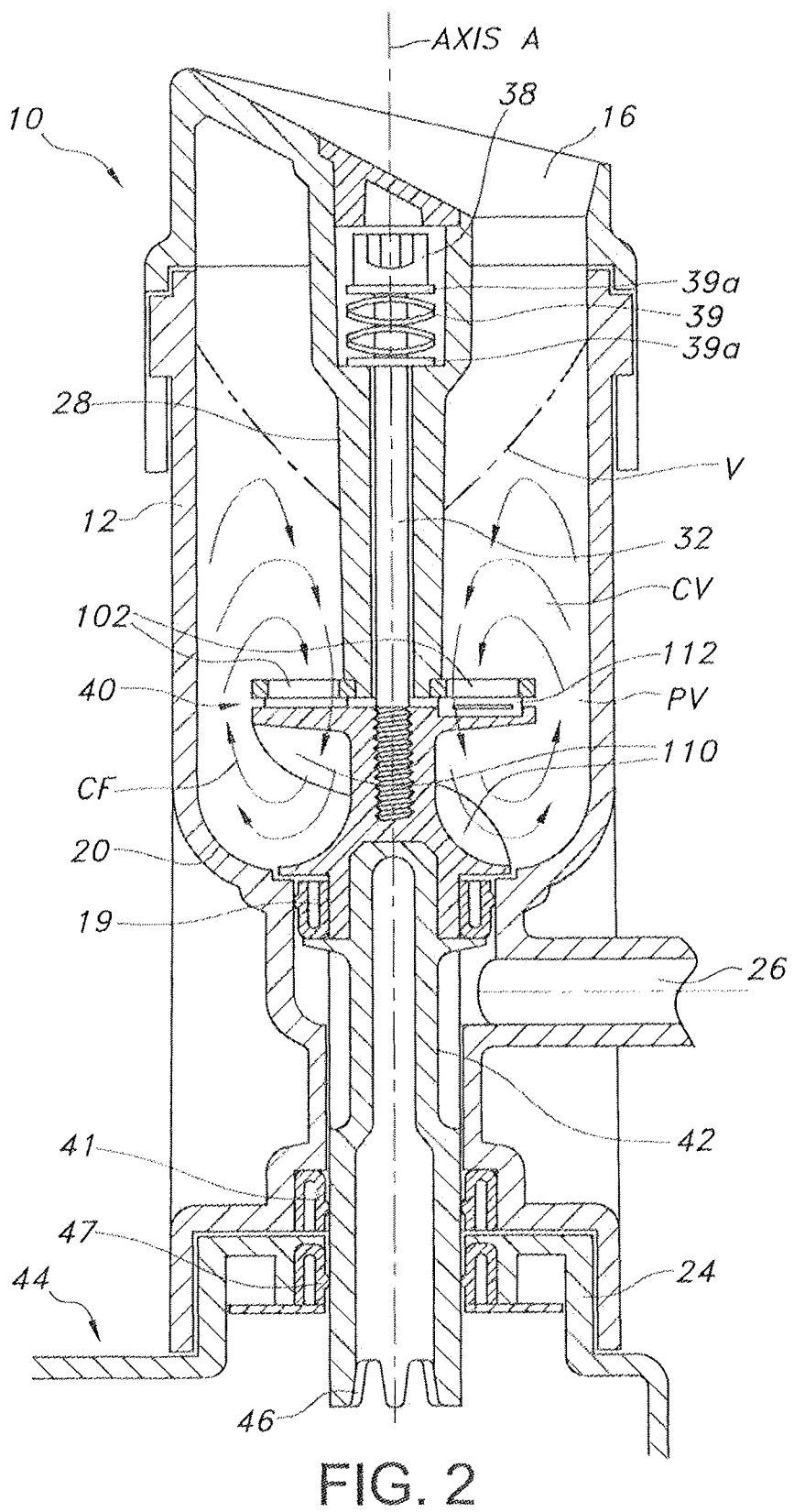

As shown in FIG. 2, and described in more detail below, rotation of the impeller 108 provides a continuous circulating flow (CF) of the fluid and contained tissue or specifically FTSGs about the interior of container 12 and through the morselizing mechanism 40 so as to continually cut the FTSGs into progressively smaller particles. The morselizing mechanism 40 is seated in fluid-tight relationship over exit opening 17 in the open bottom 20 of container 12 to maintain the FTSGs and fluid within the interior of container 12 throughout morselization. A suitable seal 19 provides a fluid seal between morselizing mechanism 40 and exit opening 17.

Figure 3:
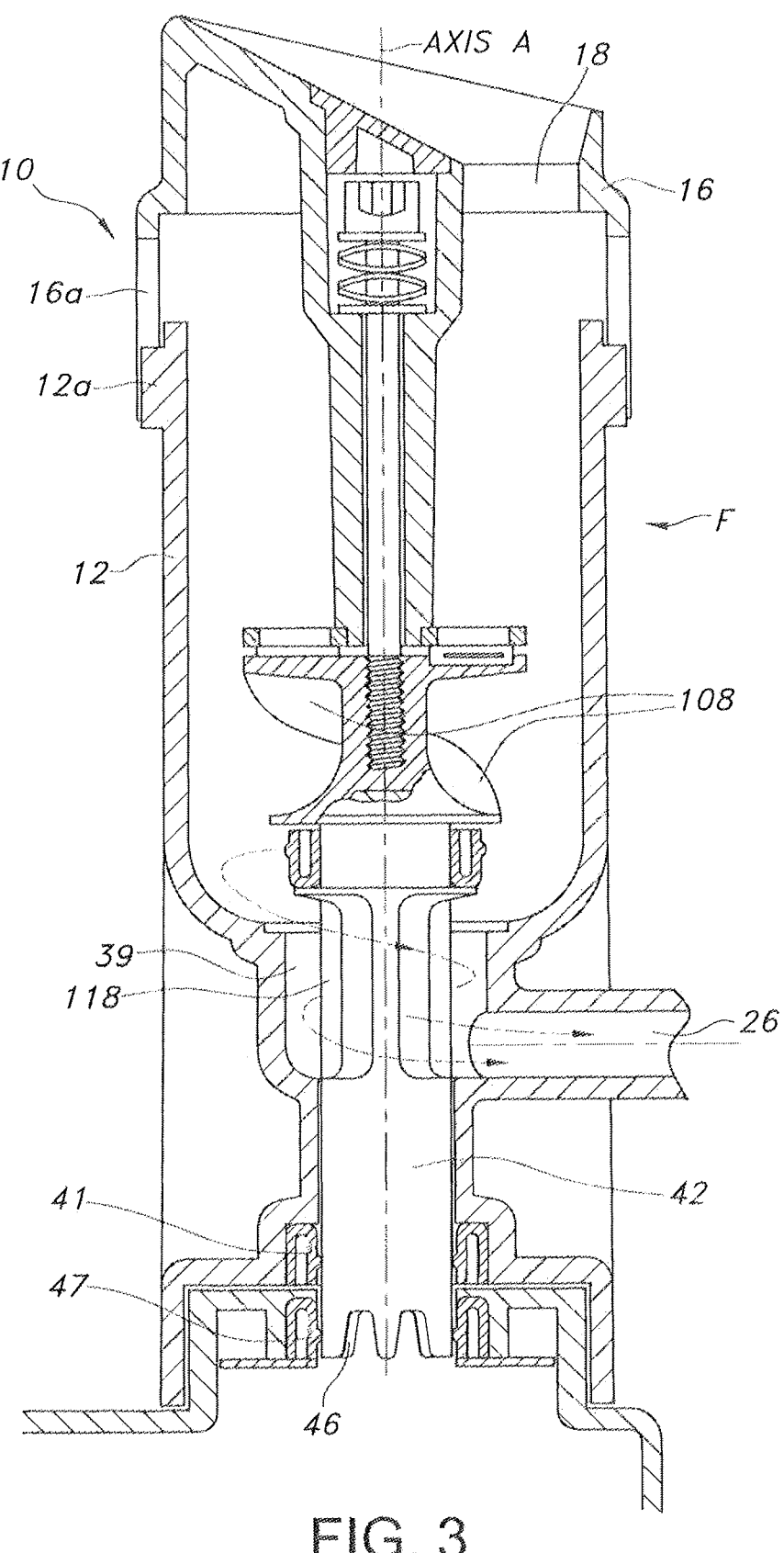
Figure 4:
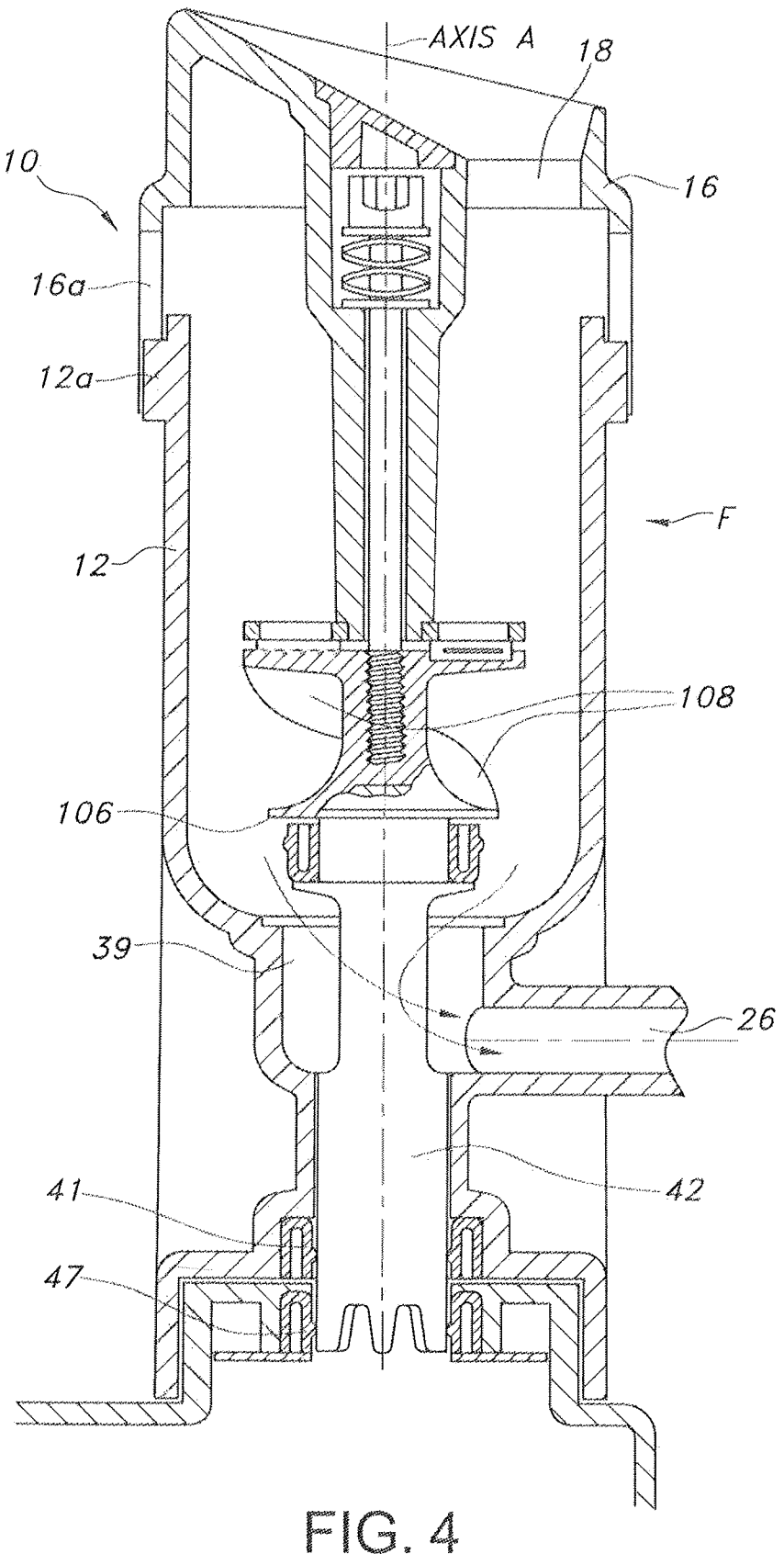

As is shown in FIGS. 3 and 4, the drive shaft 42 may be raised so as to unseat the morselizing mechanism 40 from opening 17 in the open bottom 20 of container 12. Upward movement of drive shaft 42 along axis A causes upward movement of the cover 16 with respect to the container 12 with the key 12a riding within slot 16a. This lifts morselizing mechanism 40 off of its sealed position on the bottom 20 of container 12 thereby rendering accessible exit opening 17 for fluid flow.

Morselizing Mechanism

Operative components of morselizing mechanism 40 are shown in further detail with additional reference to FIGS. 5-8.

Morselizing mechanism 40 includes a base component 100 and a stationary cutting member 102 which are axially aligned over one another along axis A. Base component 100 is mounted to the drive shaft 42 with a depending mount 104 to provide for rotation. Above mount 104 is a flat circular plate 106 which is generally transverse. Plate 106 also serves as the seating surface in opening 17 of the bottom 20 of container 12 as is shown in FIGS. 1-4.

The upper end of base component 100 serves as an impeller 108 having two or more impeller vanes 110 upwardly extending from plate 106 on diametrically opposed sides of axis A. The impeller vanes 110 are each curved along axis A in a complimentary fashion for purposes that will be described in further detail below. Each impeller vane 110 supports in facing relationship at the upper end a cutting blade 112. As also will be described in further detail below, the cutting blades 112 at the upper ends of impeller vanes 110 are supported in juxtaposition with the stationary cutting member 102. The blades 112 rotate with base component 100 with respect to stationary cutting member 102.

In a preferred embodiment shown in FIGS. 5-8, the stationary cutting member 102 has generally disc shaped body 102*a*. The body 102*a* defines spaced apart blade surfaces 120 arranged circumferentially. Each blade surface 120 includes a pair of converging blade edges 122 which converge at an apex 122*a*. In between each of the blade surfaces, breaches 124 are defined. The breaches 124 are open spaces between the blade surface which permits passage of the TPs, such as FTSGs and other TPs, and fluid through body 102*a* as the base component 100 rotates.

Figure 7:
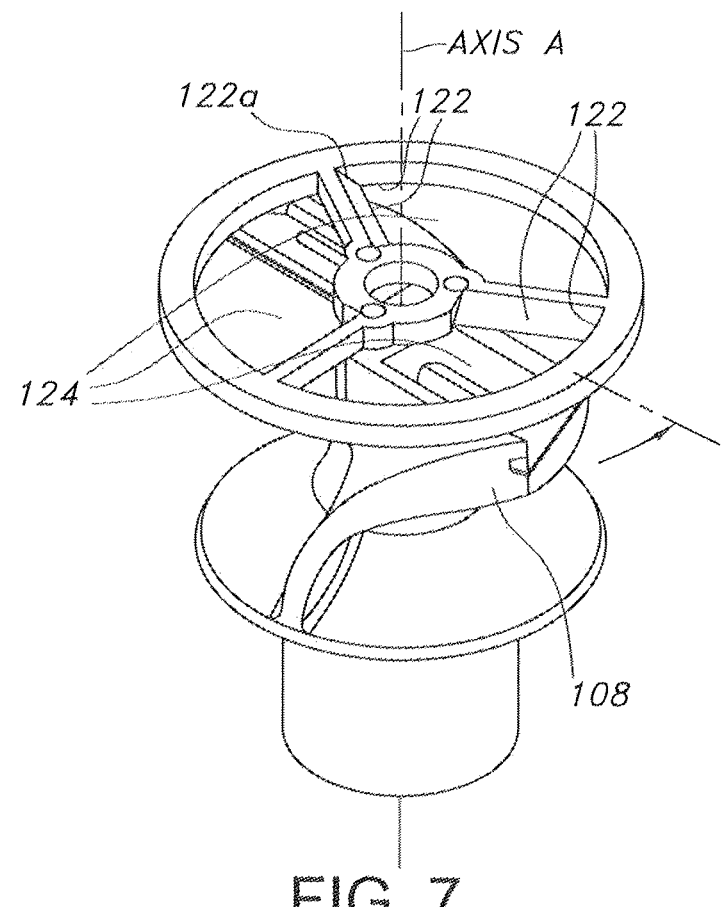
Figure 8:
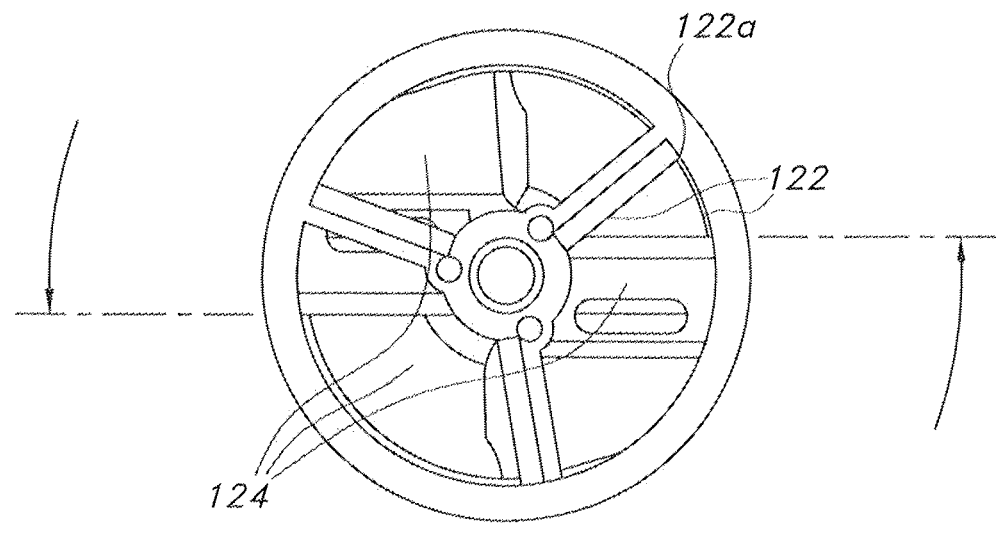

In one embodiment shown in FIGS. 7 and 8, the stationary blade edges 122 are defined by longitudinal radially extending members 123 converging with an arc of the circle forming the outer edge of the disc shaped body 102*a*.

Figure 5:
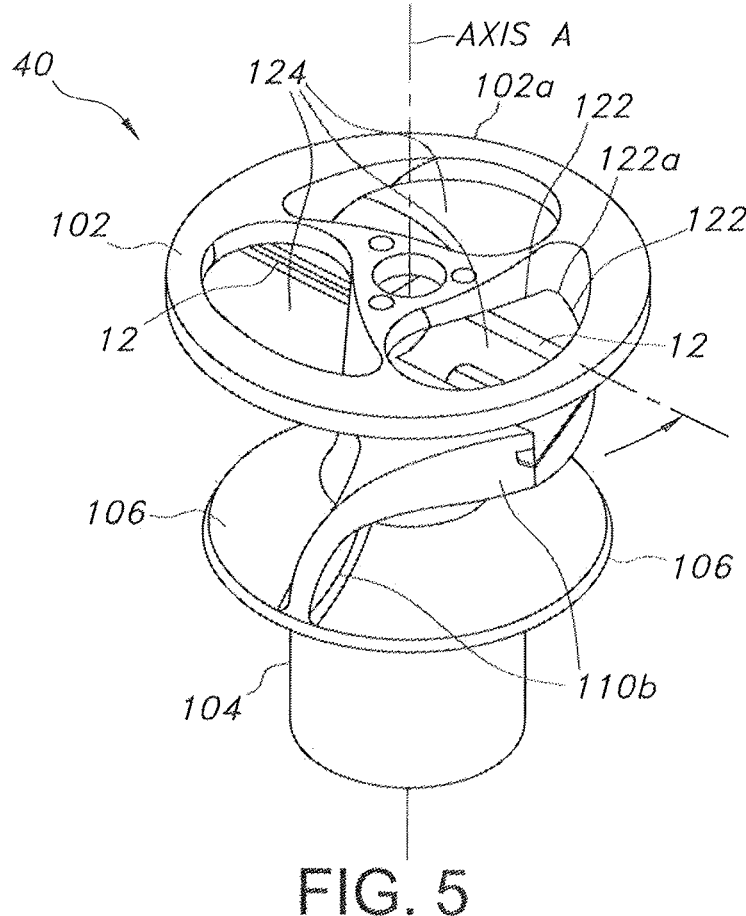
FIGS. 5-8 show in schematic detail the morselizing mechanism of the processing device of FIGS. 1-4.
Figure 6:
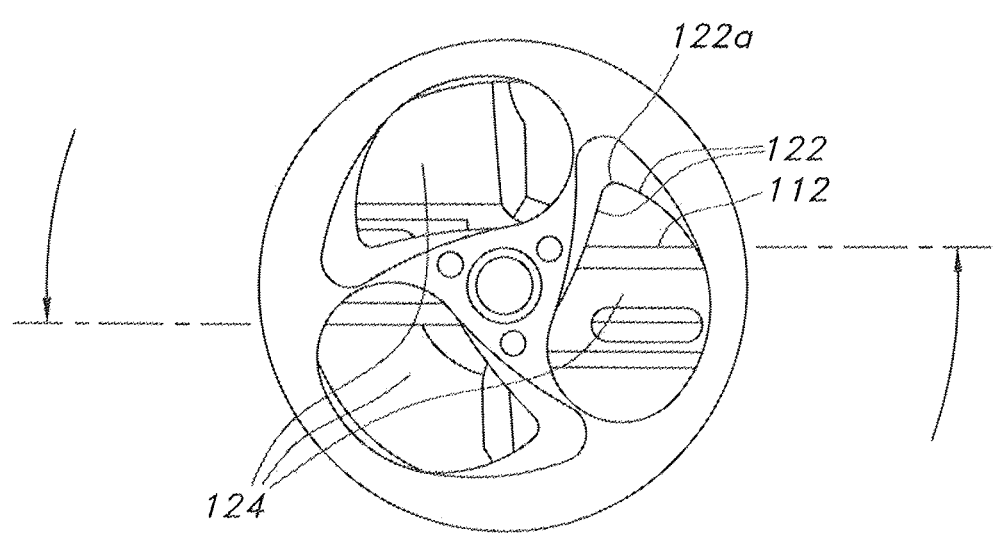

In a more preferred embodiment shown in FIGS. 5 and 6, the blade surfaces 120 are formed in a tear drop shape where the apex 122*a* of the converging blade surfaces 120 converge near the circumference of the stationary cutting member 102 in a tapered curved surface. It has been found that this shape helps promote complete morselization of the tissue and specifically TPs passed through.

The arrangement of the stationary cutting member 102 with respect to the impeller 108 is shown schematically in FIGS. 9-12. A small clearance space (S) is provided between the lower edge of the stationary cutting member 102 and the upper end of impeller 108 such that the extending rotating cutting blades 112 are supported in juxtaposition against the lower edge of the disc shaped body 102*a* of stationary cutting member 102. This creates a shear plane (SP) at which the tissue is sheared and morselized.

The stationary cutting member 102 is preferably stainless steel and CNC machined with precision ground sharp burr free stationary blade edges 122. The bottom shearing plane (SP) surface must be flat and preferably 0.08 μm or better finish. The stainless steel material should generally be a corrosion resistant and hardened grade, for example 440C stainless steel, machined in annealed state and vacuum heat treated to 55-60 RC to achieve a hardened surface and durable sustainable cutting edges.

The rotating cutting blades 112 may be mounted at the upper end of the impeller 108 supported by a spring such as an elastomeric pad 130 which biases the edge of the cutting blade 112 against the lower edge of the disc shaped body 102*a* of stationary cutting member 102. It has been found that maintaining the cutting blade edges 112*a* in physical contact against the stationary cutting member 102, minimizes tearing and shredding of the tissue.

Referring to FIGS. 5 and 6, the stationary cutting member 102 may have two or more breaches 124 radially arrayed about axis A, preferably as shown three, each with associated blade edges 122. The rotating base component 100 may similarly have two or more cutting blades 112 radially arrayed about axis A, preferably as shown two. However, the quantity of rotating blades 112 best differ from the quantity of stationary blades 122, so as to maximize cutting efficiency by minimizing otherwise cumulative cutting forces as would be compounded should multiple blades engage simultaneously.

The rotating cutting blades 112 are positioned at an acute cutting angle relative to the juxtaposed stationary blade edges 122, such that tissue, when captured between the rotating blades 112 and juxtaposed stationary blades 122 will be cut with a slicing action.

Figure 12A:
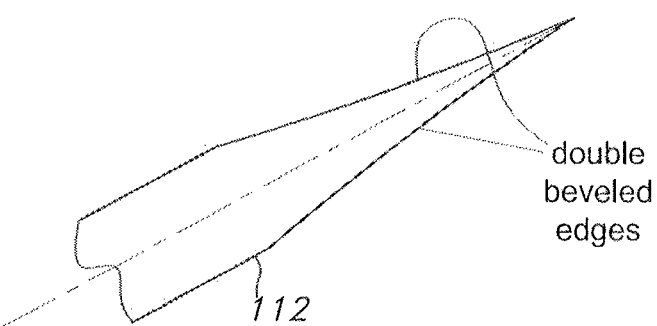
FIGS. 12A and 12B show various configurations for the blade edges and 12C shows the relationship of the blades to a shear plane of the morselizing mechanism of the present invention.
Figure 12B:
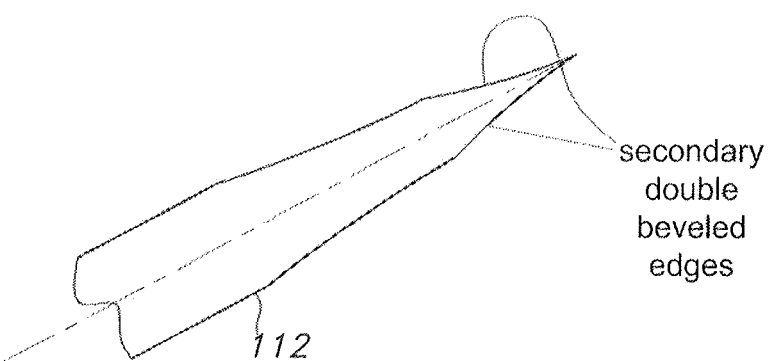
Figure 12C:
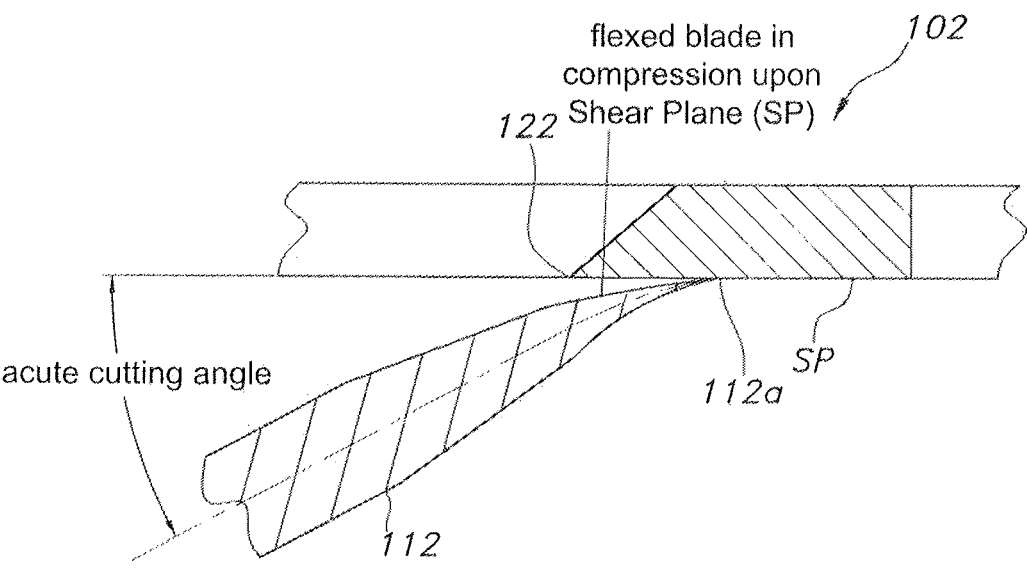

FIG. 12A shows that cutting edges 112*a* of the rotating blades 112 may be manufactured with a ground double beveled edge. Double bevel refers to beveled on both sides of the blade. Alternatively, as shown in FIGS. 12B and 12C, the cutting edges 112*a* can be made sharper with a secondary distal honed double beveled edge which further maximizes the morselization of the TFSGs. Honing refers to a more precise abrasive grinding or lapping process in which a relatively smaller amount of material is removed from the surface by means of a finer grit abrasive. The cutting blades 112 used in our functional proof-of-principle systems utilize preferably further sharpened blades which have a secondary honed double beveled edge, as well as an additional finely honed double beveled edge, for example three graduated sets of double beveled edges.

The rotating cutting blade 112 is best arranged at an acute angle relative to the lower surface of the stationary cutting member 102, so that the tip of rotating blade cutting edge 112*a* passes at an acute angle with respect to the stationary blade edges 122 of blade surfaces 120.

Figure 9:
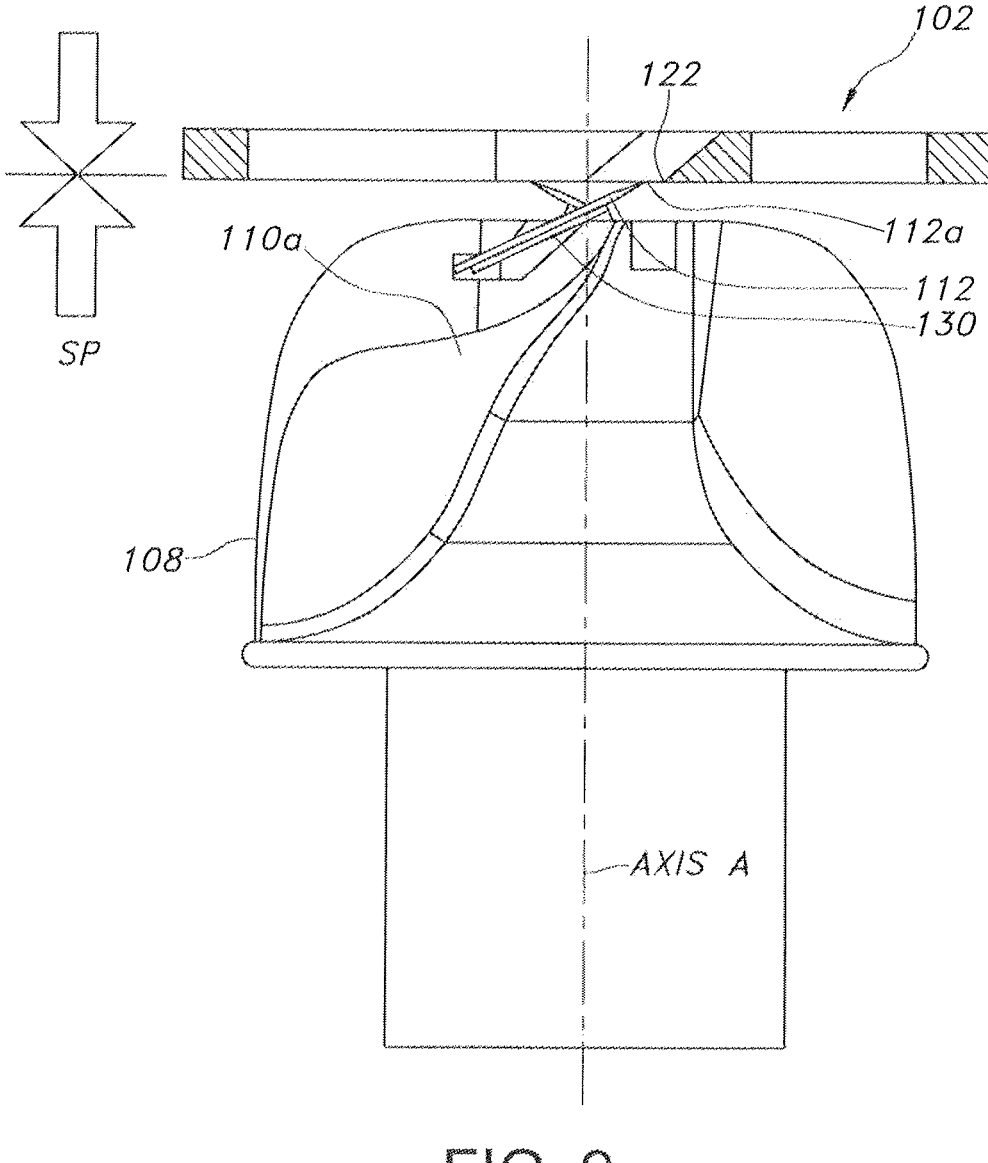
FIGS. 9 and 10 show in further detail the morselizing mechanism of the present invention.
Figure 10:
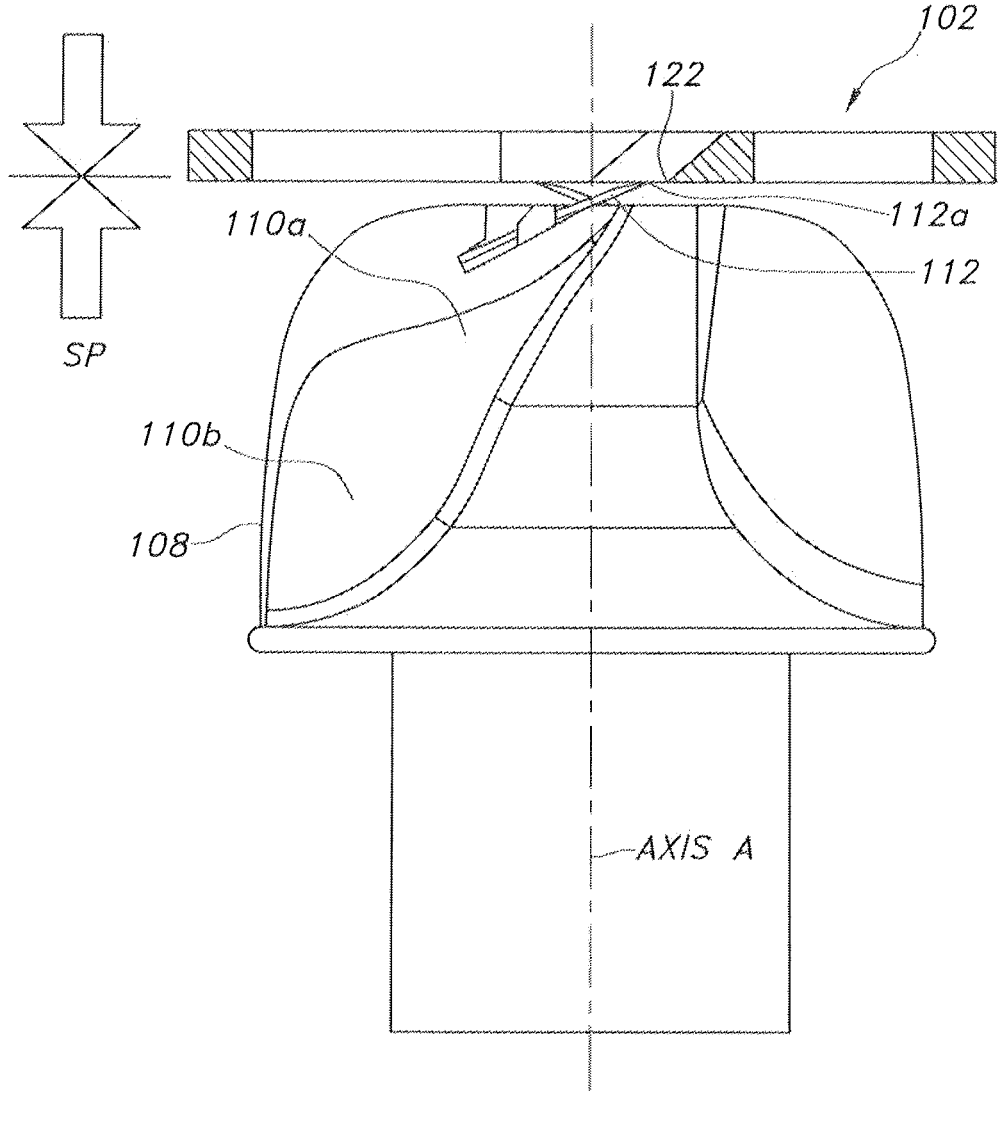
Figures 11A, 11B:
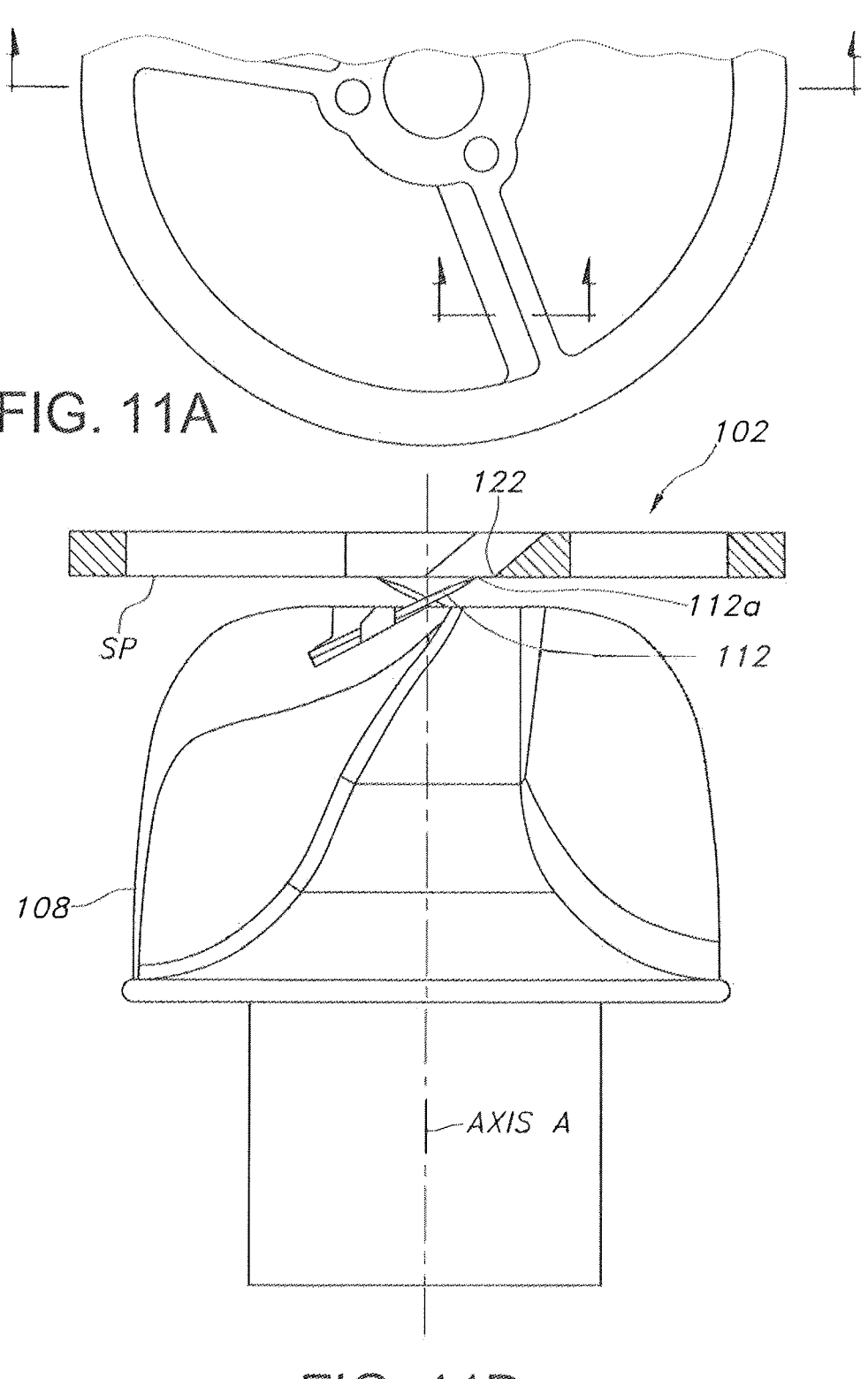
FIG. 11A is a partial top view of a portion of the morseling mechanism of FIGS. 9 and 10.
FIG. 11B is a side view, partially in section, of the morseling mechanism of FIGS. 9 and 10.

As previously described above, springs 39 may be used to compressively pre-load the rotating blade edges 112*a* to maintain contact upon stationary blade edges 122 throughout rotation. FIG. 12C shows that the cutting edge 112*a* of the rotating blades may flexibly conform under preload against the shear plane (SP), particularly when the cutting blade 112 may be substantially stiff, for example approximately 0.010 inch thick. Additionally or alternatively, as shown in FIG. 9, the cutting blade 112, itself, may flexibly conform under preload against the shear plane (SP), particularly when the cutting blade 112 may be substantially flexible, for example approximately 0.003 to 0.006 inch thick.

Figure 13A:
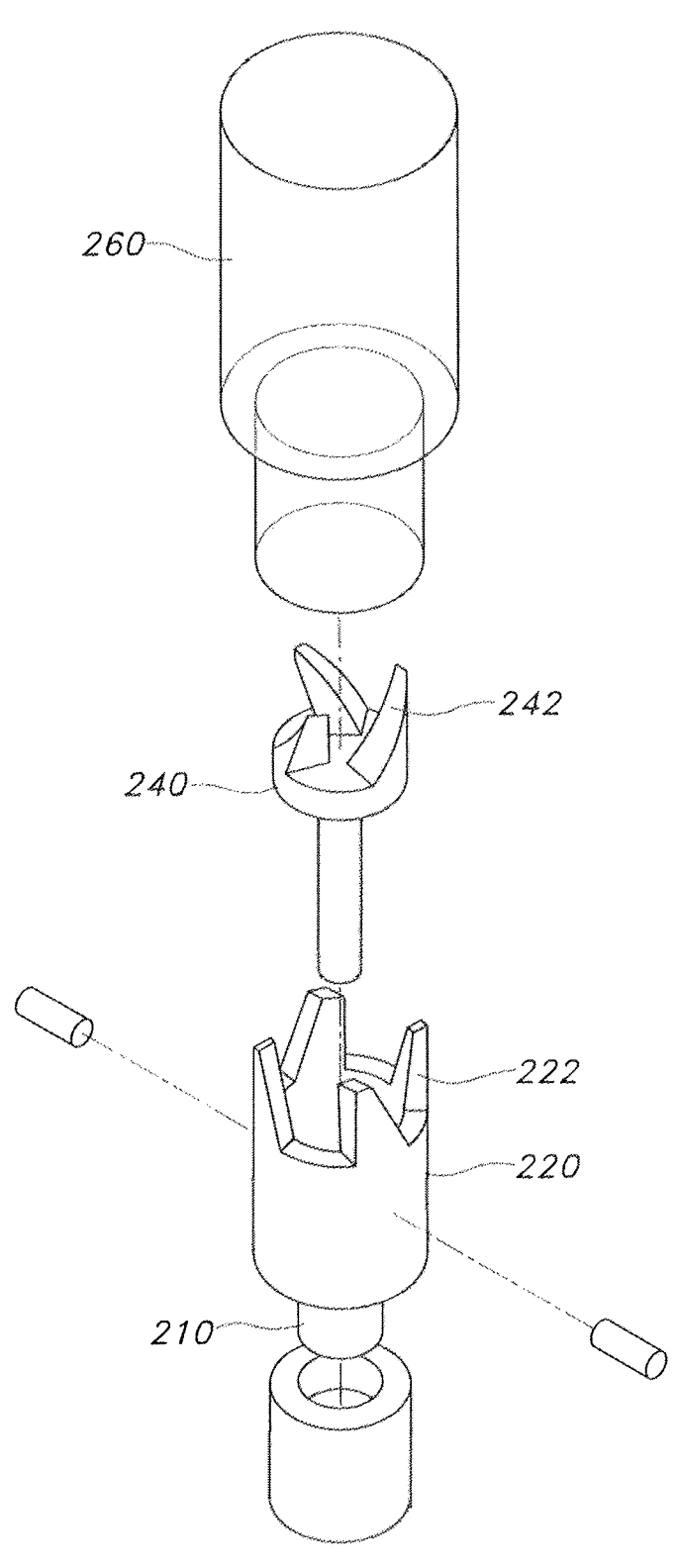
FIGS. 13A-13C show an alternate arrangement of the cutting blades of the morselizing mechanism of the present invention.
Figure 13B:
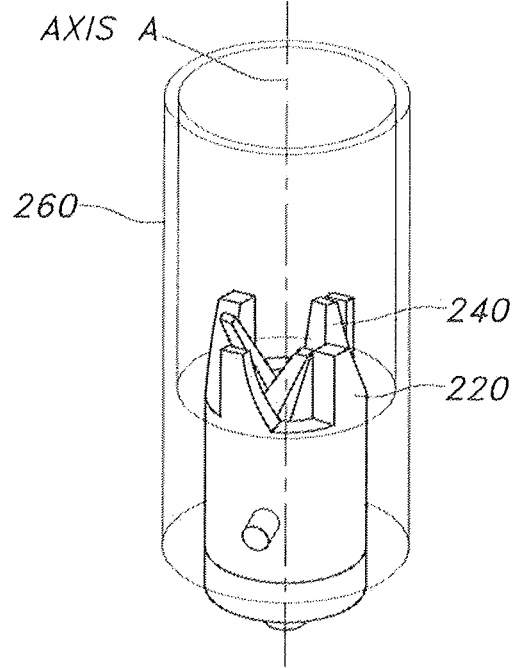
Figure 13C:
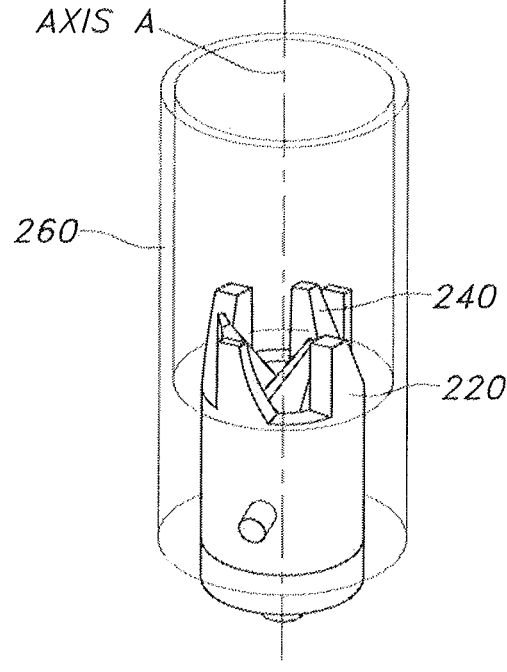

While in a preferred embodiment, the shear plane (SP) is normal to the chamber impeller and blade rotation access. The shear plane (SP) may also take other direction with respect to the axis A. One example is shown in FIG. 13A which shows a bushing 200, a rotatory seal 210, a stator 220, a rotor 240 and a cutting chamber 260. The blades 242 of rotor 240 pass in close proximity to the blades 222 of stator 220 which are stationary blades about a central axis A.

Also, in this embodiment, the rotor blades 242 have surfaces which are configured as integrally formed impeller vanes. The rotating edges may be generally co-extensive to the leading impeller vane edges. The rotating rotor blades and stationary stator blade edges should preferably remain in intimate physical contact to best achieve precise slicing. The blades may be machine honed for closely controlled minimum shear gap, preferably less than 30 micrometers. Positioning the rotating blade edges at an acute angle relative to the shear plane of stationary cutting blade edges facilitates a shear cut for the impinged tissue. Maintaining a spring assisted compressive engagement between the rotating blade edges and the shear plane of the opposing blade edges best assures that tissue will be precisely slice, rather than to slip between the converging blade edges.

Other techniques and arrangements for cutting the tissue at a shear plane may also be within the contemplation of one skilled in the art.

Tissue Morselization

Having described the basic components of the process device 10 of the present invention, one preferred example of the morselization of tissue or specifically TPs as defined herein will be described with respect to the Figures.

Initially, with reference to FIGS. 1-4, FTSGs prepared as above described and in a fluid medium may be inserted into container 12 through inlet aperture 18 of cover 16. A fill line F may be provided so to provide guidance as to the volume of tissue and fluid which may be placed in container 12. Thereafter, the rotating mechanism connected to drive engagement 46 is activated so as to cause rotation of drive shaft 42 and morselizing mechanism 40.

Referring to FIG. 2, such rotation causes circulating flow of the tissue in the fluid by establishing a vortex within container 12. This vortex provides for continually moving the tissue through the morselizing mechanism so as to fully morselize the tissue contained therein. The circulating flow path as well as the vortex established is created by the configuration of the impeller vanes 110 of the impeller 108.

Figure 14:
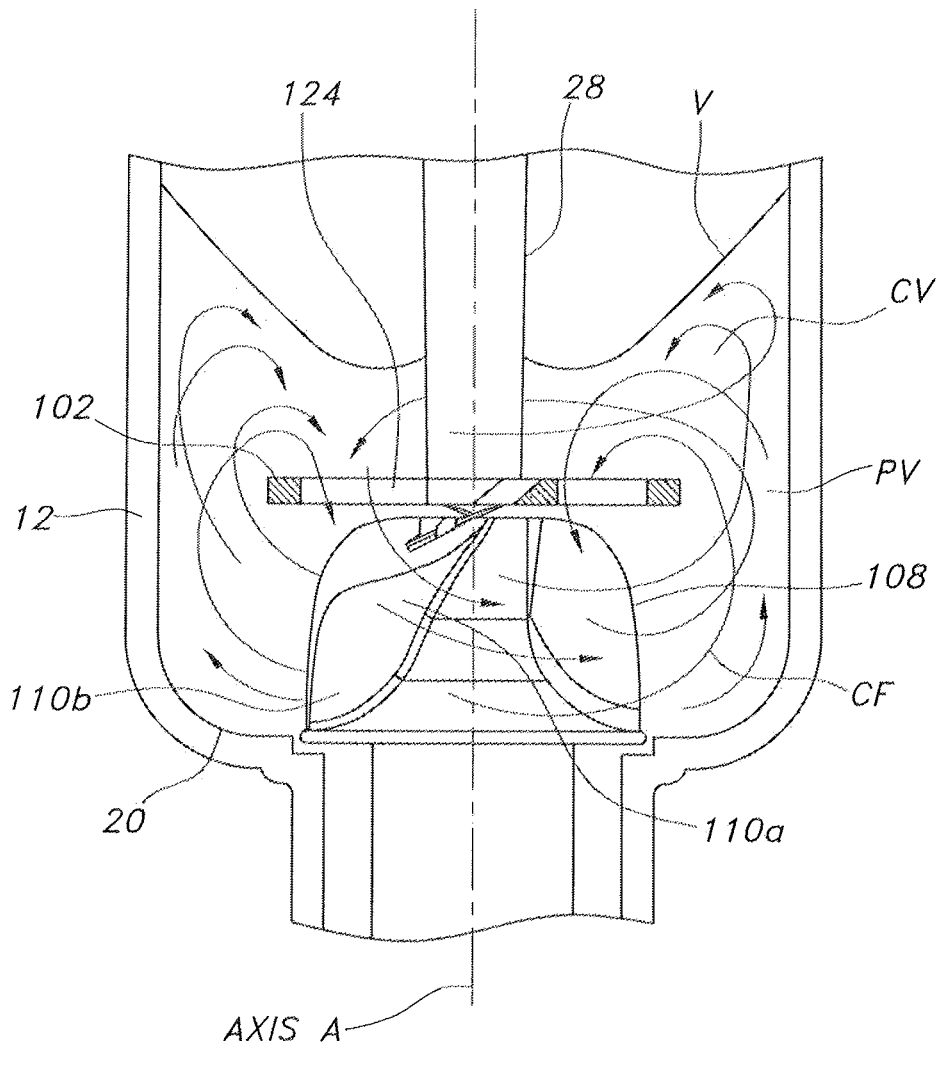
FIG. 14 is a schematic representation of a recirculating flow path created using the morselizing mechanism of the present invention.

Shown schematically in FIG. 14, the impeller vanes 110 are constructed so that an upper or leading portion 110a of the impeller vane 110 imparts an axial thrust upon the fluid and contained tissue or specifically FTSGs, while a lower or terminal portion 110b of the impeller vane 110 provides for radial thrust. The construction of the impeller vanes 110a and 110b provide for continually moving the FTSGs throughout the container 12. The impeller 108 causes fluid with contained FTSGPs to be driven through breaches 124 in the stationary cutting member 102, passing between rotating blades 112 and stationary blades 122, to then be deflected against the trough-like bottom 20 and side walls of container 12 to reverse the flow in the opposite direction, circulating through the outer peripheral volume (PV). The fluid flow then transitions into a vortex to mix and drive the tissue through the central volume (CV) to return again through the morselizing mechanism 40 so that the FTSGs are continually and repeatedly cut and morselized.

A person of ordinary skill in the art will be able to alternatively configure, for example, impeller vanes and/or internal container geometry and/or bottom 20 forms so as to enhance effective circulating flow of fluid with suspended tissue though-out the container 12 and through the morselizing mechanism 40. Internal flow characteristics may be enhanced, for example, by increasing or decreasing the pitch or otherwise reshaping the form of impeller vanes 110; or by increasing or decreasing the pitch of a portion of a vane configured for axial thrust 110a relative to the pitch of a portion of a vane configured for radial thrust 110b; or to eliminate either of the axial thrusting vane surfaces or radial thrusting vane surfaces.

Referring to FIGS. 3 and 4, once the TPs, such as FTSGs and other tissue particles as described herein, are fully morselized, the drive shaft 42 may be raised, unseating the impeller 108 from its seated position in the container. The plate 106 is unseated from opening 17 establishing fluid communication with conduit 22 and outlet 26. The morselized tissue is discharged by a gravity driven drain through outlet 26 for use in a manner which will be described hereinbelow.

Upon completing the morselization of FTSG or other tissues grafts into TPs, the impeller 108 rotation may be stopped and the TPs, as defined herein, having a specific gravity greater than water, will settle to the bottom 20 of container 12. One skilled in the art will recognize that alternative methods may be used to manually withdraw the settled TPs from the bottom 20 of container 12 within the processing device 10. For example, the settled TPs may be drawn into a conventional syringe in combination with an elongated cannulated tip (not shown) that can be inserted into the container 12 through the inlet aperture 18. In such manner, the same syringe used to draw the TPs from the processor 10 could then be used as an application device. In this manner of manually drawing out the TPs through the inlet aperture 18, the processing device 10 need not include a drain 39 or an outlet 26.

Discharge of Morselized FTSGPs

Figure 15A:
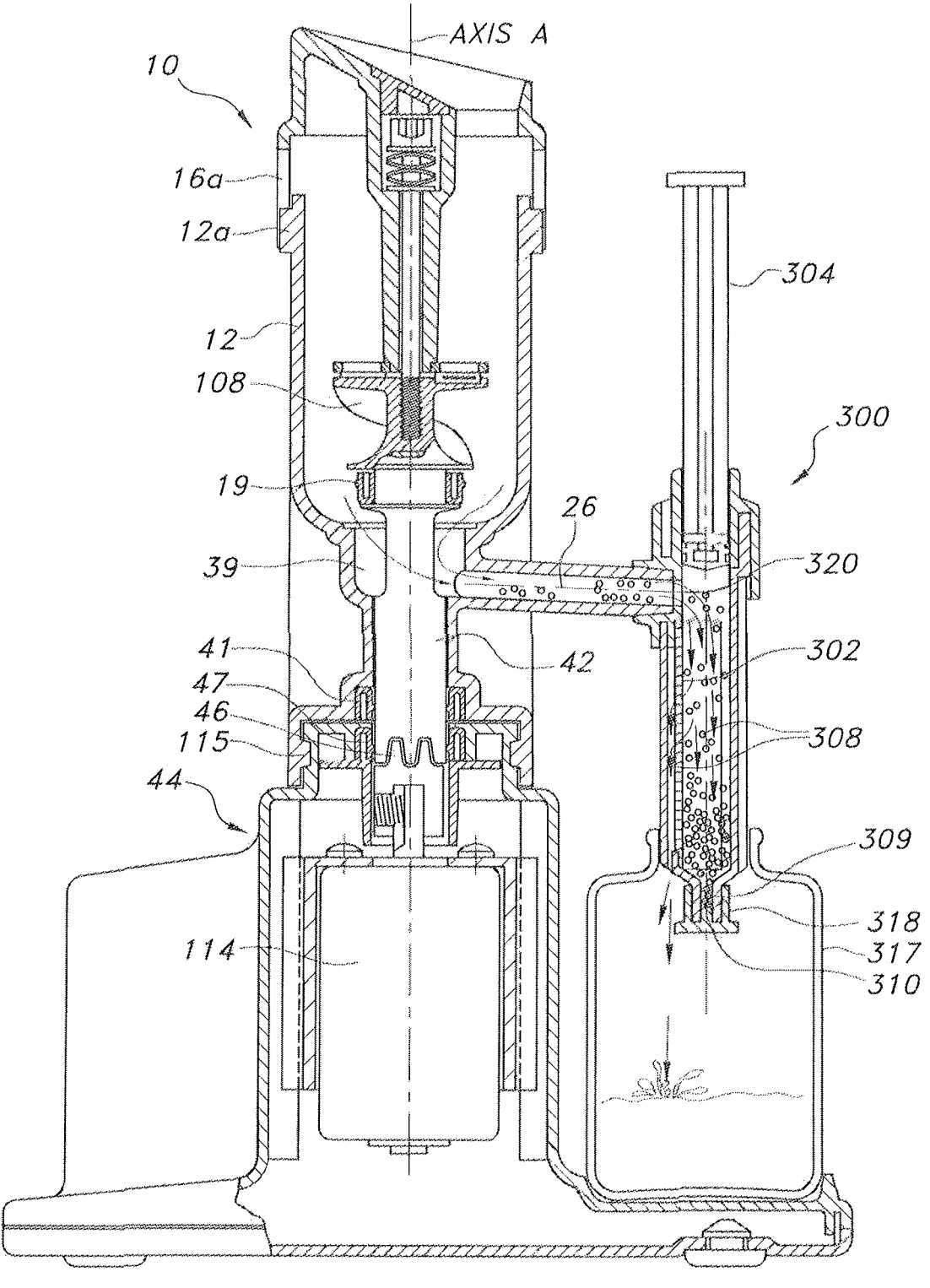
FIG. 15A is a sectional showing of the processing device of FIGS. 1-4 attached to a preferred embodiment of an applicator.
Figure 15B:
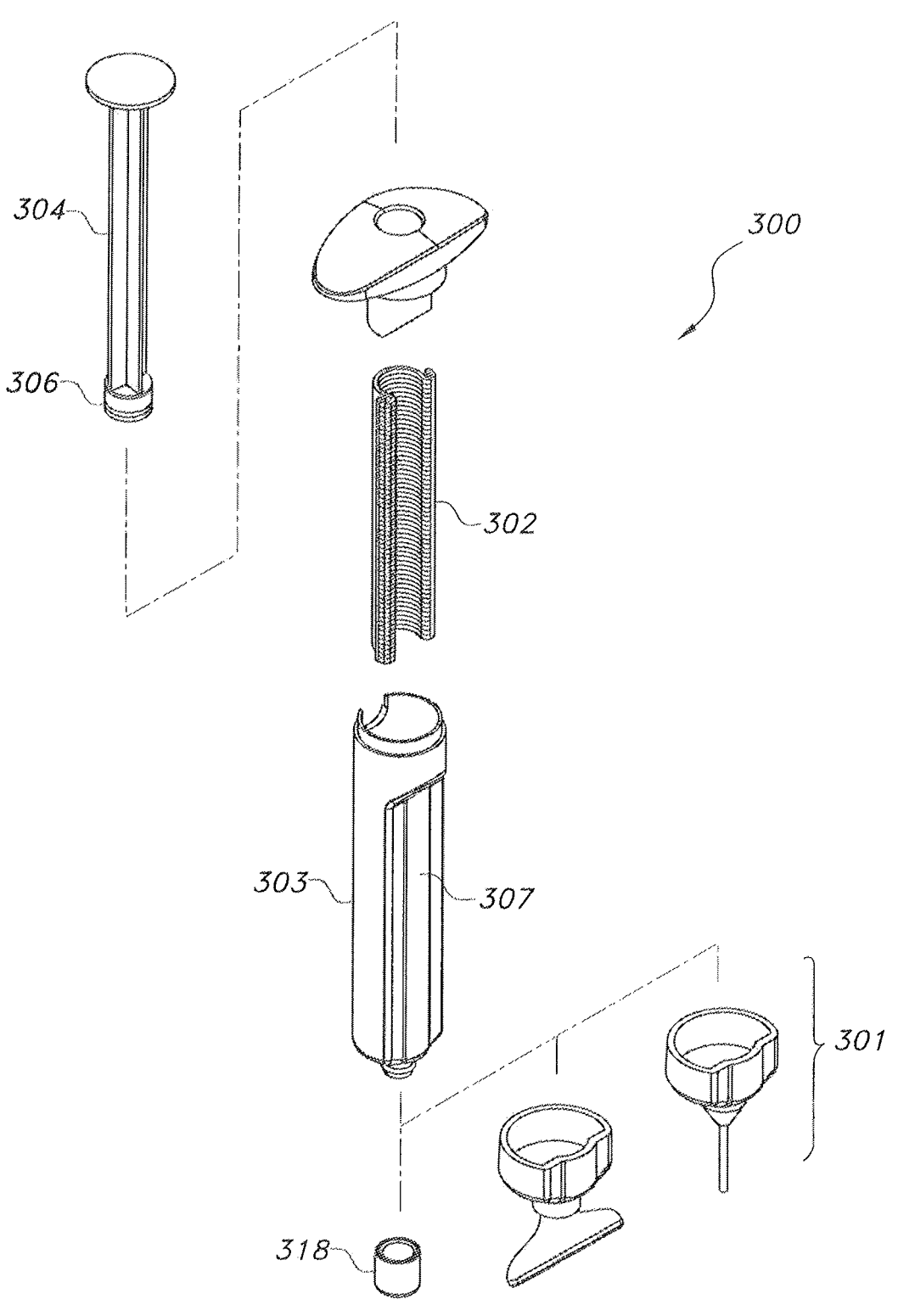
FIG. 15B is an exploded view of the applicator of FIG. 15A.
Figure 15E:
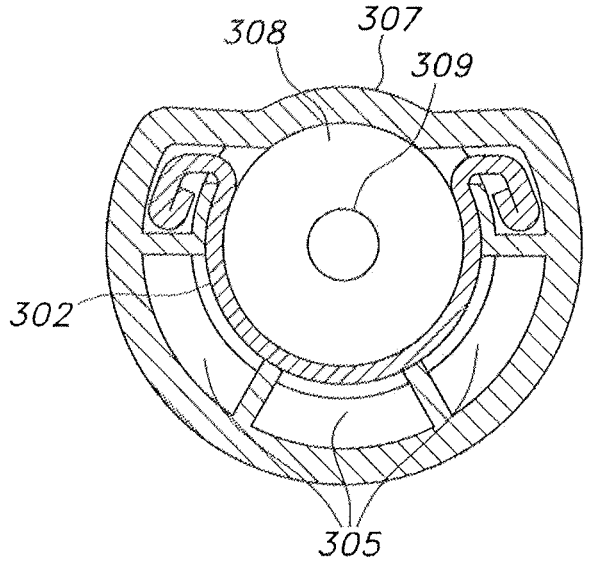
FIGS. 15C and D are side plan and section views, respectively, of the applicator of FIG. 15B.
FIG. 15 E is a horizontal section view of the applicator of FIG. 15B.

Discharging the morselized Tissue Particles (TPs) or for example specifically FTSGPs, into an applicator 300 may now be described with respect to FIGS. 15A-E. Referring to FIG. 15A, an applicator 300, which may be used to collect and dispense the TPs is typically configured as a syringe which provides a well-known means to deliver and meter out controlled volumes.

The syringe applicator 300 also serves as a device to separate excess fluids from the TPs. A cylindrical screen filter 302 is formed as an insert to the applicator body 303 and has an inner applicator chamber 308 lumen to receive a plunger 304 and piston 306. Peripheral drain channels 305 may surround the filter 302 such that excess fluid within the morselized TPs may pass freely through the filter walls, through the drain channels 305 and out the drain outlets 310. The screen filter may encompass 360° of the applicator or only a portion thereof, as shown in FIG. 15A, so as to leave sufficient area to view the contents through a window 307. The filter 302 may be a fine mesh, for example having 50 micron openings allowing fluid to pass through while containing TPs. Alternatively, filter 302, may be comprised of, for example, woven mesh or acid etched perforated screens with specifically sized larger openings, so as to drain away smaller particles with solution, while selectively containing wetted particles larger than the utilized filter openings.

FIG. 15A also shows that the processing device 10 is attached onto the processor 44, for example, with a bayonet mount 115. The processing device 44 may be cordless and include a low voltage DC motor 114 driven by a contained rechargeable battery. The battery is preferably recharged by connection to a remote ACDC charger. The low voltage DC motor may also be powered through the remotely connected ACDC power source. In both such manners the use of low voltage DC power enables the safe use of processing device 10 in the potential presence of an aqueous solution. The axially connected drive engagement 46 connects the motor shaft of the processor 44 to the central shaft assembly. Upon morselization of the TPs, the motor 114 may automatically be slowed or stopped and raised so as to open the seal 19 below the impeller, causing the morselized tissue mixture and solution to drain through the gravity driven drain 39 from the processing chamber through the outlet 26 and through the port 320 to enter the applicator 300.

The applicator 300 is shown with the plunger 304 and piston 306 in its raised position and with the cap 318 in place to close the dispensing orifice. As the TPs and solution enters the applicator 300, the fluid is drained away from the TPs as the fluid will freely pass through the filter walls 302, through the flow channels 305 and exit the applicator 300 through the drain outlet 310 into the fluid waste drain container 317. Thereafter, the plunger 304 may be advanced sufficiently into the applicator chamber 308 so as to enable the piston 306 to close off the port 320. The applicator 300 may then be removed from the processing device 10 by disconnecting inlet port 320 of the applicator 300 from the outlet port 26a of the processing device 10. Thereafter, the cap 318 may be removed from the applicator 300 and a selected applicator tip 301 may be affixed to the dispensing orifice 309 for dispensing the TPs in a manner which will be described in further detail hereinbelow.

Figure 16:
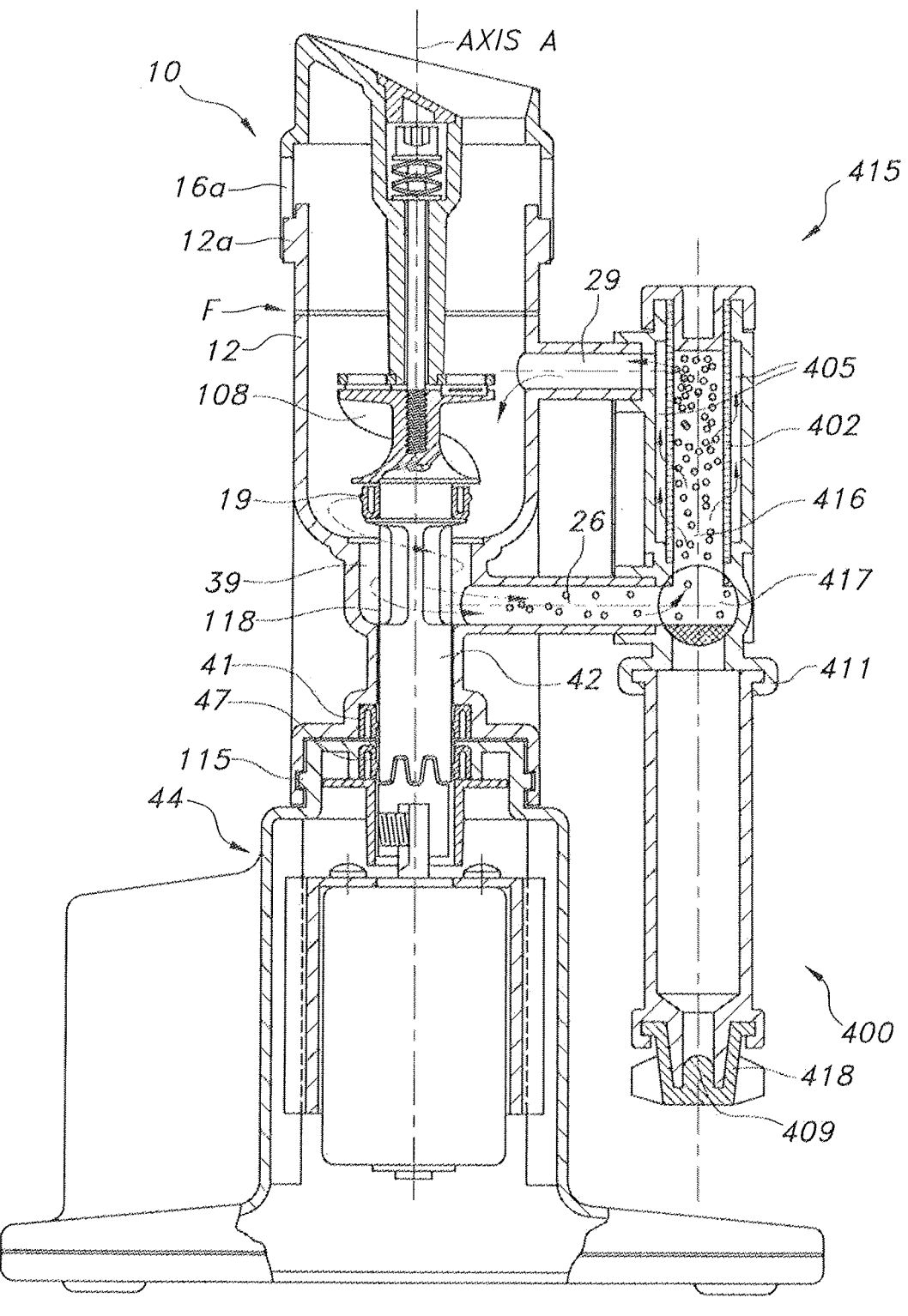
FIGS. 16-18 shown in partial section are further embodiments of the processing device of the present invention attached to further embodiments of isolation and applicator devices.

A further embodiment of the present invention, shown in FIG. 16, is similar to FIG. 15A relative to including a processing device 10 mechanically coupled onto a processor 44. The drive engagement 46 may similarly be raised to open seal 19 to drain the container 12 through an outlet 26, however, as shown in FIG. 16 (as well as in various earlier FIGS. 1, 2, 3) the drive shaft 42 may include a rotor pump 118, for example with fins integrally molded upon the drive shaft 42. The rotor pump 118 is driven by the motor 114 through axis A, to circulate solution through an isolation device 415.

FIG. 16 introduces a different isolation device 415 which circulates fluid from the processing device 10 through outlet 26 and inlet 29 conduits. Upon completing TPs morselization, the motor 114 will be automatically raised, along with drive engagement 46 and drive shaft 42, so as to open the chamber seal 19 below the impeller 108, to release fluid and TPs from container 12.

The motor speed is changed, as appropriate, to pump the solution and TPs through the outlet channel 26 and through a diverter valve 417 to enter a cylindrical isolation chamber 416 containing a cylindrical filter tube 402 lining. The filter tube 402 may be, for example a woven mesh, perforated film or acid-etched screen with openings sized appropriately to capture particularly desired sized TPs. The particles are captured within the isolation chamber 416 as fluid passes through the filter tube, and through circumferential drain channels 405, exiting the isolation device 415 through inlet conduit 29, to return into the container 12 of processing device 10. Within several brief passes the motor 114 will automatically stop as the TPs are substantially rinsed away from the container 12 and transferred into the isolation device 415.

The diverter valve 417 may then be automatically or manually switched, for example turned 90° clockwise, to open a fluid path from the isolation chamber 416 into the applicator 400. The inlet conduit 29 is positioned below the fill line (F) of container 12, enabling the head pressure of contained fluid to substantially flush the TPs from the isolation chamber 416 through the diverter valve 417, through an applicator attachment 411, and into the applicator chamber 408 of a detachable applicator 400.

Thereafter, the diverter valve 415 is closed; the applicator 400 is disconnected from the applicator attachment 411; and a plunger with piston (as shown for example in previous FIG. 15B) is manually inserted into the lumen of applicator 400. The cap 418 is removed (for example with a Luer type connection) and replaced with a selected applicator tip (as, for example introduced in FIG. 15B). In this manner, the applicator 400 is ready to dispense the TPs to a desired autologous implant site in a manner which will be described in further detail hereinbelow.

The processing device 10, isolation device 415 and applicator 400 may be packaged as an integral sterile assembly. Applicators 400 may alternatively be sterile packaged separately.

Figure 17:
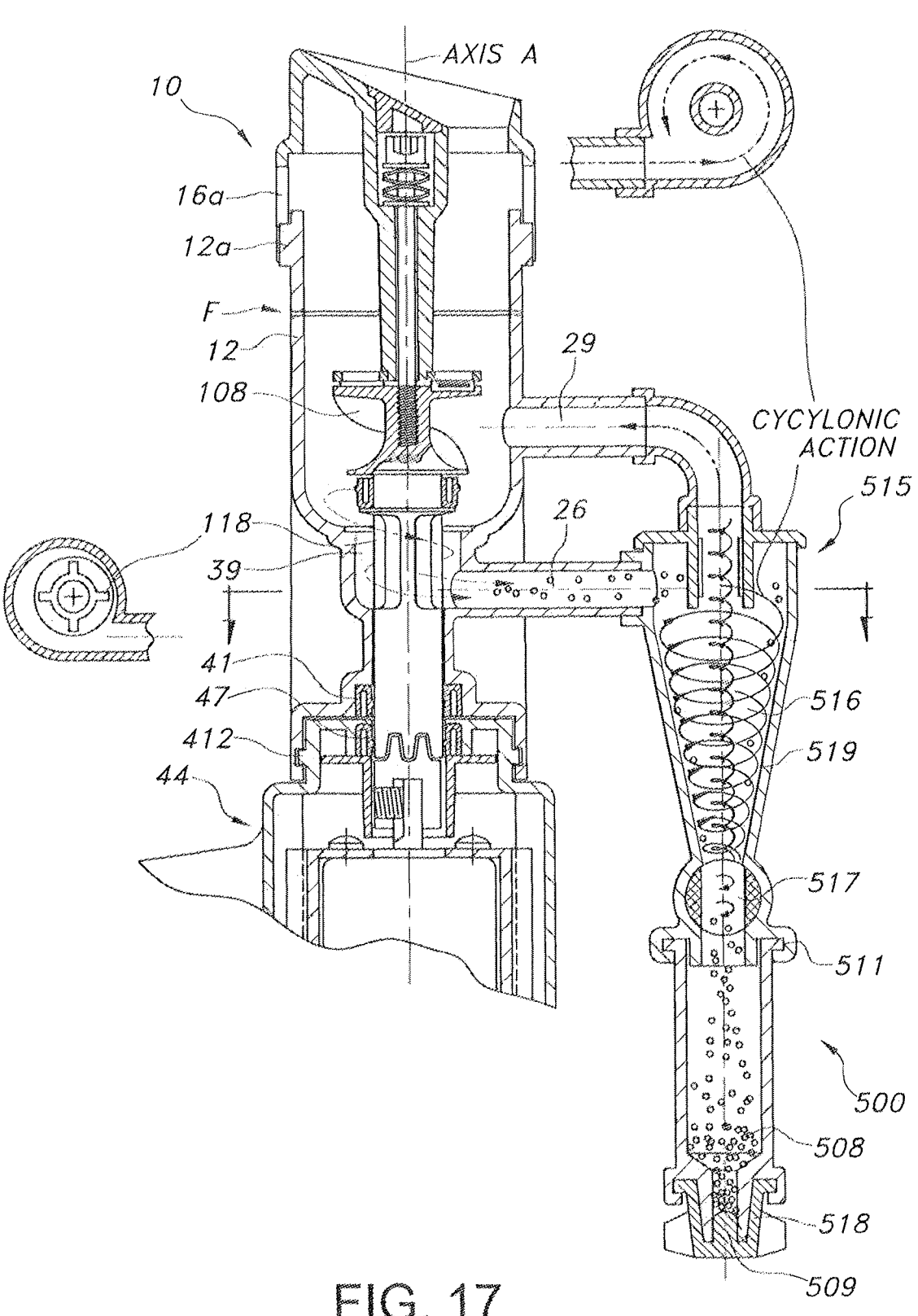

Turning now to FIG. 17, a further embodiment of the processing device 10 with processor 44 and applicator 500 is shown here coupled to a different type of isolation device 515. In this embodiment a pump 118 will similarly circulate the solution with suspended morselized FTSGPs from the container 12, through outlet 26 and returning through inlet 29 both in fluid communication with an isolation chamber 515 which in this configuration employs cyclonic action to separate the TPs from the solution. The system uses the principle of terminal settling velocity of solid particles in a centrifuge field. The outlet 26, from the processing device 10, enters tangentially into the isolation chamber 516 of the isolation device 515. High velocity centrifuge fields within the hydro cyclone cause particles to migrate rapidly to the outside walls of the conical chamber 516 and will be forced to move downward on the inside of the conical walls through a valve 517, through an applicator attachment 511, and into the applicator 500. A valve 517 may then be closed, the applicator 500 is disconnected from the collector, a plunger with piston is inserted into the applicator 500, the applicator cap 518 is replaced with the dispensing tip of choice, whereupon the applicator is ready to dispense TPs in a manner described hereinbelow.

Figure 18:
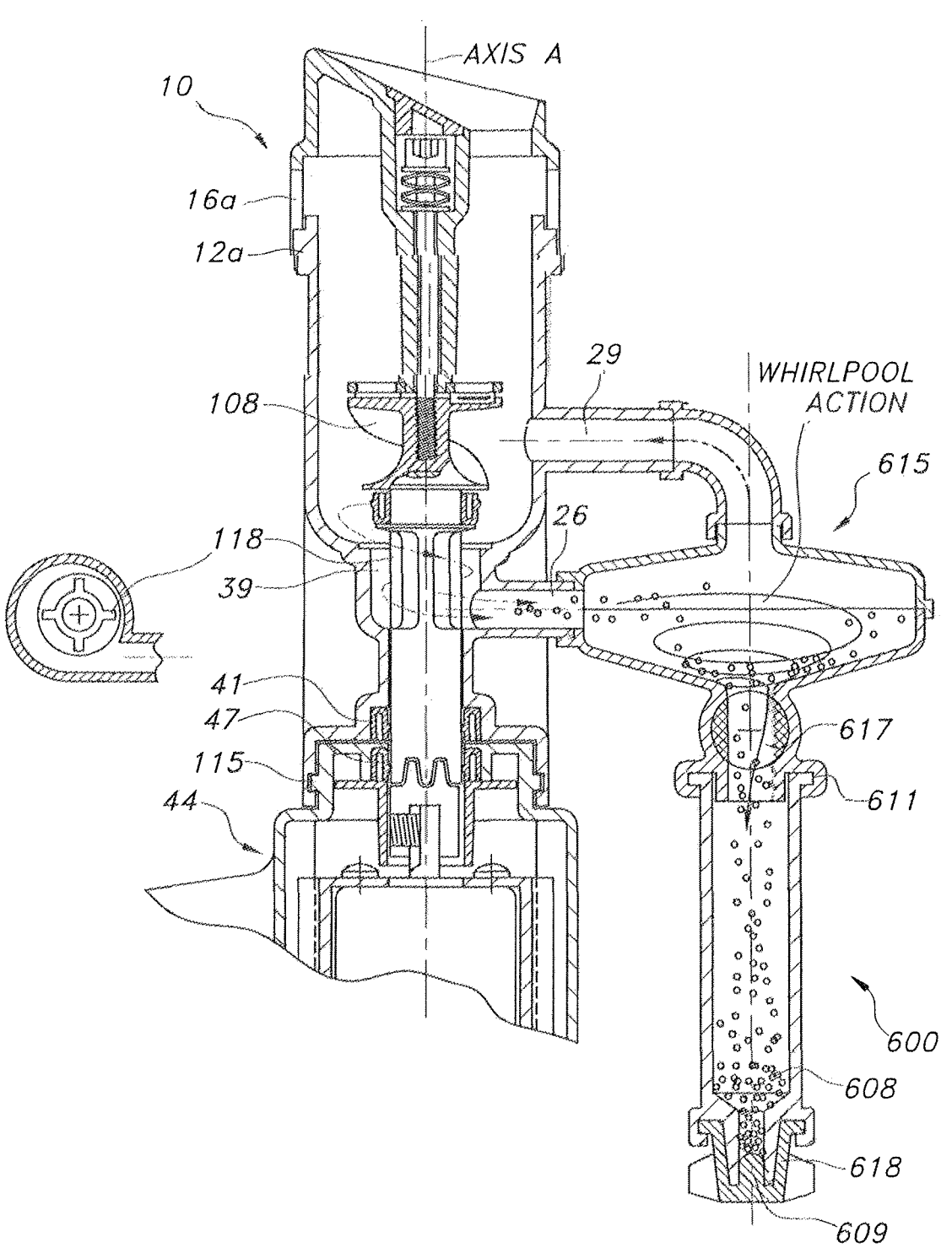

A still further embodiment is shown in FIG. 18 where the processing device 10 is coupled to the processor 44. In FIG. 18, the inlet 20 and outlet channels 26 are shown in fluid connection with an isolation chamber 616 that employs a whirlpool like action to gather the swirling TPs particles towards the central drain through which the concentrated TPs will be deposited into an applicator chamber 608 within an applicator 600. As with the above embodiments, the valve 617 is then closed, the applicator 600 is disconnected and the applicator cap 618 is replaced with a dispensing tip of choice. The applicator 600 is then ready to dispense the TPs in a manner which will be described in further detail hereinbelow.

Figure 19:
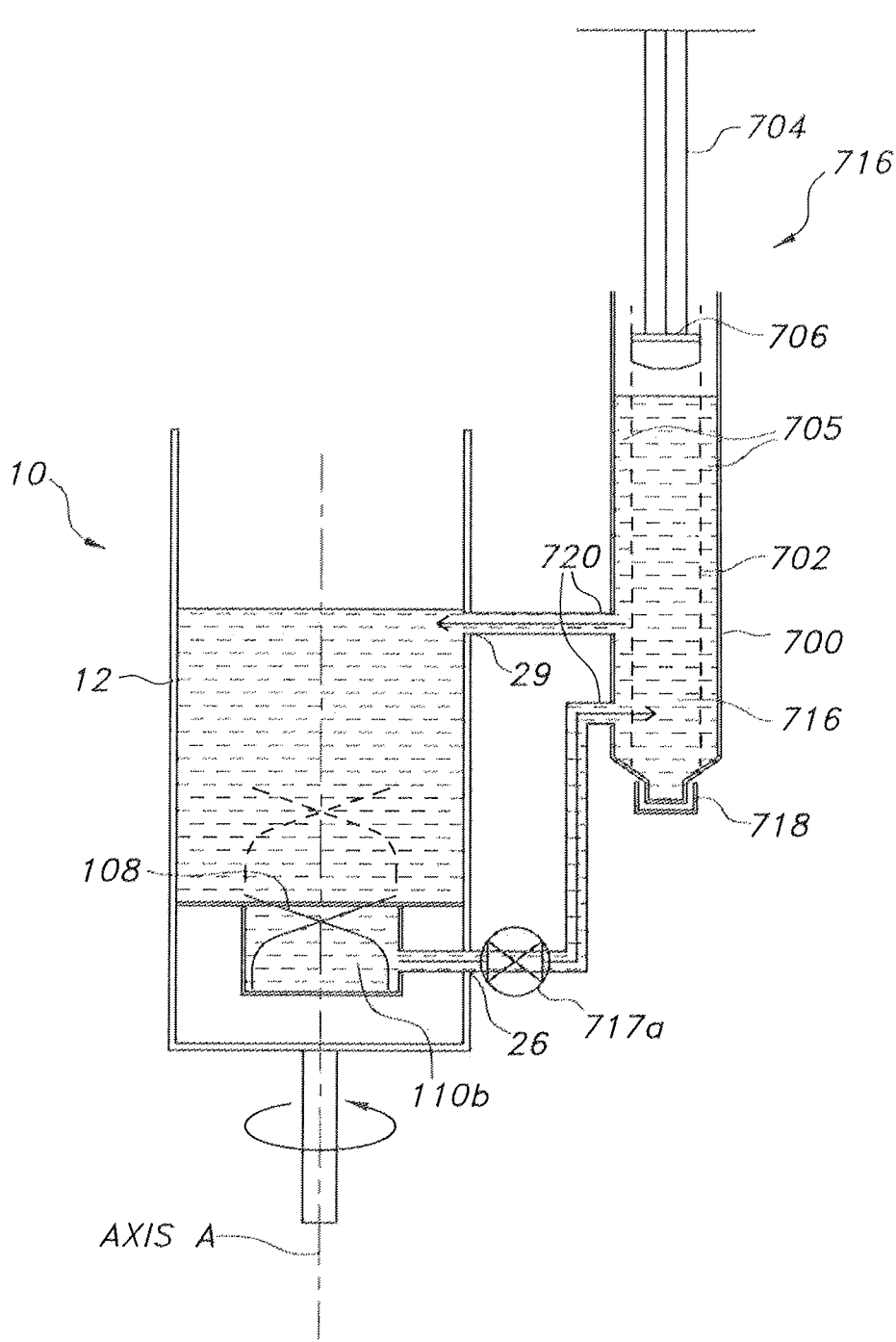
FIG. 19 schematically shows a processing device in conjunction with a further embodiment of a removable isolation device which is configured for use as an applicator device.

A still further embodiment is shown in FIG. 19 where the processing device 10 is coupled similarly as shown in FIG. 16 onto an isolation device 716 through an outlet 26 and an inlet 29. Also similar to the embodiment of FIG. 16, the isolation device 716 contains an isolation chamber 716, separated by a filter tube 702 from a drain channel or channels 705, such that solution passing through the isolation chamber 716 will pass through the filter tube 702, to pass through the drain channel 705, to pass through the inlet 29 and be recirculated through the processing device 10. However, in this embodiment, the outlet 26 and inlet 29 may include sealable closable ports 720 (not shown) such that the isolation device 716 may be detachable from the processing device 10 while containing fluid from leaking from the detachable outlet 26 and inlet 29 flow paths. In this manner the detached isolation device 716 may contain a plunger 704 and piston 706 and detachable cap 718 and together may be used as applicator 700 as similarly described in FIGS. 15C and D.

The schematically drawn circulating flow (CF) paths in FIGS. 2 and 14 have been significantly simplified, by not indicating the turbulent vortex swirl, so as to more clearly depict the recirculating nature of the fluid flow pattern. Early prototypes revealed that a vortex induced by the impeller, while desirable to continuously recirculate and mix the fluid suspended TPs, also caused the particles to travel many more circuitous times around the container 12 than necessary before being drawn through the morselizing mechanism 40.

Figures 20, 21:
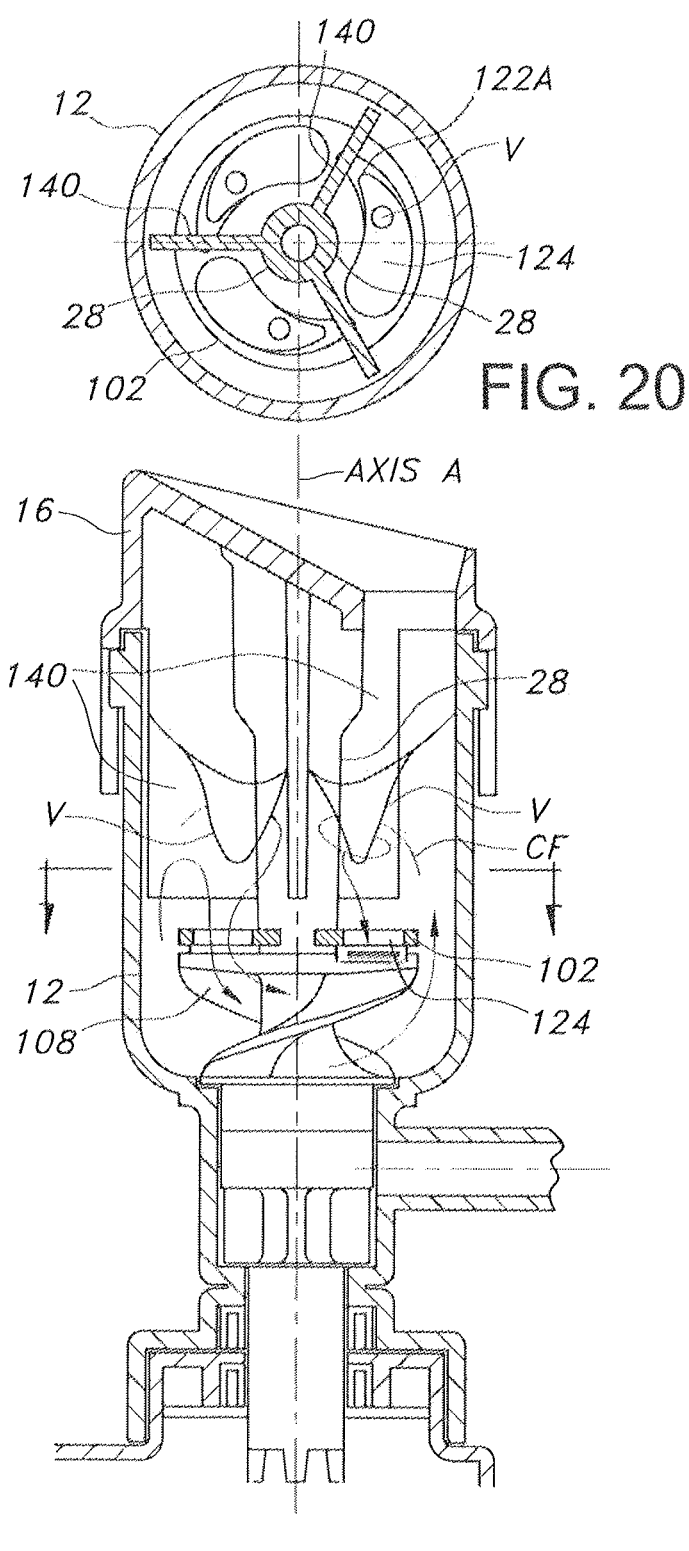
FIGS. 20 and 21 show axial and lateral sectional views of the processing device of the present invention including baffles to divert a single large vortex into separate smaller vortexes to more expediently morselize tissue.

FIG. 20, an axial view, and FIG. 21, a lateral view, introduce a preferred improvements to the processing device 10 to more expediently morselize TPs. Placement of vertical baffle panels 140, radiating from the stem 28, effectively interrupt the single vortex. The baffles are positioned proximal to the apex of each set of converging blade edges 122 on the stationary cutting member 102. The swirling fluid within the container 12 rebounds off each baffle 140, creating a separate smaller vortex V adjacent to each baffle 140. The smaller vortexes V carry the TPs more expediently through each of the continuously closing breaches 124 of the morselizing mechanism 40.

Figure 22:
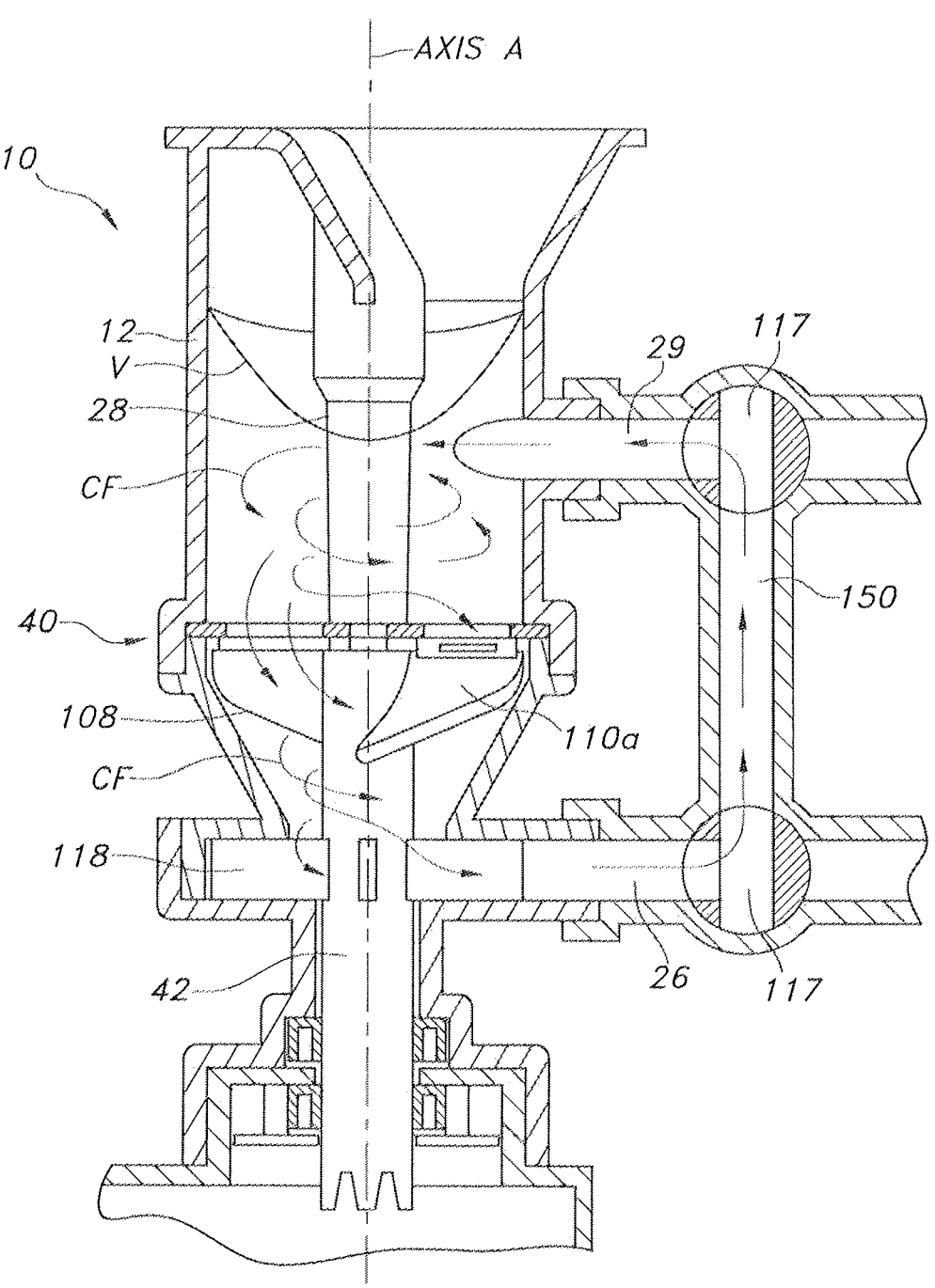
FIG. 22 shows, in section, the flow through the processing device of the present invention which recirculates externally from the processing device container.

Although the circulating flow (CF) paths within processing device 10 as described in FIGS. 2 and 14 represents a preferred embodiment (and is also included by way of example in multiple other Figs.), it is not intended to limit the scope of the invention. Whereas an impeller 108 is employed to continuously recirculate fluid and TPs through the central volume (CV) of container 12 so as to repeatedly pass through the morselizing mechanism, the fluid and TPs need not necessarily be recirculated through the peripheral volume PV upon return. FIG. 22, therefore, teaches that the fluid and suspended TPs may be recirculated through the morselizing mechanism 40 in other manners, by way of another example, to flow externally of the container 12, through a recirculating conduit 150.

Further, whereas FIG. 22 shows a rotor pump 118, integral to shaft 42 and rotating about axis A, one skilled in the art would recognize that a fluid driving pump may alternatively be included elsewhere along a recirculating conduit 150 between an outlet 26 from the processing device 10 and a return inlet 29 to the processing device 10. Further, as such, a circulating pump (not shown) need not be driven by or associated with a motor also used to drive the processor 10 and could be, for example, a separately operable fluid pump. Further, referring still to FIG. 22, such a recirculating conduit 150 may include one or more diverter valves 117, such that (upon completion of morselization) the fluid and suspended TPs can be diverted to circulate through any of various types of isolation devices, for example as described through FIG. 15A-E, 16, 17, 18 or 19.

Further still, the impeller 108 of FIG. 22, used in a system configured with a recirculating conduit 150, external to the container 12 of processing device 10, need not have vanes configured for radial thrust 110b. In such an embodiment, vanes with a pitch configured for axial thrust 110a alone may be sufficient on an impeller 108 to facilitate circulation of the tissue bearing solution from container 12 along axis A, through outlet channel 26, through a recirculating conduit 150, and through inlet channel 29 to be continuously recirculated through the morselizing mechanism 40 within container 12.

Figure 23:
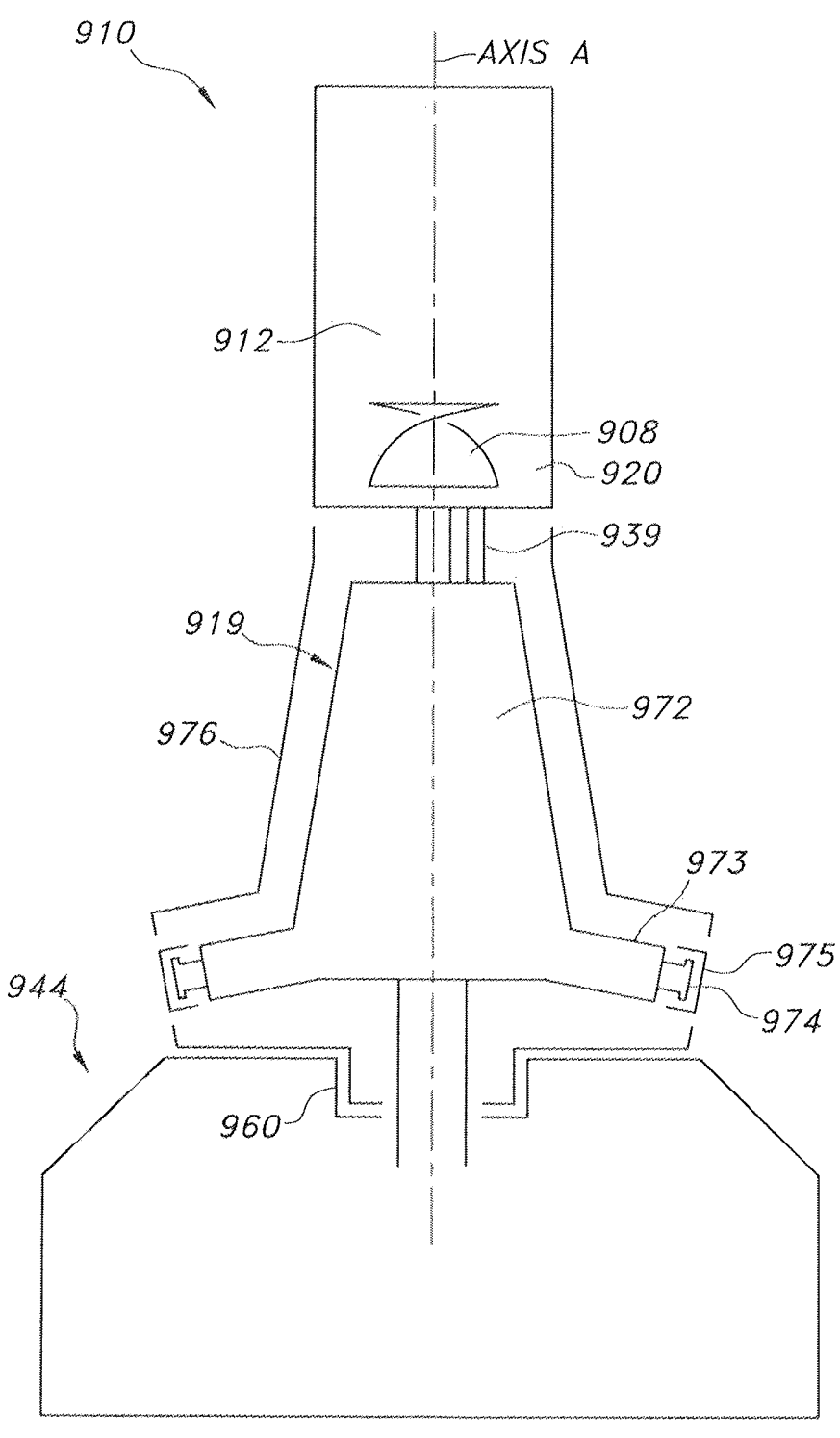
FIG. 23 is a schematic diagram showing a processing device of the present invention used in conjunction with a centrifugal device to isolate and compact particles from solution.

A still further embodiment is schematically shown in FIG. 23. Here a processing device 910 is shown used in conjunction with a centrifugal type of isolation device 919 to effectively separate and compact processed TPs, as defined herein, for dispensing through a conventional syringe (not shown). The isolation device 919 may be shrouded within a protective cover 976. The processing device 910 and isolation device 919, together with enclosing shroud 976, may preferably be integrated into a single unit, to be packaged and pre-sterilized as a single patient use as a disposable device as red bag medical waste. The device may be used multiple times within a procedure for an individual patient. The combined processing device 910 and isolation device 919 are configured to be axially aligned and fixably coupled, for example with a bayonet engagement 960, onto an aseptically cleanable reusable processor 944.

Upon completing the morselization of TPs within a processing device 910, the TPs are released in solution through a drain 939 from the bottom 920 of container 912. The drain 939 is preferably located about a central axis A of the processing device 910 or otherwise appropriately located on the bottom 920 of the container 912, so as to fluidly communicate into a central chamber 972 of the centrifugal isolation device 919.

One or more individual collection chambers 973 protrude radially from the central chamber 972, each collection chamber having a distal outlet orifice 974. The distal outlet orifice 974 has a standard threaded female Luer engagement for interchangeable attachment of a standard Luer cap 975 or a standard Luer tipped syringe (not shown).

The central chamber 972 and radially extending collection chambers 973 may be integrally formed as a hollow injection blow molded component, or produced as an assembly of injection molded components, or a combination, for example with injection molded Luer fittings affixed onto an injection blow molded unibody core.

The centrifugal isolation device 919 is configured to rotate at a high speed, for example up to 300 Gs, on precision radial type ball bearings (not shown), about an axis that is preferably coincident to or axially aligned with axis A of the processing device 910. The spinning isolation device 919 is preferably encased within a protective shroud 976. Should the Processing device 910 and the centrifugal isolation device 919 rotate about the same axis, the ball-bearing's inner shaft diameter may be sized sufficiently large as to enable independent rotation of the centrifugal isolation device 919 relative to rotation of the impeller 908 within the processing device 910.

Upon being centrifugally spun for only a few minutes, the solution suspended TP's will separate and become compacted within the radially extending collection chambers. The Luer caps 975 on the distally extending female Luer connectors 974 are then unthreaded and exchanged with appropriately sized standard syringes. Upon then drawing the compacted TPs into the syringes, the filled syringes are disengaged from the isolation device 919 and a selected Luer fitting applicator tip (for example as previously described in FIG. 15) is affixed, now ready for autologous TP application.

Morselized Particulates

A solution of suspended TPs or specifically FTSGPs or other tissues particles as described herein, may be mixed in combination with other FDA approved additives, for example handling (i.e. in saline, a buffer solution, or BioLife Solution®, or other cell nurturing/preservation solutions, etc.). The mixture may be created within the processing device 10, using the vortex circulation to achieve a heterogenous mixture of morsels comprised of naturally connected cellular and extracellular matrix material. Alternatively, some suspensions/dispersions of TPs may be homogeneous. Whether the dispersion or emulsion produced is homogeneous or heterogeneous may depend on a number of factors, including without limitation, the type of tissue(s), the medium it is suspended in, the speed and temperature of the process, among other factors. An important advantage of the method of creating the TPs suspension/dispersion of the invention, as well as the resultant suspension/disperisons per se, relates to the high cellular viability during and immediately after processing to achieve the morselization. This ability to morselized while maintaining such high cellular viability, as described herein, is unique to the present invention and not achieved by prior methods. The methods described herein produce suspensions or dispersions which contain TPs having at least 50% viability immediately after processing, which is generally in real time at the bedside of the patient; or at least 60% viability immediately after processing; or at least 70% viability immediately after processing; or at least 80% viability immediately after processing; or at least 85% viability immediately after processing; or at least 90% viability immediately after processing; or at least 92% viability immediately after processing; or at least 94% viability immediately after processing; or at least 96% viability immediately after processing; or at least 97% viability immediately after processing; or at least 98% viability immediately after processing; or at least 99% viability immediately after processing. Generally, the processing may take about 1 hour, but desirably less than 1 hour, for example, 45 minutes or less, 40 minutes or less, 30 minutes or less, 20 minutes or less, or 10 minutes or less.

The TPs may also be centrifuged to vary the density, viscosity and consistency of the tissue particles, as may be desirable for alternative surgical applications. Modulating the centrifuge speed and duration of centrifuging enables the customization of the resultant output tissue particle form, for example the consistency and density may present as a solution, or a paste, or a cream. Desirably, the resultant output (Id.) flowable and/or easily applied by spreading. The resultant output may further be presented, for example, as compacted tissue form or may be further spun to present as compacted cellular matter.

The TPs as defined herein may be most efficiently delivered from a variety of fluid dispensing devices, most notably syringes, which are familiar and useful to easily meter controlled volumes. The targeted particulate sizes will pass freely as a fluid composition through the lumen of standard Luer connectors. Tips may be interchangeably attached onto an applicator, for example, with a standard Luer thread. A variety of interchangeable applicator tips may be included within a dispensing kit for selection as most appropriate for a specific application at the option of the surgeon for a given procedure. In a cream, paste or fluid form, the TP, for example FTSGPs, may be dispensed from a syringe through various selected tip types of applicator tips. A tip may have a narrow/long fanned outlet orifice to spread over a large area. Such a fanned tip may be comprised of a flexible low durometer silicone or thermoplastic elastomer and may have a thin flexible edge, so as to be useful to gently and evenly spread the TPs over large and/or irregular wound surfaces, for example burns.

In a dense form, the TP of the invention may be spread or applied over areas or into crevices, for example with a spatula. In a dense form, the TPs, for example Cartilage Particles (CPs), may be used as a filler, for example for cartilage defects. As such the TPs, such as CPs or other tissues particles as defined herein, may be mixed with fibrin glue, autologous Platelet Rich Plasma, growth factors or other FDA approvable materials, for example as a binder. Cartilage or organ TP's may also be delivered through an endoscopic syringe attachment.

In a fluid a cream or solution form partial thickness dermal skin graft particles may alternatively be dispensed from a syringe, through a flexible cannula or a needle, for subdermal applications, for example, to fill cosmetic defects. For delivering the various TPs as described the lumen may range, for example, from 22 to 18 gauge, or most notably 22 or 21 gauge.

In a highly soluble form the TPs, which in such a case may be of the smaller variety, as described herein, may be sprayed over large areas. In the case of TPs for use on burns or open wounds, a non-adherent surgical wound dressing, may be used to prevent the applied TPs from migrating while keeping the wound site moist and protected from infection. Such commercially available dressings include, for example, commercially available Drawtex, Sofsorb, Kalginate, or Aquasorb dressings.

System Methodology

Figure 24:
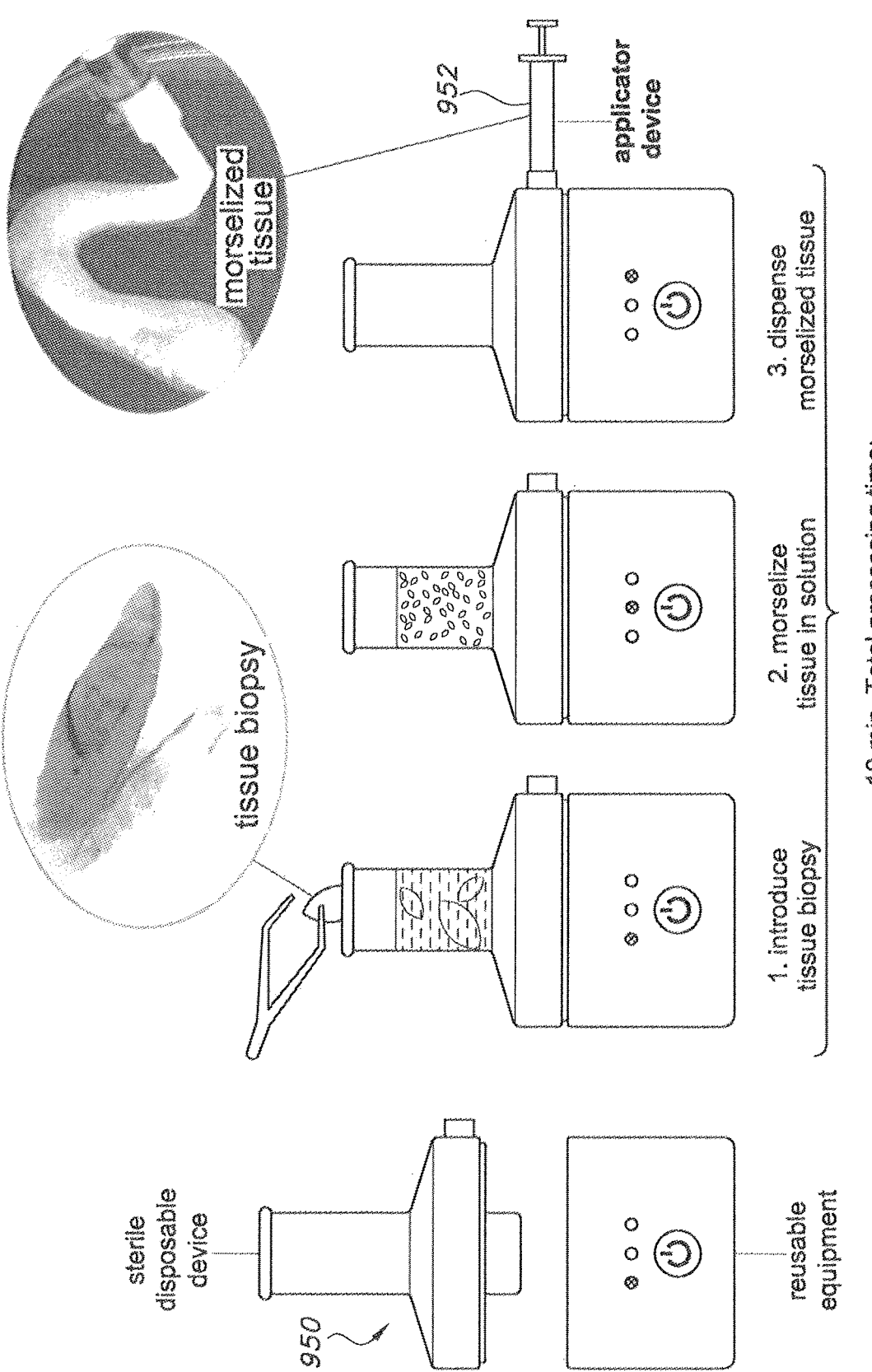
FIG. 24 is a schematic flow diagram of the system progression of the present invention.

A system of devices is described to perform a process in a methodical sequence. With reference additionally to FIG. 24, which shows the system progression in operation, the system and process includes: 1) a processing device 950 is used to introduce and morselize tissue into tissue particles within a solution; 2) an isolation device is then used to separate for dispensing morselized tissue suspended in solution from the preponderance of solution; and 3) an applicator device 952 is then used to surgically dispense and apply the collected morselized tissue. Heretofore we have described several alternatively configured devices and methods employing non-limiting details with which to accomplish a three-step process to achieve the desired outcomes.

A processor device may be used in conjunction with various types of isolation devices. For example, an isolation device may take the form of a device including a filter tube through which solution flows to isolate tissue particles as described in FIGS. 15A-E, 16 and 19; or an isolation device utilizing cyclonic action within a chamber to isolate tissue particles as described in FIG. 17; or a device using a whirlpool action within a chamber as described in FIG. 18; or a device performing as a centrifuge as described in FIG. 23; or the tissue particles may simply be isolated by sifting the preponderance of solution away through a screen (not shown); or settled tissue particles may be drawn from the solution using a standard syringe; or any number of other methods may be contemplated to isolate tissue particles in solution from the preponderance of the solution.

A processor device may also be used in conjunction with various types of applicator devices. For example, an applicator device may be a standard syringe; or an isolation device may additionally be deployed for use as an applicator as described in FIGS. 15A-E or 19: or a spatula may be used to manually apply tissue particulate; or the tissue particulates in liquids suspension may be sprayed over large wound areas; or any number of other methods may be employed to deliver and apply tissue particulates in a controlled manner.

FTSG Process Verification Studies

Full Thickness Skin Grafts (FTSGs) harvested from a human abdominoplasty were prepared in accordance with the methods disclosed herein and using the apparatus and systems disclosed herein.

Harvested sample FTSGs of various noted sizes were each separately and individually placed into fabricated experimental test apparatuses modeled as generally described in FIGS. 1-4 without baffles and FIGS. 20-21, with baffles. The processing devices were filled with 35 ml of buffered saline solution, pre-chilled with ice chips. The FTSGs were then morselized by subjecting the samples to a slicing speed of approximately 550 rpm for incrementally stepped durations, timed in minutes at ambient room temperature of 70° F. Earlier tests demonstrated insignificant temperature rise of the chilled buffered saline water over the lapse time processing each sample.

Morselized tissue samples were quantitatively assessed to determine cell viability. Processed FTSGPs suspended in solution were transferred using a syringe into 0.5 ml aliquots. The aliquots were maintained chilled in a container of chipped ice. The samples were spun down in a centrifuge at 700 RPM for five minutes followed by removing the supernatant. Quantitative cell viability analysis was performed using standard trypan blue test protocols to stain and count living cells versus purple ruptured dead cells. A table included as FIG. 25 documents highly viable cellular viability test results ranged consistently between 87% to 98% viability—across multiple exemplary sample lots and processing parameters and processing durations, a sampling of which are described below.

Additional MTT tests yielded similar quantitative results to consistently confirm data reliability. Morselized tissue particles were also qualitatively assessed. Resultant morselized tissue particles, suspended in solution, were drawn from the processor through a cannula into a syringe and expelled into a petri dish to form a shallow pool or puddle aside a metric scale. Photos of the morselized FTSGPs are shown, herein, each photo identified by test sample numbers, to visually and qualitatively document relative morsel sizes and particle appearance. As evident in the images, tissue particle sizes are relatively consistent within each sample. Maximum particle sizes became progressively smaller with longer total duration of processing time.

Figure 26A:
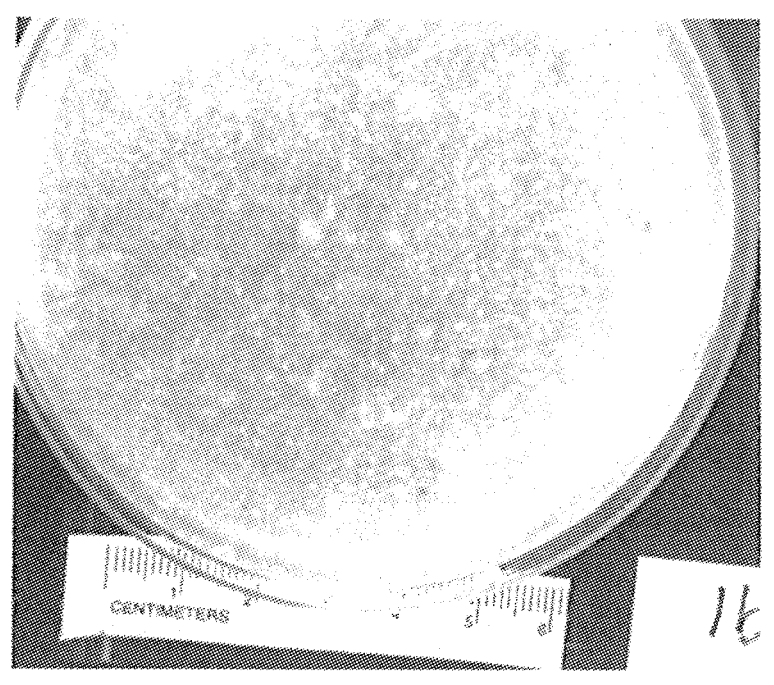
FIG. 26A shows a photograph of an inventive sample of morselized FTSGPs in fluid suspension drawn from an inventive processor as described herein without baffles after 4 minutes of processing.
Figure 26B:
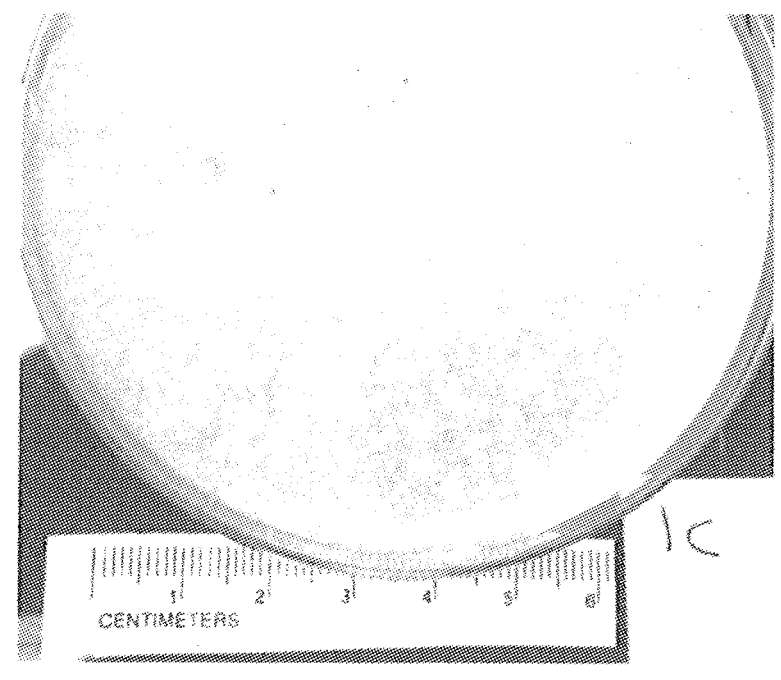
FIG. 26B shows a photograph of a subsequent inventive sample of morselized FTSGPs drawn after a total of 7 minutes of processing without baffles.

In exemplary morselization studies, ten portions of full tissue skin grafts (FTSGs), each approximately 12 mm×6 mm×4 mm thick were morselized in a processor without baffles, containing 35 ml of buffer solution with the blades rotating at approximately 550 RPM. FIG. 26A (test 1*b*) shows a sample of morselized FTSGPs in fluid suspension drawn from the processor after 4 minutes of processing. FTSGPs in solution were transferred to form a shallow pool in a petri dish to visualize individual particles. The maximum sizes of individual particles appear to generally be no more than approximately 1.5 to 2.0 mm on any axis. The majority of particle sizes appear less than 1 mm. FIG. 26 shows a subsequent sample then drawn after an addition three minutes, for a total of 7 minutes. The second sample appears more densely populated with particles and the typical maximum particle sizes appears to have been reduced to no more than 1.5 mm across.

Figure 27:
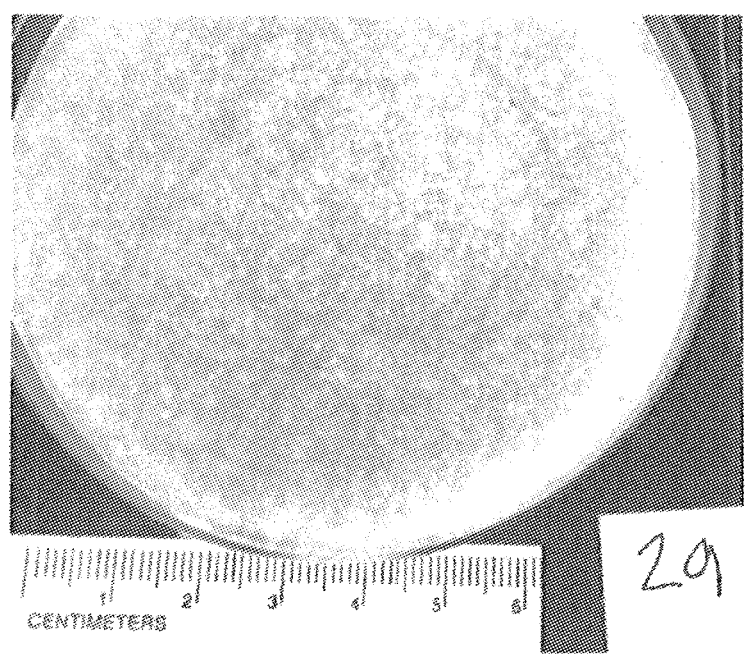
FIG. 27 shows a photograph of an inventive sample of morselized FTSGPs using an inventive process and device without baffles after a total of 7 minutes of processing.

In a next exemplary morselization study, still using the same patient tissue, the processing chamber included three baffles and four (versus 10) portions of FTSGs. The sample was again processed with 35 ml buffer and 550 RPM. As shown in FIG. 27, after being processed for 3 minutes, the resultant morselized FTSGPs were similarly sized and particle density as the previous sample after 4 minutes.

In other studies, not included here, similarly morselized FTSGPs have been demonstrated to be injectable through 22 gauge needles. The term injectable as used herein is meant to include dispensing through a syringe and is not intended to be limited to being injected only into the body, but also includes dispensing onto the body, such as onto a wound.

Figure 28A:
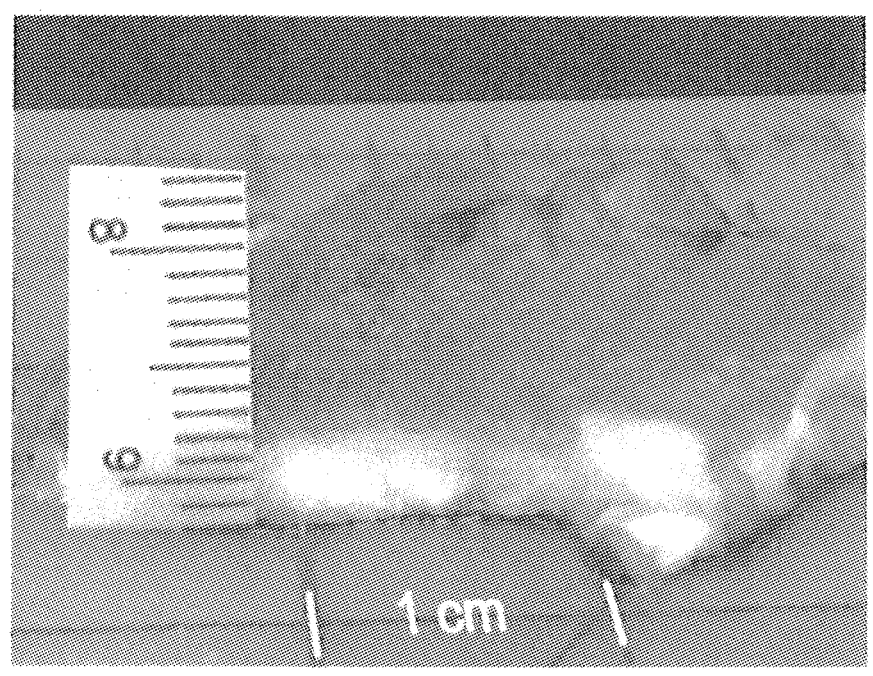
FIG. 28A is a close-up view of a portion of the FTSG prior to processing, with a sectional view revealing the thin layer of epidermal tissue (typically including pigmented stratum corneum, stratum lucidum, statum granulosum, thickly cell populated stratum spinosum, and stratum basale), over the thicker layer of generally white dermis (including dermal papilla, stem cell rich hair follicles, sweat glands, capillaries, sensory nerve fibers, sebaceous glands and other dermal components—all contained within an abundance of collagen fibers and connective tissue).

In a next exemplary morselization study (test 4*a*)—again using the same patient tissue and processing device and process parameters—multiple larger portions of tissue, measuring approximately 2 cm×3 cm were inserted into the processor and morselized for 4 minutes. FIG. 28A is a close-up of a portion of the FTSG prior to processing, with a sectional view revealing the thin layer of epidermal tissue (typically including pigmented stratum corneum, stratum lucidum, statum granulosum, thickly cell populated stratum spinosum, and stratum basale), over the thicker layer of generally white dermis (including dermal papilla, stem cell rich hair follicles, sweat glands, capillaries, sensory nerve fibers, sebaceous glands and other dermal components—all contained within an abundance of collagen fibers and connective tissue).

Figure 28B:
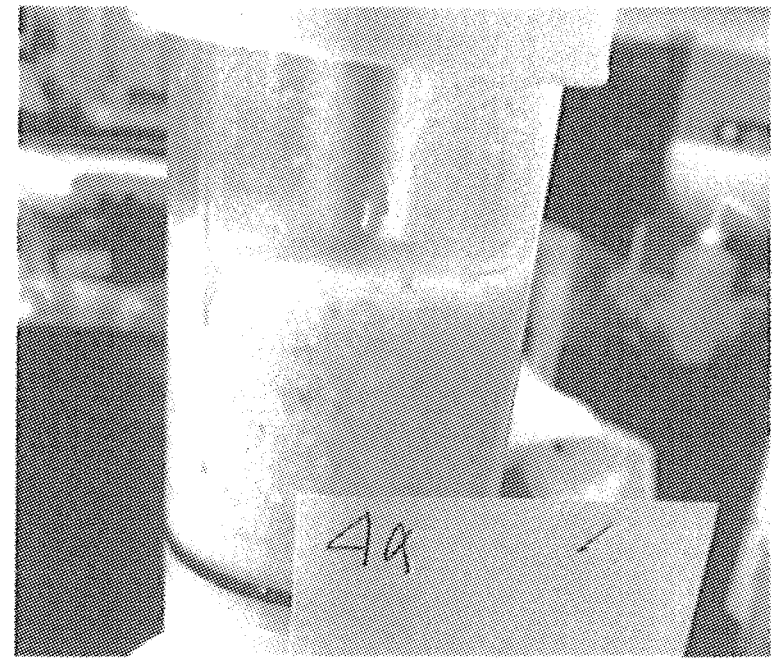
FIG. 28B shows the resultant dense mixture of inventive morselized FTSGPs particles suspended in 35 ml of buffer solution, contained within the processor chamber.
Figure 28C:
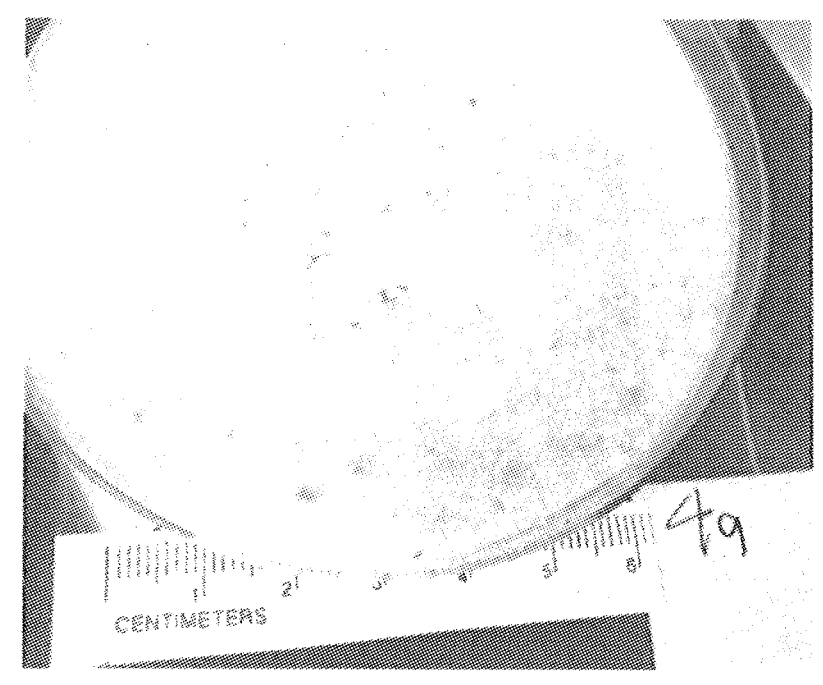
FIG. 28C shows an enlarged view of the densely populated inventive FTSGP tissue particle solution presented in a petri dish.
Figure 28D:
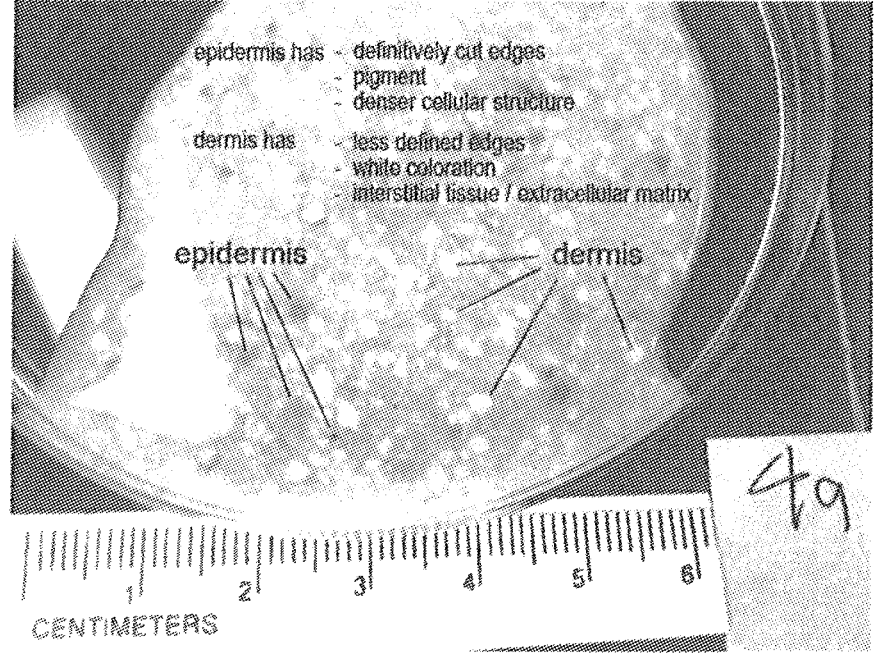
FIG. 28D shows an enlarged view of the inventive processed FTSGPs, annotated to point out that the mixture contains differing amounts of epidermis (pigmented) versus dermis (generally whiter), varying proportionally looking at the sectional view of pre-processed tissue.

FIG. 28B (still test 4*a*) shows the resultant dense mixture of morselized particles suspended in 35 ml of buffer solution, contained within the processor chamber. FIG. 28C shows an enlarged view of the densely populated tissue particle solution presented in a petri dish. FIG. 28D shows an enlarged view of the processed FTSGPs, annotated to point out that the mixture contains differing amounts of epidermis (pigmented) versus dermis (generally whiter), varying proportionally as anticipated looking at the sectional view of pre-processed tissue. It also appears that the epidermal tissue (more densely populated with cellular structure) slices more sharply, relative to the more fibrous dermal tissue. The epidermal and dermal tissue particles appear to be distributed rather consistently throughout the mixture.

Figure 29A:
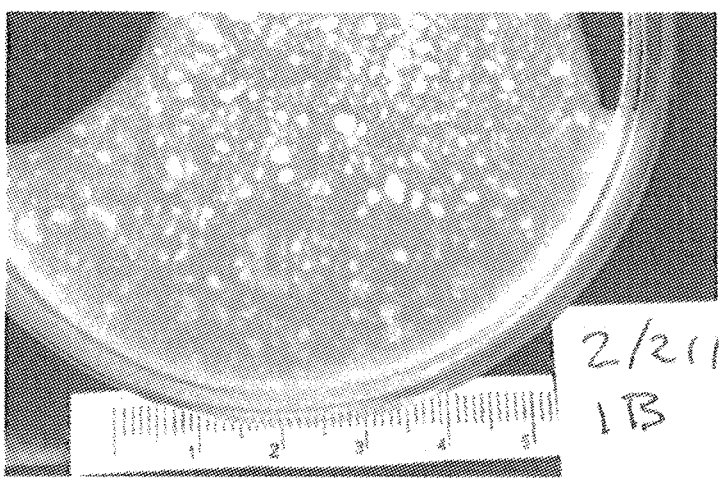
FIGS. 29A-E show samples processed using the same device and same parameters as FIGS. 28A-D, on a different day and with abdominoplasty derived from a different patient.

FIG. 29A were processed using the same device and same process parameters as FIGS. 28A-D, however, on a different day and with abdominoplasty derived tissue from another patient. Together, these studies demonstrate a repeatable process, able to achieve consistent FTSGPs outputs, relative to qualitative appearance and particle size, as well as, consistently high quantitative cellular viability.

Figure 29B:
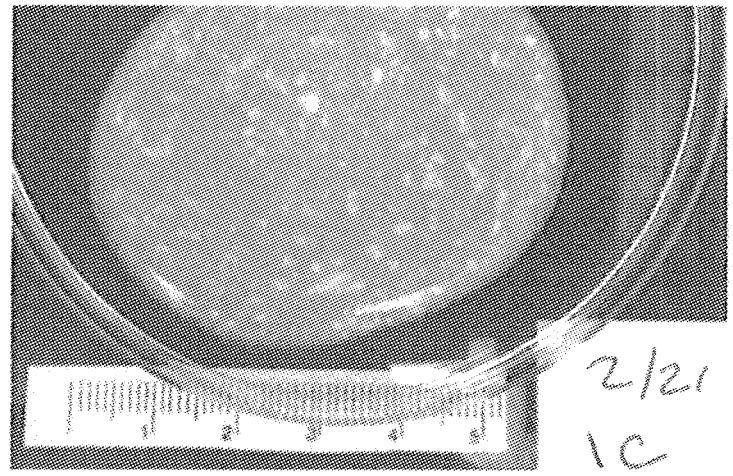

A similarly sized (slightly larger) single portion of FTSG, measuring approximately 2.5 cm×4.5 cm was morselized for 4 minutes before taking the photo for FIG. 29A (a different sample test 1*b*). FIG. 29B (sample test 1*c*) was then morselized for an additional 3 minutes, for a total of 7 minutes. And FIG. 29C (sample 1*d*) was morselized an additional 3 minutes, for a total of 10 minutes. Only a small shallow puddle of resultant FTSGPs is shown in each of these images so as to better visualize individual particle sizes. The overall volume of processed FTSGPs for this study appeared as densely populated as in the previous study for FIGS. 28 A-D.

The tabled data in FIG. 25 demonstrates relative consist and repeatable cellular viability outputs for each of the FTSGPs mixtures documented for exemplary test samples included in FIGS. 26A-B, 27 and 29A-E.

Figure 29C:
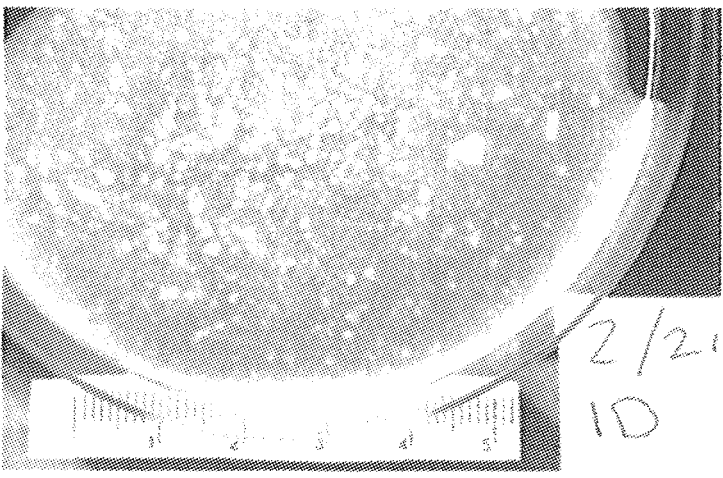
Figure 29D:
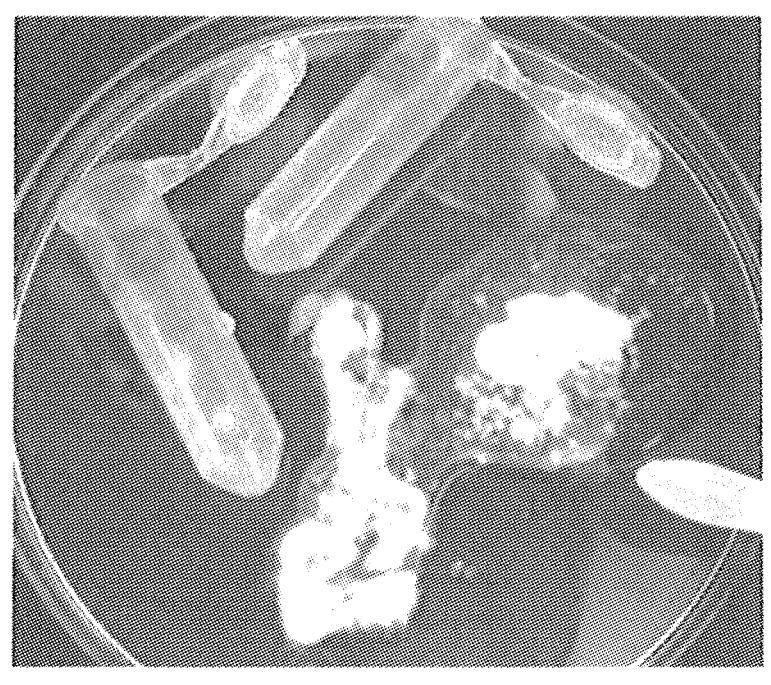
Figure 29E:
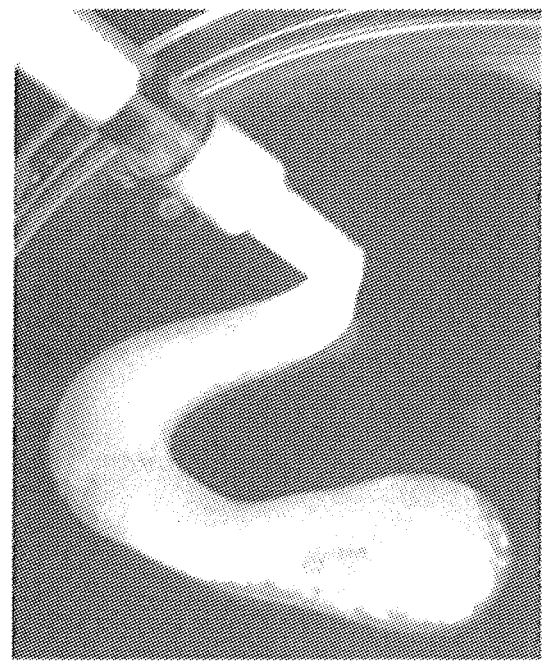

FTSGPs shown in FIG. 29C (test 1*d*) above and a subsequent sample (test 2*b*) were further centrifuged in 1.5 ml aliquots for 4 minutes at 700 RPM. The resultant tissue form, shown in FIG. 29D demonstrates the ability to achieve a fine paste-like mixture which can be dispensed through a syringe as demonstrated in FIG. 29E. Such a FTSGP tissue form may be easily applied and dispersed, for example, over expansive wound surfaces.

Articular Cartilage Process Verification Studies

Articular cartilage was harvested from the peripheral edges of a bovine knee condyle using a 2.5 mm ring curette and then morselized in accordance with the methods disclosed herein and using the apparatus and systems disclosed herein.

Figure 30A:
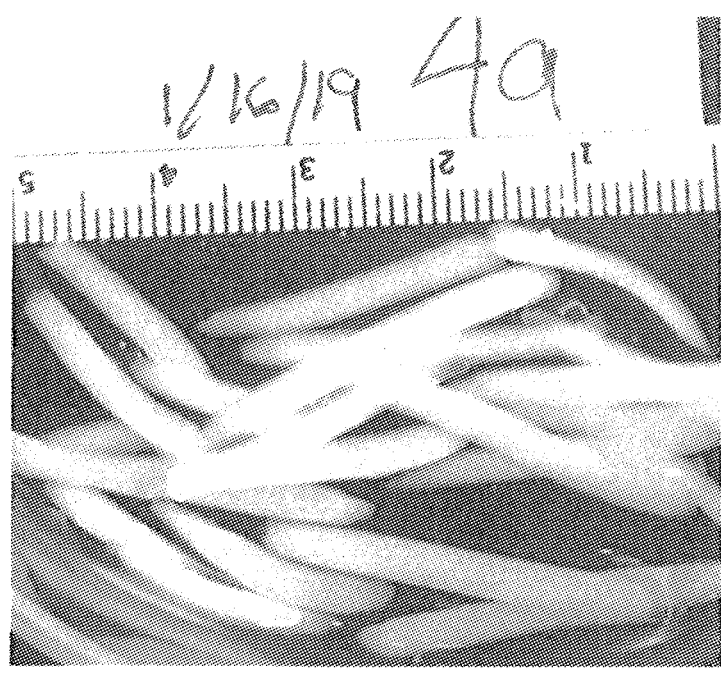
FIGS. 30A-B shows harvested cartilage portions and morselized cartilage respectively in accordance with the present invention.

The harvested cartilage portions, shown in FIG. 30A, (test 4*a* on Jan. 16, 2017) ranged in approximate size from about 1.0-2.2 cm long, 2-2.5 mm wide and 0.75-1.2 mm thick. The portions of cartilage were inserted 3-4 at a time into 35 ml of buffered saline solution, within an apparatus as described previously in FIGS. 1-4 without baffles, with the slicing blades rotating at about 550 RPM within the morselizing mechanism. The cartilage tissue grafts were morselized for a total duration of 15 minutes at room temperature.

Figure 30B:
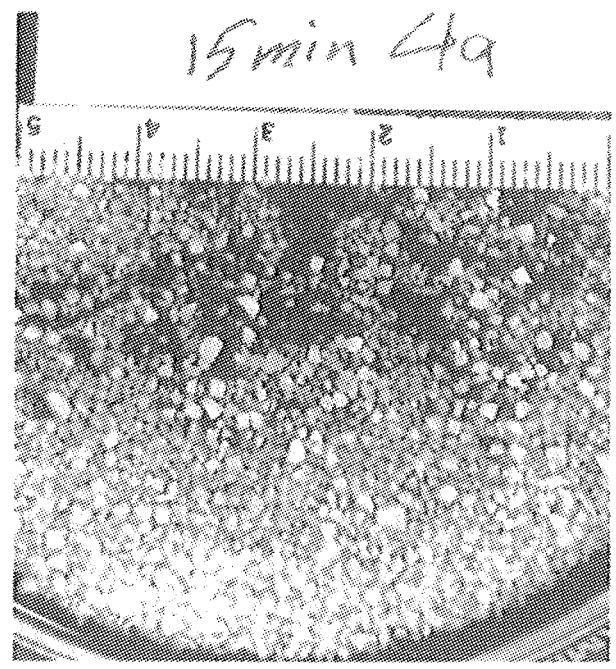

The resultant cartilage morsels are shown in FIG. 30B, demonstrating the ability to also finely morselize articular cartilage within a device and by a process as described herein to similarly process full thickness skin graft tissue.

Further details of the present invention are shown and described hereinbelow with respect to FIGS. 31-38. These details include the technology advantages and components, the needs and benefits, the technology procedure, tissue types and preparation, the process, variable tissue particle sizes, tissue dispensing options, clinical indication and development status.

It is contemplated that the present invention meets a significant unmet need. Full thickness skin grafts are the gold standard for chronic wounds and burns, but are rarely used because dermatomas create donor sites that do not heal and the procedure must typically be done in an operating room.

The present invention can generate a full thickness skin graft rapidly without leaving a conventional donor site to heal.

The present invention can also be customized to be applied to fit wound anatomy and can be done as an office procedure. The resulting process of the present invention and the grafts produced thereby are fast to process, are minimally invasive, antiseptic, provide superior viability and are cost effective solutions for wound healing. The system, equipment and process of the present invention can be conducted at bedside, including preparation of the morselized TPs and formation of a fluid having a pH to help sustain the tissues, and dispensing of the TPs onto/into the area intended to be treated, which may be a wound, a cosmetic or plastic surgery area, an internal organ area and the like.

Figure 31:
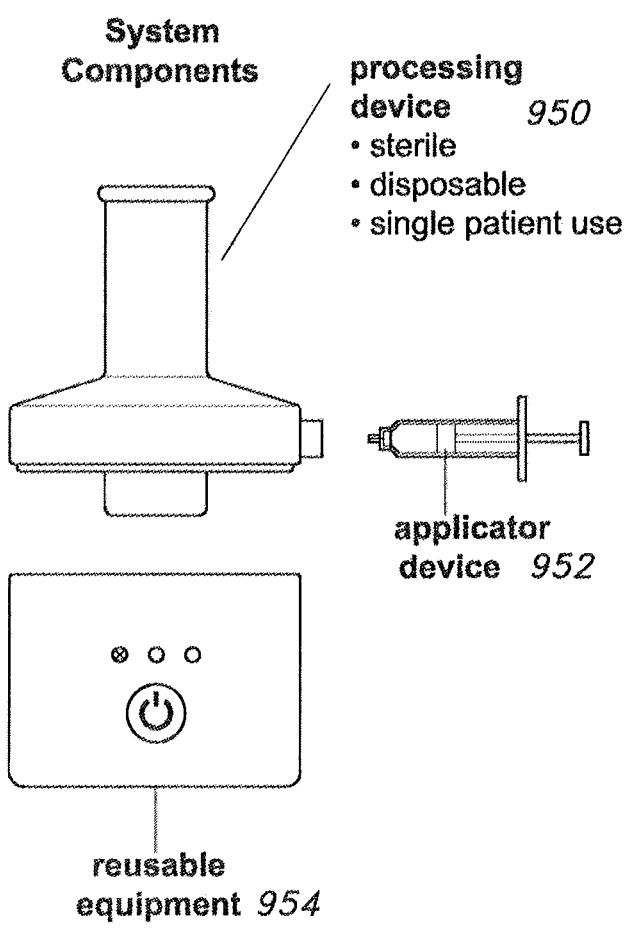
FIG. 31 shows schematically the device technology used in accordance with the present invention including a processing device, an applicator device and reusable equipment.

As shown in FIG. 31, use of the device of the present invention, which includes a processing device 950, an applicator 952 and reusable equipment 954, allows for retention of the original tissue structure, high tissue/cell viability (90-95%) and the ability to vary tissue particle size. In addition, versatile dispensing methods such as spread paste, spray and injectables may be used. These are all acceptable for in-office procedures and may be completed within approximately 20 minutes or less, desirably about ten minutes or less. Moreover, the present invention allows for processing of multiple tissue types such a skin, cartilage and organs.

Figure 32:
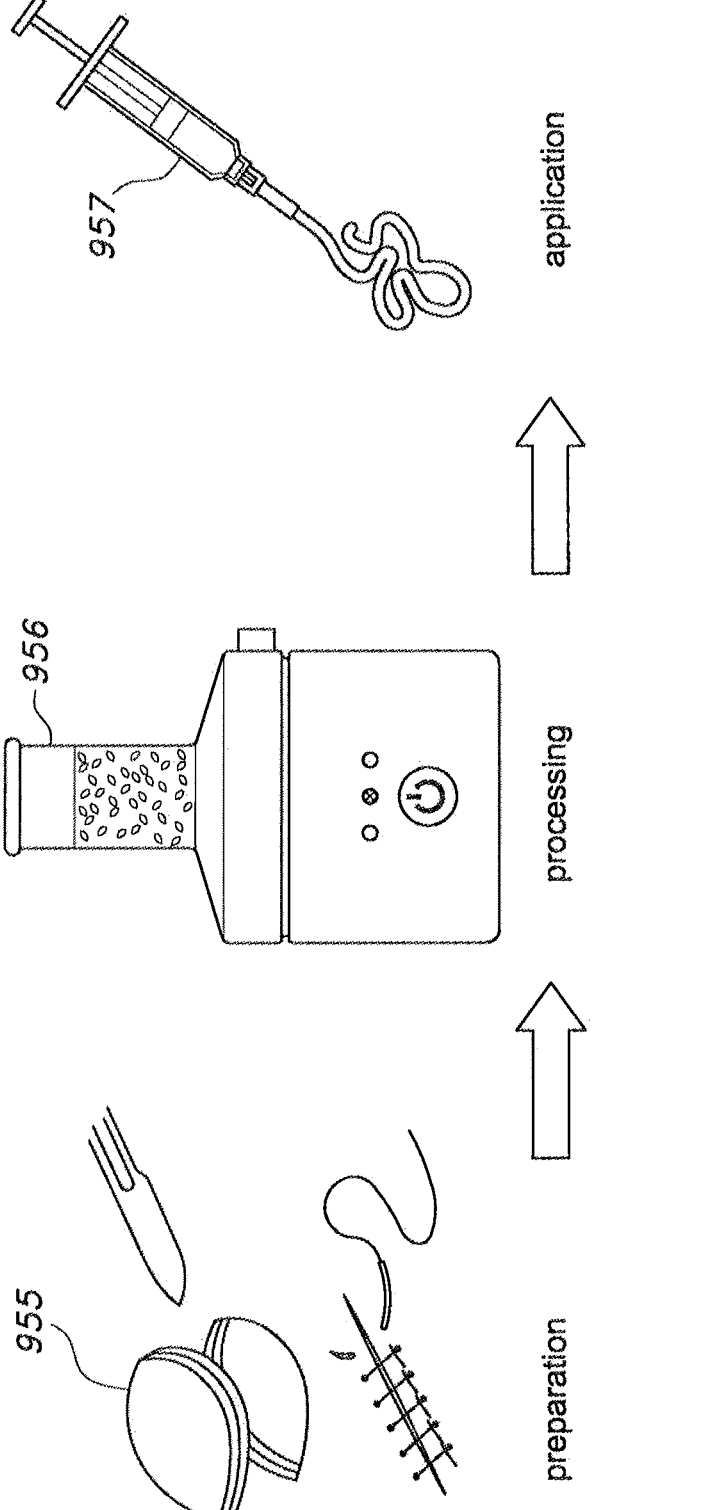
FIG. 32 shows sequentially, the preparation, processing and application employed in accordance with the present invention.

Referring to FIG. 32, the complete total procedure is completed within thirty minutes. Preparation 955 is improved as the procedure results in fast healing, low pain levels, fast harvesting and processing, and a suture closed donor site. The processing 956 to form the morselized TPs is conducted in a closed antiseptic system taking no more than about ten minutes. The process is automated and can accommodate variable particle size and results in high cell viability (90%+, such as 99%). Application 957 may be done by selectable tips on irregular surfaces and with variable wound sizes. Also, the application may be injectable. The morselized TPs of the present invention are desirably prepared in a pH suitable for maintaining viability once they have be morselized into the intended sizes. The fluid containing the morselized highly viable TPs may be dispensed using a conventional syringe onto or into the area to be treated. The fluid containing the morselized TPs suspended therein may be applied to a wound, or other area of the body in need of treatment, such as in a body joint, a plastic surgery application or cosmetic application, or other area of use to enhance the health the of tissue and/or overall appearance and health of the patient.

Figure 33:
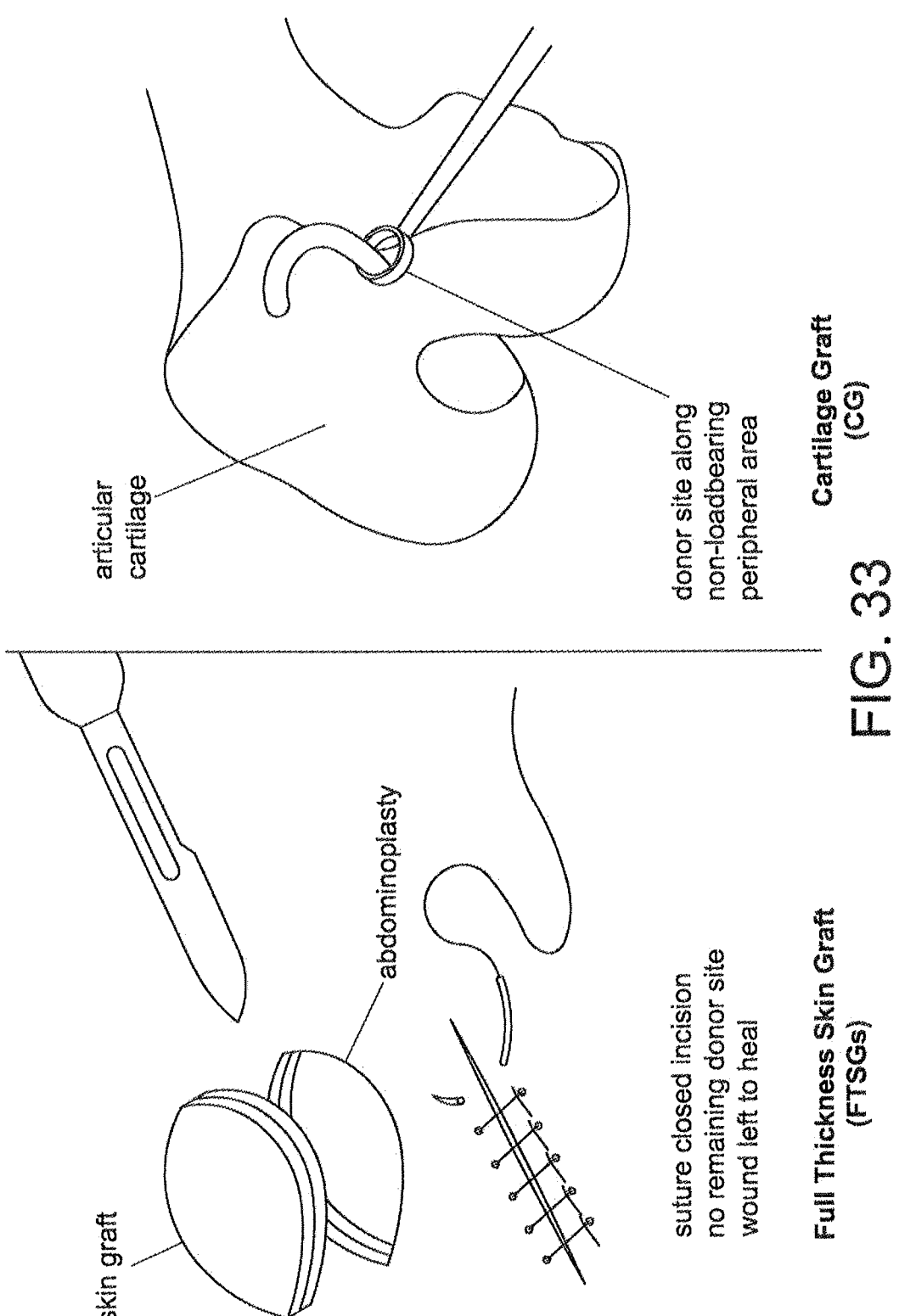
FIG. 33 shows the present invention with reference to full thickness skin grafts and cartilage grafts.

Turning now to FIG. 33, therein as shown, the preparation process using both full thickness skin grafts (FTSGs) and cartilage grafts (CG).

Figure 34:
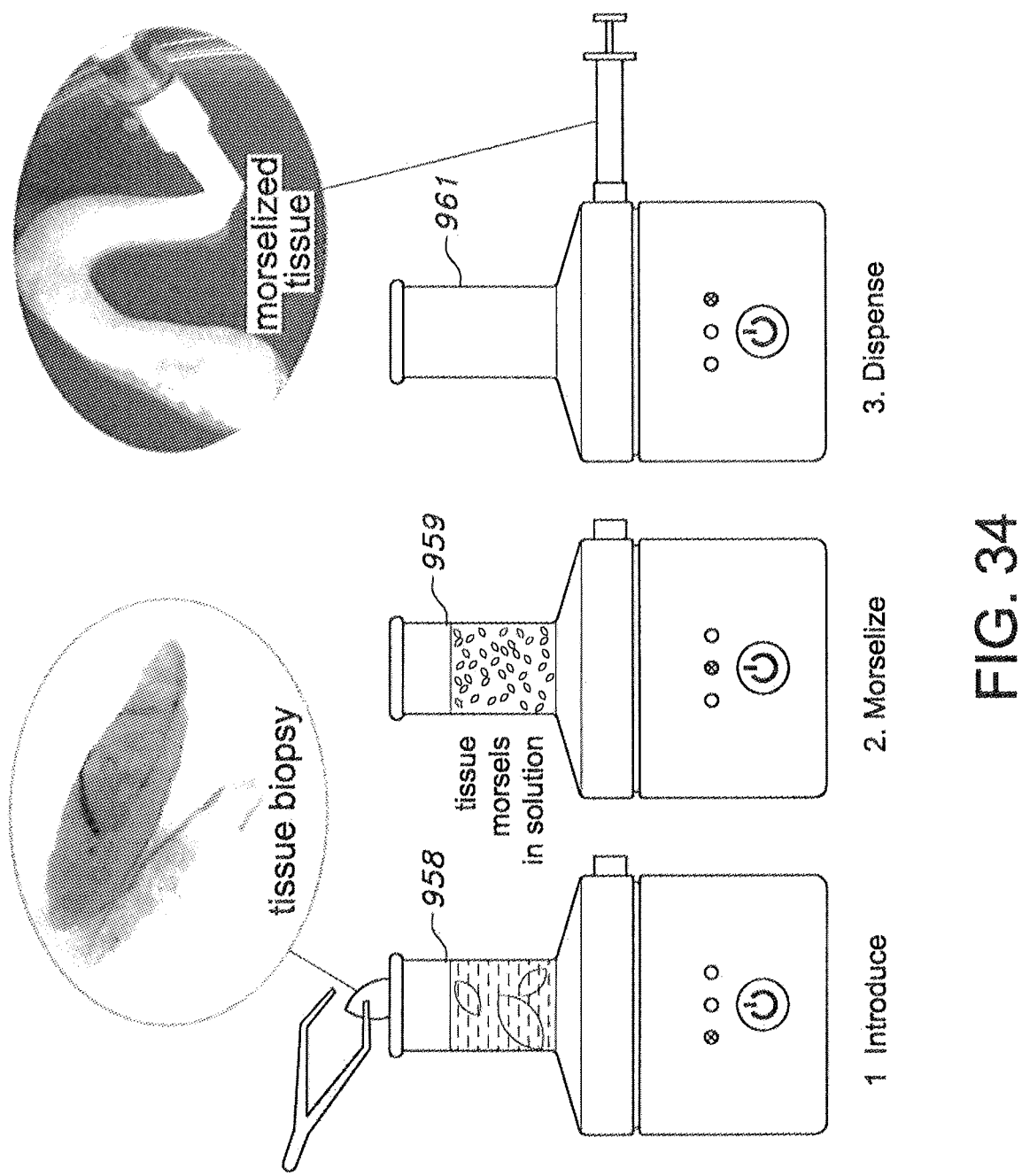
FIG. 34 shows the process employed in in the present invention including introduction, morselization and dispensing.

FIG. 34 shows the basic three-step process with respect to morselized abdominoplasty tissue in solution dispensed from a 1 mm syringe. This includes introduction 958, morselization (cutting the donor site tissue in particles) 959, and dispensing 961.

Figure 35:
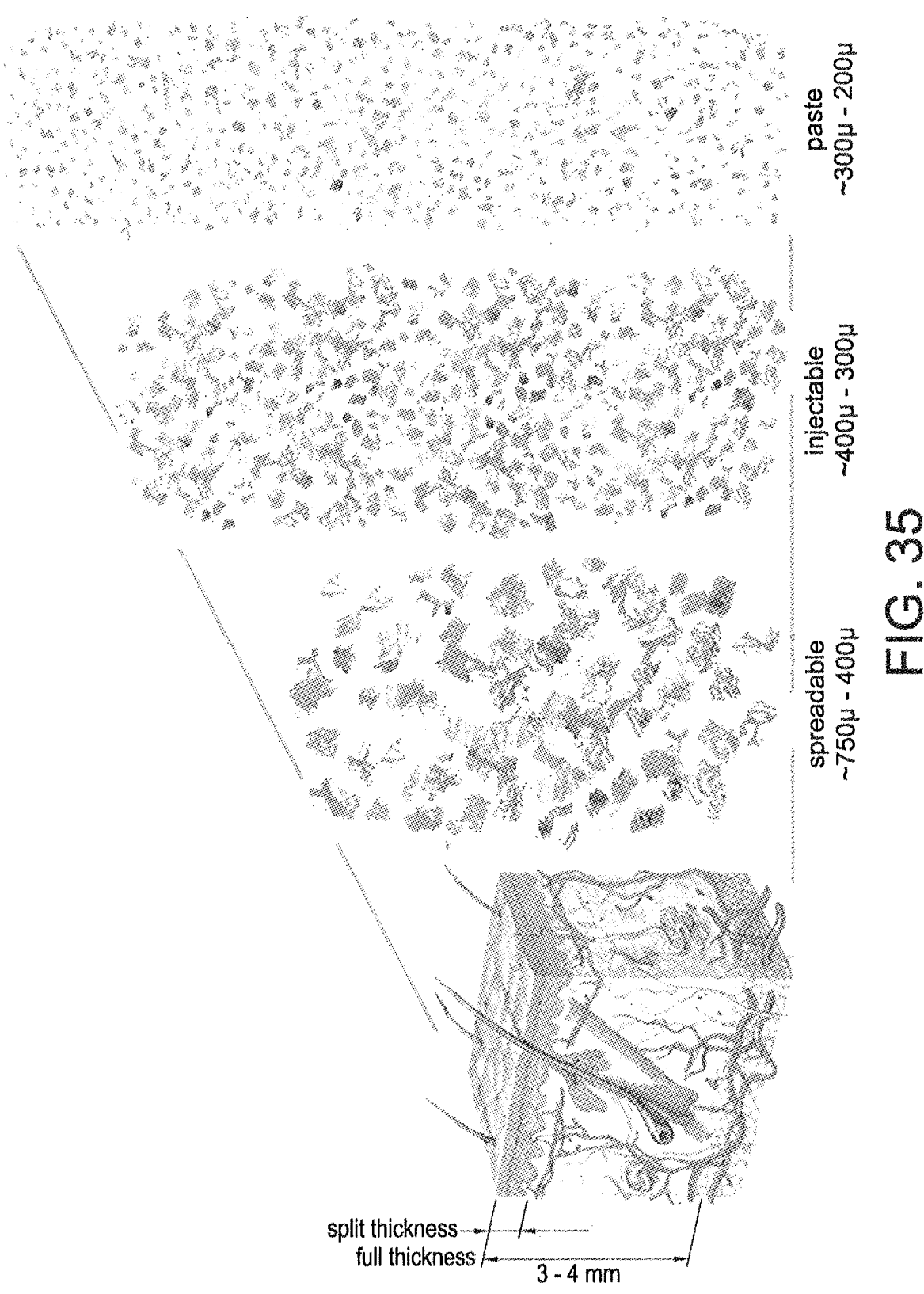
FIG. 35 shows variable tissue particle size produced in accordance with the present invention including full thickness skin graft particles containing cells and extracellular connective tissue.

FIG. 35 shows variable tissue particle sizes, which may be formed by the inventive process and using the devices and systems discussed herein, of full thickness skin graft particles (FTSGs) (also referred to as morsels) containing cells and extracellular components.

FIG. 36 shows various dispensing tip options and devices including spreading 980 using a fan-tip wiper 981; a paste 982 using a cannula 983; spray 984 using a nozzle 985 and an injectable 986 using a needle 987, all coming from an appropriate applicator device 952.

Figure 37:
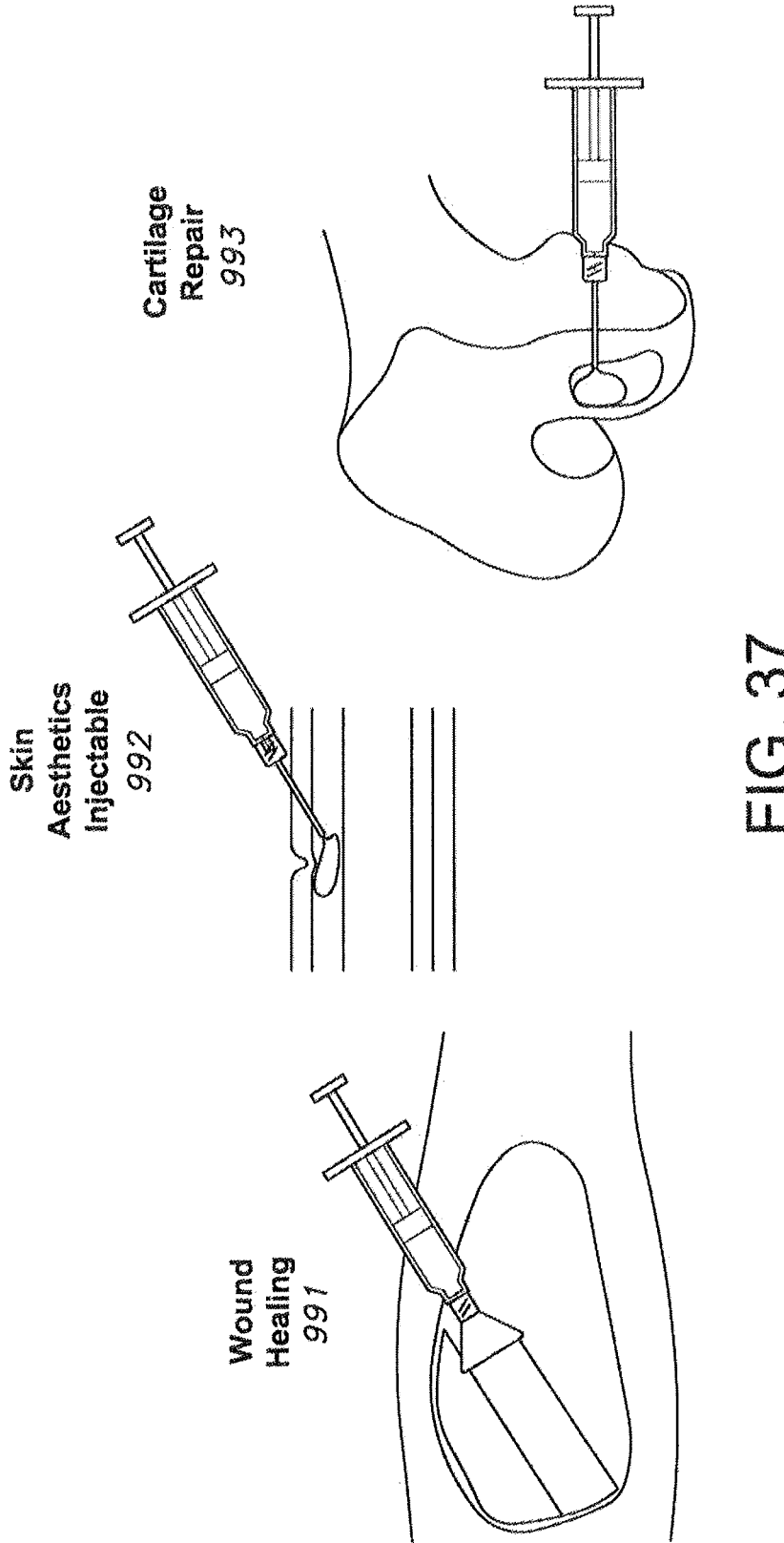
FIG. 37 shows the examples of clinical indications for the present invention.

FIG. 37 shows non-limiting examples of clinical indications including wound healing 990, skin anesthetic injectable 991 and cartilage repair 992 using injection devices with appropriate tip selection.

Figure 38:
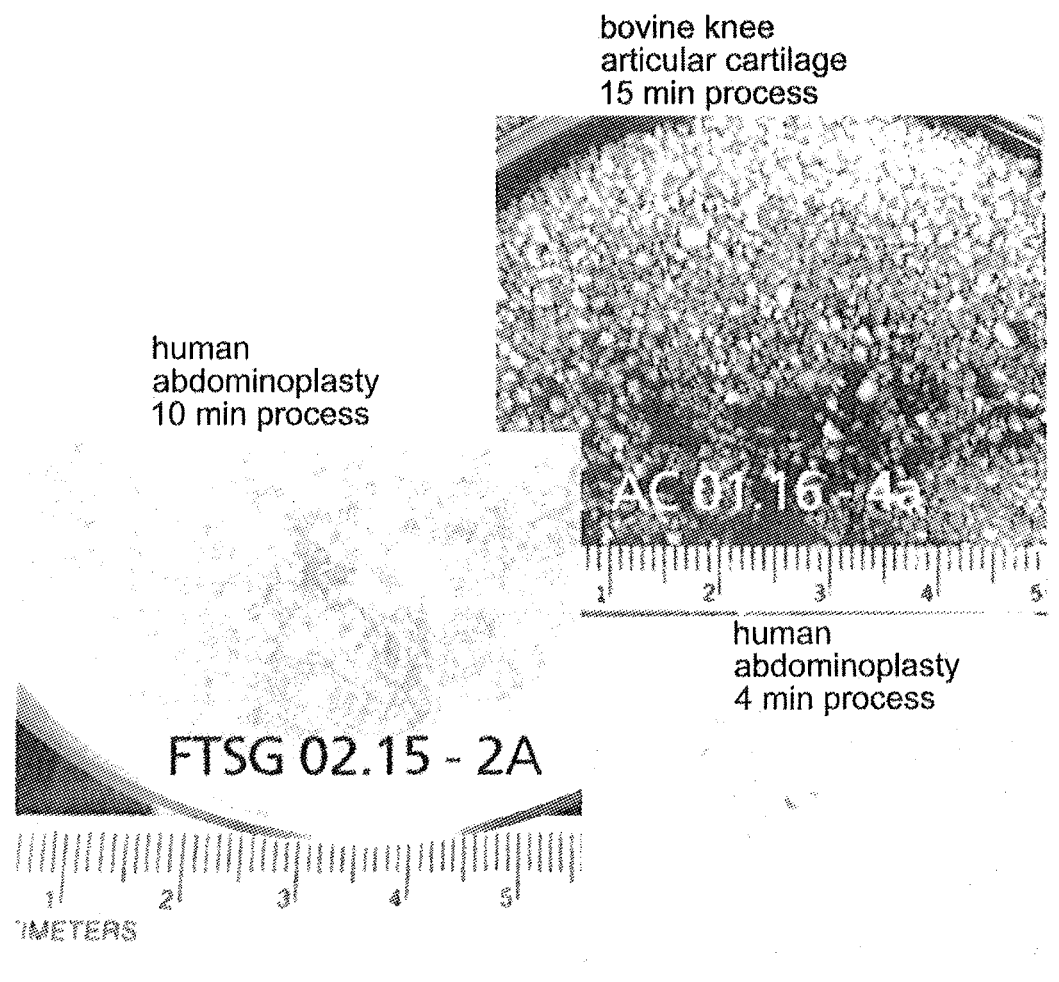
FIG. 38 shows the current developmental status of the present invention.

FIG. 38 shows morselized tissue of bovine knee articular cartilage, as well as morselized tissue from abdominoplastic formed using the inventive process. These morselized cartilage and skin particulates (particles) may be disbursed to a patient using any of the dispensing devices described herein. These results had been repeatedly verified to have 87-98% cellular viability using standard tripan and MTT test protocol.

The above-presented description and figures are intended by way of example only, and are not intended to limit the present invention in any way except as set forth in the following claims. It is particularly noted that persons skilled in the art can readily combine various technical aspects of the elements of the various exemplary embodiments described above in numerous other ways, all of which are considered to be within the scope of the invention.

What is claimed is:

1. Tissue particles, harvested from a full thickness skin graft and randomly morselized repeatedly to a random size and shape in a continuous circulating stream of a solution and full thickness skin particles, while maintaining a cell viability of at least 60%, said particles having an average size as measured across a largest dimension selected from the group consisting of: about 0.35 mm to 1.25 mm, about 0.5 mm to about 1.00 mm, about 0.5 mm to about 0.75 mm, about 0.25 mm to about 0.75 mm, and about 0.50 mm.

2. The morselized tissue particles of claim 1, wherein the viability is at least 85%.

3. The morselized tissue particles of claim 1, wherein the viability is selected from the group consisting of: at least 90%, at least 92%, at least 94%, at least 96%, at least 97%, at least 98%, at least 99%, and 87-98%.

4. The morselized tissue particles of claim 1, wherein an average size as measured across a largest dimension is about 0.25 mm to 0.75 mm, and wherein the viability is at least 90%.

5. The morselized tissue particles of claim 1, wherein an average size as measured across a largest dimension is about 0.50 mm.

6. A composition comprising the morselized tissue particles of claim 1, wherein the composition is in a form selected from the group consisting of a liquid, suspension, dispersion, cream, fluid, emulsion, paste, spray, and injectable.

7. The composition of claim 6, further comprising at least one selected from the group consisting of a liquid medium, fibrin glue, autologous platelet rich plasma, growth factors, binders, saline, buffer solution, and cell nurturing/preservation solution.

8. The composition of claim 7, wherein the liquid medium is a hydrophilic medium, an oleophilic medium, or an emulsion of hydrophilic and oleophilic mediums.

9. The composition of claim 6, wherein the composition is in the form of a suspension, further wherein the suspension is heterogeneous.

10. The composition of claim 6, wherein the composition is in the form of a suspension, further wherein the suspension is homogenous.

11. A surgical procedure comprising:
   harvesting the tissue particles of claim 1;
   processing the harvested tissue for less than 1 hour to prepare morselized tissue particles, wherein the morselized tissue particles have an average size as measured across a largest dimension of about 0.25 mm to 0.75 mm and a viability of at least 85%; and
   implanting the morselized tissue particles in a joint of the patient.

12. Morselized tissue particles, having an average size as measured across a largest dimension of about 0.20 mm to 1.50 mm, and a viability of at least 60%, wherein the morselized tissue particles are formed using a device for processing organ tissue comprising:

a pair of cutting devices supported in juxtaposition in a container, wherein at least one of the cutting devices is moveable with respect the other cutting device to slice tissue between thereof;

wherein at least one of the cutting devices is fixed with respect the moveable cutting device; and wherein an agitation device causes a vortex propulsion movement of fluid and tissue through the space between juxtaposed cutting devices.

13. The morselized tissue particles of claim 12, wherein the viability is at least 70%.

14. The morselized tissue particles of claim 12, wherein the viability is at least 85%.

15. The morselized tissue particles of claim 12, wherein the morselized tissue particles are morselized cartilage tissue particles.

16. The morselized cartilage tissue particles of claim 15, wherein the viability is at least 85%.

17. The morselized cartilage tissue particles of claim 15, wherein the viability is at least 92%.

18. The morselized cartilage tissue particles of claim 15, wherein the viability is at least 96%.

19. The morselized cartilage tissue particles of claim 15, wherein the viability is 87-98%.

20. The morselized cartilage tissue particles of claim 15, having an average size as measured across a largest dimension of about 0.50 mm and a viability of at least 90%.

21. A composition comprising the morselized cartilage tissue particles of claim 15, wherein the composition is in a form selected from the group consisting of a liquid, suspension, dispersion, cream, fluid, emulsion, paste, spray, and injectable.

22. The composition of claim 21, wherein the morselized cartilage tissue particles have an average size as measured across a largest dimension of about 0.50 mm.

23. The composition of claim 21, further comprising at least one selected from the group consisting of a liquid medium, fibrin glue, autologous platelet rich plasma, growth factors, binders, saline, buffer solution, and cell nurturing/preservation solution.

24. A method of repairing cartilage or treating a cartilage defect in a patient in need thereof, comprising administering the composition of claim 21 to the patient.

25. The method of claim 24, wherein the morselized cartilage tissue particles have an average size as measured across a largest dimension of about 0.50 mm.

26. The method of claim 25, wherein the composition is administered to the patient via syringe or spatula.

27. The method of claim 24, wherein the composition is administered to a joint of the patient.

28. The method of claim 24, wherein the morselized cartilage tissue particles is morselized articular cartilage tissue particles.

29. The morselized cartilage tissue particles of claim 15, wherein the source of the cartilage tissue is non-articular cartilage, articular cartilage, or a combination thereof.

30. A cartilage graft, comprising the morselized cartilage tissue particles of claim 15.

31. A surgical procedure comprising:

harvesting the tissue particles of claim 12;

processing the harvested tissue for less than 1 hour to prepare morselized tissue particles, wherein the morselized tissue particles have an average size as measured across a largest dimension of about 0.25 mm to 0.75 mm and a viability of at least 85%; and implanting the morselized tissue particles in a joint of the patient.

32. The surgical procedure of claim 31, wherein:

the at least one tissue portion is at least one cartilage tissue portion, the harvested tissue is harvested cartilage, and the morselized tissue particles are morselized cartilage tissue particles.

33. The surgical procedure of claim 31, wherein the harvested cartilage is harvested from the patient's non-articular cartilage or articular cartilage.

34. Viable tissue particles for treating a patient in need thereof, said tissue particles being harvested from a full thickness skin graft and randomly repeatedly morselized to a size and shape in a continuous circulating stream of a solution and full thickness skin particles, said continuous stream generated by an agitation device which produces a vortex propulsion between juxtaposed cutting devices, said particles having an average size as measured across a largest dimension selected from the group consisting of: about 0.35 mm to 1.25 mm, about 0.5 mm to about 1.00 mm, about 0.5 mm to about 0.75 mm, about 0.25 mm to about 0.75 mm, and about 0.50 mm.

\*    \*    \*    \*    \*